US012758785B2

(12) United States Patent
Woock et al.

(10) Patent No.: US 12,758,785 B2
(45) Date of Patent: Oct. 13, 2026

(54) DEVICES AND METHODS FOR IMPROVED REMOTE PROGRAMMING OF IMPLANTED NEUROSTIMULATION SYSTEMS

(71) Applicant: Axonics, Inc., Irvine, CA (US)

(72) Inventors: John Woock, Irvine, CA (US); Rinda Sama, Laguna Niguel, CA (US); Prabodh Mathur, Laguna Niguel, CA (US); Charles Borlase, Lake Forest, CA (US); Faizal Abdeen, Mission Viejo, CA (US); Guangqiang Jiang, Irvine, CA (US)

(73) Assignee: Axonics, Inc., Irvine, CA (US)

( * ) Notice: Subject to any disclaimer, the term of this patent is extended or adjusted under 35 U.S.C. 154(b) by 551 days.

(21) Appl. No.: 18/143,350

(22) Filed: May 4, 2023

(65) Prior Publication Data

US 2023/0355996 A1 Nov. 9, 2023

Related U.S. Application Data

(60) Provisional application No. 63/338,403, filed on May 4, 2022.

(51) Int. Cl.
*A61N 1/372* (2006.01)
*A61N 1/36* (2006.01)
(Continued)

(52) U.S. Cl.
CPC ..... *A61N 1/37264* (2013.01); *A61N 1/36146* (2013.01); *A61N 1/37217* (2013.01); (Continued)

(58) Field of Classification Search
CPC ............ A61N 1/37211; A61N 1/37217; A61N 1/37235; A61N 1/37247; A61N 1/37252; (Continued)

(56) References Cited

U.S. PATENT DOCUMENTS

| | | | |
|---|---|---|---|
| 10,384,067 | B2 | 8/2019 | Jiang et al. |
| 2010/0222845 | A1 | 9/2010 | Goetz |

(Continued)

FOREIGN PATENT DOCUMENTS

| | | |
|---|---|---|
| WO | 2020/257454 A1 | 12/2020 |

OTHER PUBLICATIONS

International Search Report and Written Opinion dated Jul. 26, 2023 issued by the International Searching Authority in related International Application No. PCT/US2023/020901; filed May 3, 2023.

*Primary Examiner* — Brian T Gedeon
(74) *Attorney, Agent, or Firm* — Seager Tufte & Wickhem, LLP

(57) ABSTRACT

Methods, devices and systems facilitating remote programming of an implanted neurostimulation system. Establishing communication between an implanted pulse generator (IPG) and a remote programming device associated with a remote support entity through one or more intermediary devices, which can utilize various communication protocols, such as Bluetooth (BT), MedRadio (MR), cellular, WiFi, or any combination thereof. The intermediary devices include a patient device, which can communicate directly with Bluetooth-enabled IPGs and a remote programming device, or can utilize additional intermediary devices such as a patient remote or adapter accessory to facilitate communication with existing non-BT enabled IPGs. The patient device and remote device can further include a software framework to facilitate communication between the IPG and the remote support entity, as well as collecting subjective/objective patient information. The system further include a web-based portal accessible by the patient device and remote device to further inform remote programming or self-programming.

32 Claims, 35 Drawing Sheets

(51) Int. Cl.
*G16H 10/60* (2018.01)
*G16H 40/67* (2018.01)

(52) U.S. Cl.
CPC ......... *A61N 1/37247* (2013.01); *G16H 10/60* (2018.01); *G16H 40/67* (2018.01)

(58) Field of Classification Search
CPC ............ A61N 1/37254; A61N 1/37264; A61N 1/37282; A61N 1/37288
See application file for complete search history.

(56) References Cited

U.S. PATENT DOCUMENTS

| | | | | |
|---|---|---|---|---|
| 2011/0264034 | A1 * | 10/2011 | Roberts | G16H 40/67 604/65 |
| 2013/0085550 | A1 * | 4/2013 | Polefko | A61N 1/37252 607/59 |
| 2016/0051825 | A1 * | 2/2016 | Ter-Petrosyan | A61N 1/37247 607/60 |
| 2022/0096847 | A1 * | 3/2022 | Shah | A61N 1/37247 |
| 2022/0134117 | A1 | 5/2022 | Woock et al. | |

* cited by examiner

CASE STUDY 1

Bipolar, Cathode = "-"; Anode= "+"

| Threshold (mA) | Recommendation A | Recommendation B | Recommendation C | Recommendation D |
|---|---|---|---|---|
| 1.7 | - | + | | + |
| 0.9 | | | - | |
| 1.2 | | | | - |
| 1.9 | + | - | + | |

Monopolar, IPG Can as anode

| Threshold (mA) | Recommendation A | Recommendation B | Recommendation C | Recommendation D |
|---|---|---|---|---|
| 1.7 | - | | | |
| 0.9 | | | - | |
| 1.2 | | | | - |
| 1.9 | | - | | |

*FIG. 12A*

CASE STUDY 2

Bipolar, Cathode = "-"; Anode= "+"

| Threshold (mA) | Recommendation A | Recommendation B | Recommendation C | Recommendation D |
|---|---|---|---|---|
| 1.3 | - | | - | + |
| 1.6 | | - | - | |
| 2.7 | | | | - |
| 4.1 | + | + | + | |

Monopolar, IPG Can as anode

| Threshold (mA) | Recommendation A | Recommendation B | Recommendation C | Recommendation D |
|---|---|---|---|---|
| 1.3 | - | | - | |
| 1.6 | | - | - | |
| 2.7 | | | | - |
| 4.1 | | | | |

*FIG. 12B*

DEVICES AND METHODS FOR IMPROVED REMOTE PROGRAMMING OF IMPLANTED NEUROSTIMULATION SYSTEMS

CROSS-REFERENCES TO RELATED APPLICATIONS

The present application claims priority to and the benefit of U.S. Provisional Patent Application No. 63/338,403. The foregoing provisional application is incorporated by reference herein.

The present application is generally related to U.S. Non-Provisional application Ser. No. 17/513,790, entitled "Devices and Methods for Remote Programming of Implanted Neurostimulation Systems," filed on Oct. 28, 2021; U.S. Non-Provisional application Ser. No. 16/871,738, entitled "Attachment Devices and Associated Methods of Use With a Nerve Stimulation Charging Device" filed on May 11, 2020; U.S. Non-Provisional patent application Ser. No. 14/827,067 entitled "Systems and Methods for Neurostimulation Electrode Configurations Based on Neural Localization," filed on Aug. 14, 2015 (now U.S. Pat. No. 9,855,423); U.S. Non-Provisional application Ser. No. 14/992,777, entitled "Patient Remote and Associated Methods of Use With a Nerve Stimulation System" filed on Jan. 11, 2016 (now U.S. Pat. No. 9,895,546); and U.S. Non-Provisional application Ser. No. 14/993,009, entitled "Improved Antenna and Methods of Use For an Implantable Nerve Stimulator" filed on Jan. 11, 2016 (now U.S. Pat. No. 9,700,731); each of which is assigned to the same assignee and incorporated herein by reference in its entirety for all purposes.

BACKGROUND

The present application relates to remote programming of neurostimulation treatment systems and associated devices, methods and system setups.

Treatments with implantable neurostimulation systems have become increasingly common in recent years. While such systems have shown promise in treating a number of conditions, effectiveness of treatment may vary considerably between patients. A number of factors may lead to the very different patient outcomes; and, viability of treatment may be difficult to determine before implantation. Current stimulation electrode placement/implantation techniques and known treatment setting techniques suffer from significant disadvantages. The nerve tissue structures of different patients may be quite different, with the locations and branching of nerves that perform specific functions and/or enervate specific organs being challenging to accurately predict or identify. The electrical properties of the tissue structures surrounding a target nerve structure may also be quite different among different patients, and the neural response to stimulation may be markedly dissimilar, with an electrical stimulation pulse pattern, pulse width, frequency, and/or amplitude that is effective to affect a body function of one patient and potentially imposing significant discomfort or pain, or having limited effect, on another patient. Even in patients where implantation of a neurostimulation system provides effective treatment, frequent adjustments and changes to the stimulation protocol are often required before a suitable treatment program may be determined, often involving repeated office visits and significant discomfort for the patient before efficacy is achieved. While more recently developed systems have improved upon lead placement and stimulation efficiency to improve consistency in treatment, many patients still require occasional adjustments or changes to the treatment program. Such reprogramming often requires an in-person office visit, and sometimes repeat offices visits. Given that implanted neurostimulation systems utilize specialized local communication (e.g. MedRadio) to communicate with accessory components within the system and the patient lacks the expertise or permissions to adjust or modify therapy, this presents significant barriers to programming an implanted system without requiring in-person visit with a clinician or system technician. The design of current therapy systems simply do not lend themselves to control or programming remotely. These challenges present significant obstacles to maintaining long-term efficacious treatment of patients that live in remote locations or those patients that are elderly or in vulnerable patient populations.

Therefore, it would be desirable to provide improved systems, devices and methods by which an implanted neurostimulation system may be adjusted or reprogrammed remotely by a clinician or technical expert without requiring an in-person visit. It would be further helpful for such methods to facilitate interaction between the patient and clinician to provide the benefits of an in-person visit while still allowing remote programming of the system.

SUMMARY

The present application generally relates to remote programming of neurostimulation treatment systems and associated devices and methods. The application has particular application to sacral nerve stimulation treatment systems configured to treat bladder and bowel related dysfunctions. It will be appreciated however that the various exemplary embodiments disclosed herein may also be utilized for the treatment of pain or other indications, such as movement or affective disorders, or various other implanted medical devices, as will be appreciated by one of skill in the art.

Disclosed embodiments relate to methods, user devices, intermediary communication devices and specialized application software that facilitates remote programming of an implanted by a remote device. As discussed above, there is an increasing need for remote programming of implanted medical devices, which allows healthcare workers to remotely connect with patients over a phone or tablet device and to reprogram or troubleshoot their implanted medical device in their body. By use of a specialized intermediary communication devices utilizing various types of communication (e.g. Bluetooth (BT), MedRadio (MR), cellular/WiFi, or any combination thereof), and specialized software applications, a user can utilize existing equipment as well as their personal computing devices to establish a live communication session for programming of their implanted device or troubleshoot their device remotely in manner that is convenient as well as safe and secure for all parties. In some exemplary embodiments, the user can utilize custom devices and/or accessory devices to streamline the system setup and/or to provide additional functionality beyond the capabilities of existing devices or personal devices. In addition, the application discloses various options and system setups that can accommodate a range of available IPG designs (rechargeable and non-rechargeable) with varied communication capabilities. In some exemplary embodiments, the remote programing setup system is designed so as to be backwards compatible with existing device/systems (non-BT enabled IPGs). In other embodiments, the system setup is designed to be forward compatible with next generation remote programming functionality (e.g. IPGs or patient remotes designed with both MR and BT functionality). In still another aspect, the system setup may include a patient database portal by which therapy information may be periodically updated, and can inform the remote programing by the remote device or inform self-programming with the patient device. The patient portal may be web-based and hosted on a secure server and may be accessed by the patient device or the remote programming device. In another aspect, the remote programming system setups described herein may be integrated into a telehealth platform (e.g., Teledoc, VSee, Doxy.me, OhMD, Whereby, Mend, Updox, NextGen Healthcare EHR, etc.). Generally, telehealth platforms encompass the technology infrastructure, services, and support that allows private, secure, HIPAA-compliant, and high-quality virtual medical consultations and treatments remotely. Such telehealth systems may include phone, videoconferences, or text-based communication, typically through a remote communication system, often using the personal device of the patient. Accordingly, the remote programing features described herein may be incorporated into these telehealth platforms so as to leverage existing functionality of these platforms for the purpose of remote programming.

A typical implanted medical device communicates with its peripheral devices (e.g. clinician programmer, patient remote control etc.) through specific frequencies, that are dedicated to medical devices use, such as the Medical Device Radio communications Service (MedRadio) band (e.g. 401-406 MHz, 413-419 MHz, 426-432 MHz, 438-444 MHz, and 451-457 MHz range). In addition, Medical Body Area Networks (MBANs), which are low power networks of sensors worn on the body controlled by a hub device that is located either on the body or in close proximity, operate in the 2360-2400 MHz band. Standard smartphones or tablets are not suited for communication with or programming of implanted medical devices. By use of specialized intermediary devices or updates to existing accessory devices, a live communication session may be established remotely between the implanted medical device, a patient device and a remote device to allow programming.

The intermediary device may communicate with an implanted medical device on one end through the MedRadio band and to a patient's phone or a tablet device, either an iOS or android device, through Bluetooth or low energy Bluetooth on the other end. In some exemplary embodiments, the system utilizes an existing accessory, such as the Patient Remote or Charger, as the intermediary device. In some exemplary embodiments, the specialized intermediary device may be configured to plug into a user's device (e.g., smartphone, tablet, laptop) through its charging port or other ports (e.g., USB-C, USB, etc.). The intermediary device may then be powered and recognized by the user's phone or tablet device. A specialized application ("App") may be developed and pre-downloaded to the user's device. The user may be the patient, a clinician or patient advocate. The App may be used to make changes to program settings of the implanted device or troubleshoot, by commanding the implanted device to run a diagnosis on its own and report back to the user device. In other embodiments, the specialized device may be a separate device that communicates with the patient device, such as a smartphone or tablet, by radio communications, for example, by Bluetooth or near field communication ("NFC"), and that communicates with the implanted device by MedRadio. In this embodiment, the intermediary device contains a power source and is self-powered. As noted above, a specific App may be developed and pre-downloaded to the user's device to allow changes to program settings or troubleshooting of the implanted device.

A method of remotely programming an implanted neurostimulation system is disclosed herein. The method may include the steps of: receiving, with a remote device, a patient request for programming of an implantable pulse generator of a neurostimulation system implanted in the patient; establishing a communication session between the implantable pulse generator of the neurostimulation system and a remote device associated with a remote support entity through one or more intermediary local devices; receiving program information and patient information with the remote device; determining or receiving, with the remote device, a program update regarding updating of one or more parameters of the current program or a new program to be applied by the implanted neurostimulation system; and programming the implantable pulse generator, with the remote device through the one or more intermediary devices, with the program update. In some exemplary embodiments, the program information includes a current therapy program applied by the implanted neurostimulation system. In some exemplary embodiments, the patient information comprises patient identifying information, objective information and/or subjective information regarding treatment. The objective information may include, but is not limited to, any of: numbers of voids, volume of each void, number of pads, a Visual Analogue Scale (VAS) pain score, a Quality of Life (QoL) score, hours of sleep, and current stimulation therapy parameters. The subjective information may include, but is not limited to, any of: what the patient is feeling, mood changes, and sleep quality.

In some exemplary embodiments, the one or more intermediary local devices includes any of: a charger device, a patient remote, a personal computing device of the patient, a specialized dedicated communication device. In some exemplary embodiments, the one or more intermediary devices includes a first and second intermediary device, the first intermediary device communicates with the implantable pulse generator and the second intermediary device, and the second intermediary device communicates with the first intermediary device and the remote device of the remote support entity. In some exemplary embodiments, the first intermediary device is any of a: charger, a patient remote, a specialized communicator device, and a plug-in accessory into a personal computing device of the patient. The first intermediary device communicates with the implantable pulse generator by a first communication scheme (e.g. MedRadio). The second intermediary device communicates with the first intermediary device by a second communication scheme (e.g. Bluetooth) and can communicate with the remote device by another communication scheme (e.g. through Wifi, cellular, wire connection or any combination thereof).

In some exemplary embodiments, the second intermediary device includes a specialized Patient App specifically configured for facilitating programming. The Patient App may be configured to access or store the program information and communicate to the remote device for programming. In some exemplary embodiments, the Patient App may be configured to access the program information from a data center associated with a first party developer of the implantable pulse generator. In some exemplary embodiments, the Patient App may be configured to access the program information from the implantable pulse generator via the first intermediary device. In some exemplary embodiments, the Patient App is further configured to receive a patient input via a user interface regarding the current therapy program and/or the patient information. The Patient App can further include a bladder and/or voiding diary that stores subjective information regarding efficacy of the current therapy program and which may be accessed by the remote entity during programming. The subjective information may be collected and/or logged periodically within the Patient App over a duration of at least multiple days. In some exemplary embodiments, the Patient App may be configured to conduct a live communication session, such as a live video call, between the patient and a remote device of a remote support entity. The communication between the remote device and the one or more local intermediary devices can utilize any of: a cloud-based server, a local server of the remote entity, a hosted server hosted by a third party. In some exemplary embodiments, the remote entity is associated with a first party developer of the implantable pulse generator and/or a specialized Patient App on the one or more local intermediary devices. In some exemplary embodiments, the remote entity is a third party that is technical consultant, a treating physician, a clinician or a health care provider personnel. In some exemplary embodiments, the Patient App may be configured to be installed on the user's personal portable computing device and is not accessible by an internet browser.

In another aspect, the remote device may include a specialized Remote Programming App operating thereon. The Remote Programming App may be configured to be served to an internet browser and accessed by the remote device. The remote device may be any of a smartphone, tablet, laptop and a desktop computing device. In some exemplary embodiments, the Remote Programming App may be configured for installation and access on a portable computing device associated with the treating clinician or associated health care provider. In some exemplary embodiments, the Remote Programming App may be configured to establish communication with the patient through a back-end associated with a first party developer of the implantable pulse generator. The communication session may include accessing of the patient information and/or the program information from a data center associated with the first party developer of the implantable pulse generator that is accessed through the back-end. In some exemplary embodiments the back-end is cloud based, a local server of the first party, or a hosted server. In some exemplary embodiments, the initial communication is established in response to the remote entity or associated entity receiving a request, initiated by the patient with the second intermediary device, for programming. In some exemplary embodiments, establishing communication comprises exchanging identification information as to the implantable pulse generator, the patient and the remote entity between the second intermediary device and the remote device to ensure secure authenticated communication during the session. In some exemplary embodiments, the remote device has administrative control of the implantable pulse generator during at least part of the communication session that exceeds that of the patient. In some exemplary embodiments, the method includes accessing, with the remote device, multiple recommended neurostimulation programs that includes the current therapy program; and selecting, with the remote device, another of the multiple recommended neurostimulation programs for application as the new updated program. Multiple recommended neurostimulation programs may be stored on any of the implantable pulse generator or in a separate data center and accessed by the remote device using the patient information.

Methods of programming an implanted neurostimulation system remotely by use of a patient device are disclosed herein. The methods may include steps of: establishing, with the patient device, a communication session with a remote device associated with the remote support entity; sending, with the patient device, patient information to the remote device and/or program information regarding a current therapy program applied by the implantable pulse generator of the implanted neurostimulation system; receiving, with the patient device, a program update from the remote device regarding updating of one or more parameters of the current program or a new program; and outputting, with the patient device, the program update to the implanted neurostimulation system, thereby programming the implantable pulse generator from the remote device via the patient device, with the program update of the one or more parameters of the current program or the new program.

Various methods of programming an implanted neurostimulation system remotely with a remote device are disclosed herein. The methods may include steps of: establishing a communication session between an implantable pulse generator of the neurostimulation system implanted in a patient and a remote device associated with a remote support entity through one or more intermediary local devices for programming and/or reprogramming of the implantable pulse generator by the remote entity; receiving program information, with the remote device, wherein the program information includes a current therapy program on the implanted neurostimulation system; receiving patient information regarding the current therapy program, with the remote device via the one or more local intermediary devices, wherein the patient information includes patient identifying information and/or subjective information regarding therapy; determining or receiving, with the remote device, a program update regarding updating of one or more parameters of the current program or a new program for the implanted neurostimulation system based on the current based on the therapy program information and the patient information; and programming the implantable pulse generator, with the remote device through the one or more intermediary devices, with the program update.

A system for programming an implanted neurostimulation system remotely is also disclosed. The system may include an implantable pulse generator, a first and second intermediary device, and a remote device of a remote support entity. The implantable pulse generator of the neurostimulation system is implanted in a patient and includes one or more antennas for communicating wirelessly with one or more external devices by a first communication. The first intermediary device may be configured to communicate with the implantable pulse generator and one or more additional devices by local communication. The second intermediary device, associated with the patient, may be configured to communicate with the first intermediary device by local communication and one or more additional devices by remote communication. The second intermediary device includes a user interface for receiving a patient input from the patient. The remote device associated with a remote support entity may be configured to communicate with the second intermediary device by remote communication, wherein the remote device includes a user interface for receiving an input from the remote support entity. In some exemplary embodiments, the system may be configured to establish a communication session between the implantable pulse generator of the neurostimulation system and the remote device through the first and second intermediary local devices through which program information and/or patient information is received by the remote device for programming and/or reprogramming of the implantable pulse generator by the remote entity.

An embodiment of a patient device configured to facilitate programming of an implanted neurostimulation system remotely is disclosed herein. The patient device may include a portable housing, a communication module, a user interface and a processor module disposed within the housing. The communication module has one or more antennas with a remote communication antenna for communicating with one or more remote devices through a network, and a local communication antenna for locally communicating with one or more intermediary devices and/or an implantable pulse generator. The processor module includes a processor and a memory having stored thereon computer executable instructions configured for programming the implantable pulse generator by the remote device through the patient device. In some exemplary embodiments, the patient device may be a portable computing device, such as a laptop or smartphone, or a specialized device, and may include a specialized Patient App to facilitate programming according to any of the aspects described herein.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

FIGS. 12A-12B illustrate electrode configuration recommendations based on example case studies of electrode thresholds.

DETAILED DESCRIPTION

Figure 1:
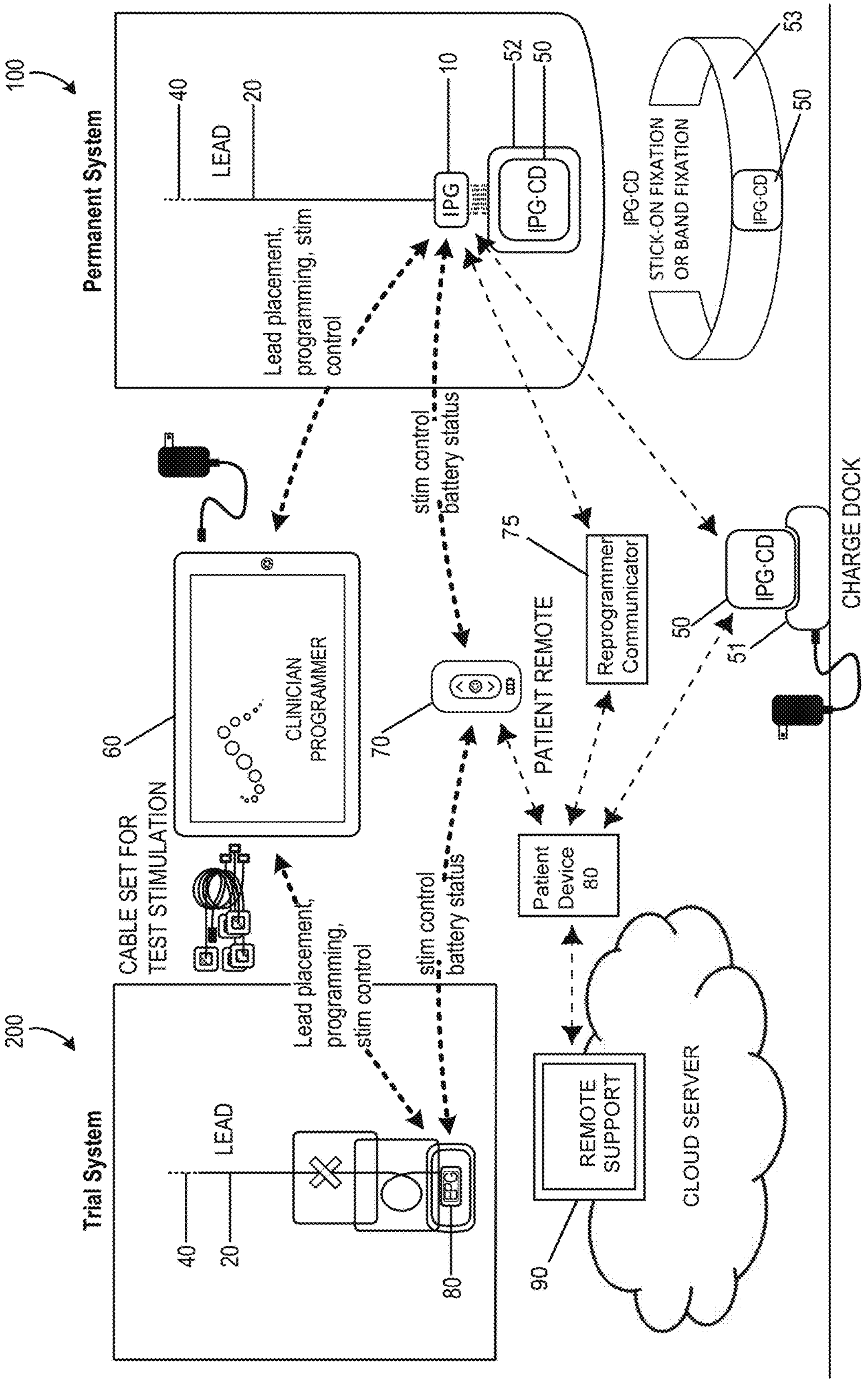
FIG. 1 schematically illustrates a nerve stimulation system, which includes a clinician programmer and a patient remote used in positioning and/or programming of both a trial neurostimulation system and a permanently implanted neurostimulation system.

The disclosed embodiments relate to remote programming of implanted neurostimulation treatment systems and associated devices, as well as associated devices to facilitate remote programming. Particular embodiments relate to sacral nerve stimulation treatment systems configured to treat bladder dysfunctions, including overactive bladder ("OAB"), as well as fecal dysfunctions and relieve symptoms associated therewith. For ease of description, the embodiments may be described in its use for OAB, it will be appreciated however that the disclosed embodiments may also be utilized for any variety of neuromodulation uses, such as bowel disorders (e.g., fecal incontinence, fecal frequency, fecal urgency, and/or fecal retention), the treatment of pain or other indications, such as movement or affective disorders, as will be appreciated by one of skill in the art.

I. Neurostimulation Indications

Neurostimulation (or neuromodulation as may be used interchangeably hereunder) treatment systems, such as any of those described herein, may be used to treat a variety of ailments and associated symptoms, such as acute pain disorders, movement disorders, affective disorders, as well as bladder related dysfunction and fecal dysfunction. Examples of pain disorders that may be treated by neurostimulation include failed back surgery syndrome, reflex sympathetic dystrophy or complex regional pain syndrome, causalgia, arachnoiditis, and peripheral neuropathy. Movement orders include muscle paralysis, tremor, dystonia and Parkinson's disease. Affective disorders include depressions, obsessive-compulsive disorder, cluster headache, Tourette syndrome and certain types of chronic pain. Bladder related dysfunctions include but are not limited to OAB, urge incontinence, urgency-frequency, and urinary retention. OAB may include urge incontinence and urgency-frequency alone or in combination. Urge incontinence is the involuntary loss or urine associated with a sudden, strong desire to void (urgency). Urgency-frequency is the frequent, often uncontrollable urges to urinate (urgency) that often result in voiding in very small amounts (frequency). Urinary retention is the inability to empty the bladder. Neurostimulation treatments may be configured to address a particular condition by effecting neurostimulation of targeted nerve tissues relating to the sensory and/or motor control associated with that condition or associated symptom. Bowel disorders may include any of the variety of inflammatory, motility, and incontinence conditions.

In one aspect, the methods and systems described herein are particularly suited for treatment of urinary and fecal dysfunctions. These conditions have been historically under-recognized and significantly underserved by the medical community. OAB is one of the most common urinary dysfunctions. It is a complex condition characterized by the presence of bothersome urinary symptoms, including urgency, frequency, nocturia and urge incontinence. It is estimated that about 40 million Americans suffer from OAB. Of the adult population, about 16% of all men and women live with OAB symptoms.

OAB symptoms can have a significant negative impact on the psychosocial functioning and the quality of life of patients. People with OAB often restrict activities and/or develop coping strategies. Furthermore, OAB imposes a significant financial burden on individuals, their families, and healthcare organizations. The prevalence of co-morbid conditions is also significantly higher for patients with OAB than in the general population. Co-morbidities may include falls and fractures, urinary tract infections, skin infections, vulvovaginitis, cardiovascular, and central nervous system pathologies. Chronic constipation, fecal incontinence, and overlapping chronic constipation occur more frequently in patients with OAB.

II. Sacral Neuromodulation

SNM is an established therapy that provides a safe, effective, reversible, and long-lasting treatment option for the management of urge incontinence, urgency-frequency, and non-obstructive urinary retention. SNM therapy involves the use of mild electrical pulses to stimulate the sacral nerves located in the lower back. Electrodes are placed next to a sacral nerve, usually at the S3 level, by inserting the electrode leads into the corresponding foramen of the sacrum. The electrodes are inserted subcutaneously and are subsequently attached to an implantable pulse generator (IPG). The safety and effectiveness of SNM for the treatment of OAB, including durability at five years for both urge incontinence and urgency-frequency patients, is supported by multiple studies and is well-documented. SNM has also been approved to treat chronic fecal incontinence in patients who have failed or are not candidates for more conservative treatments.

A. Implantation of Sacral Neuromodulation System

Currently, SNM qualification has a trial phase, and is followed if successful by a permanent implant. The trial phase is a test stimulation period where the patient is allowed to evaluate whether the therapy is effective. Typically, there are two techniques that are utilized to perform the test stimulation. The first is an office-based procedure termed the Percutaneous Nerve Evaluation (PNE) and the other is a staged trial.

In the PNE, a foramen needle is typically used first to identify the optimal stimulation location, usually at the S3 level, and to evaluate the integrity of the sacral nerves. Motor and sensory responses are used to verify correct needle placement. A temporary stimulation lead (a unipolar electrode) is then placed near the sacral nerve under local anesthesia. This procedure may be performed in an office setting without fluoroscopy. The temporary lead is then connected to an external pulse generator (EPG) taped onto the skin of the patient during the trial phase. The stimulation level may be adjusted to provide an optimal comfort level for the particular patient. The patient will monitor his or her voiding for 3 to 7 days to see if there is any symptom improvement. The advantage of the PNE is that it is an incision free procedure that may be performed in the physician's office using local anesthesia. If a patient fails this trial test, the physician may still recommend the staged trial as described below. If the PNE trial is positive, the temporary trial lead is removed and a permanent quadri-polar tined lead is implanted along with an IPG under general anesthesia.

Figure 3:
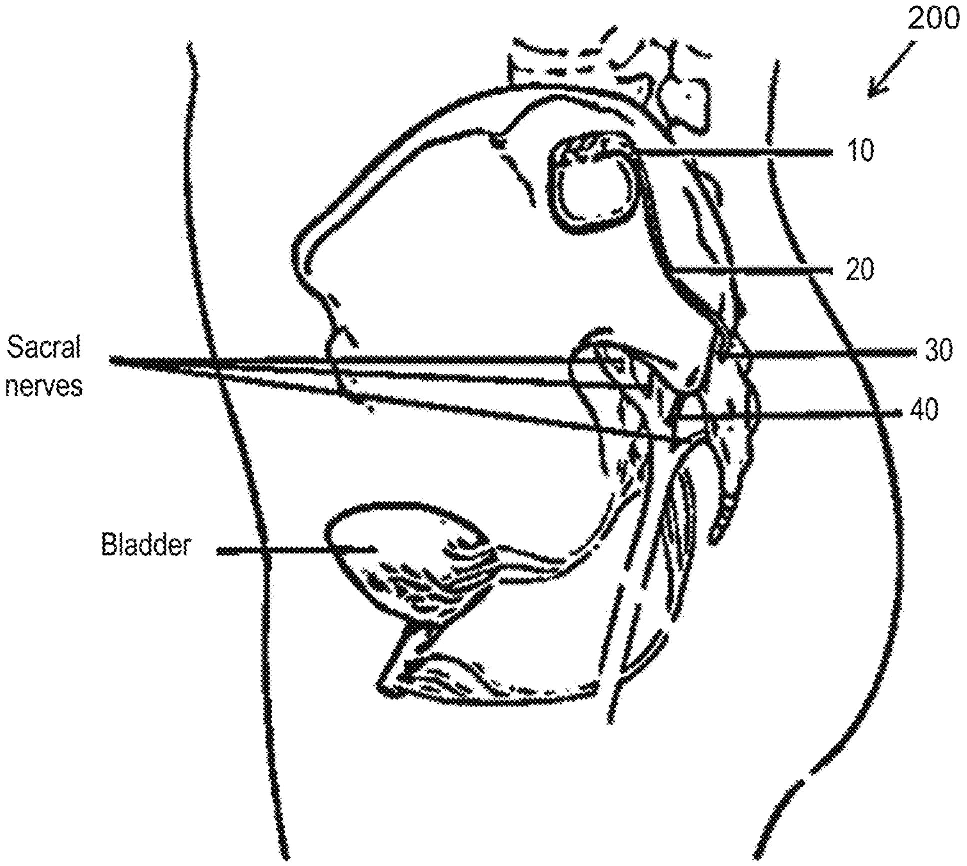
FIG. 3 shows an example of a fully implanted neurostimulation system.

A staged trial involves the implantation of the permanent quadri-polar tined stimulation lead into the patient from the start. It also requires the use of a foramen needle to identify the nerve and optimal stimulation location. The lead is implanted near the S3 sacral nerve and is connected to an EPG via a lead extension. This procedure is performed under fluoroscopic guidance in an operating room and under local or general anesthesia. The EPG is adjusted to provide an optimal comfort level for the patient and the patient monitors his or her voiding for up to two weeks. If the patient obtains meaningful symptom improvement, he or she is considered a suitable candidate for permanent implantation of the IPG under general anesthesia, typically in the upper buttock area, as shown in FIG. 3.

In regard to measuring outcomes for SNM treatment of voiding dysfunction, the voiding dysfunction indications (e.g., urge incontinence, urgency-frequency, and non-obstructive urinary retention) may be evaluated by unique primary voiding diary variables. The therapy outcomes are measured using these same variables. SNM therapy is considered successful if a minimum of 50% improvement occurs in any of primary voiding diary variables compared with the baseline. For urge incontinence patients, these voiding diary variables may include: number of leaking episodes per day, number of heavy leaking episodes per day, and number of pads used per day. For patients with urgency-frequency, primary voiding diary variables may include: number of voids per day, volume voided per void and degree of urgency experienced before each void. For patients with retention, primary voiding diary variables may include: catheterized volume per catheterization and number of catheterizations per day. For fecal incontinence patients, the outcome measures captured by the voiding diary include: number of leaking episodes per week, number of leaking days per week, and degree of urgency experienced before each leak.

The disclosed embodiments relate to remote programming of a neurostimulation system adapted to deliver neurostimulation to targeted nerve tissues in a manner that results in partial or complete activation of the target nerve fibers, causes the augmentation or inhibition of neural activity in nerves, potentially the same or different than the stimulation target, that control the organs and structures associated with bladder and bowel function.

B. Neurostimulation Lead Placement and Programming

Neurostimulation relies on consistently delivering therapeutic stimulation from a pulse generator, via one or more neurostimulation electrodes, to particular nerves or targeted regions. The neurostimulation electrodes are provided on a distal end of an implantable lead that may be advanced through a tunnel formed in patient tissue. Implantable neurostimulation systems provide patients with great freedom and mobility, but it may be easier to adjust the neurostimulation electrodes of such systems before they are surgically implanted. It is desirable for the physician to confirm that the patient has desired motor and/or sensory responses before implanting an IPG. For at least some treatments (including treatments of at least some forms of urinary and/or fecal dysfunction), demonstrating appropriate motor responses may be highly beneficial for accurate and objective lead placement while the sensory response may not be required or not available (e.g., patient is under general anesthesia).

Placement and calibration of the neurostimulation electrodes and implantable leads sufficiently close to specific nerves may be beneficial for the efficacy of treatment. Accordingly, aspects and embodiments of the present disclosure are directed to aiding and refining the accuracy and precision of neurostimulation electrode placement. Further, aspects and embodiments of the present disclosure are directed to aiding and refining protocols for setting therapeutic treatment signal parameters for a stimulation program implemented through implanted neurostimulation electrodes.

In exemplary embodiments, determination of whether or not an implantable lead and neurostimulation electrode is located in a desired or correct location may be accomplished by utilizing the neuromuscular responses to test stimulations, for example, by observed responses or through use of electromyography ("EMG"), also known as surface electromyography. EMG, is a technique that uses an EMG system or module to evaluate and record electrical activity produced by muscles, producing a record called an electromyogram. EMG detects the electrical potential generated by muscle cells when those cells are electrically or neurologically activated. The signals may be analyzed to detect activation level or recruitment order. EMG may be performed through the skin surface of a patient, intramuscularly or through electrodes disposed within a patient near target muscles, or using a combination of external and internal structures. When a muscle or nerve is stimulated by an electrode, EMG may be used to determine if the related muscle is activated, (i.e. whether the muscle fully contracts, partially contracts, or does not contract) in response to the stimulus. Accordingly, the degree of activation of a muscle can indicate whether an implantable lead or neurostimulation electrode is located in the desired or correct location on a patient. Further, the degree of activation of a muscle can indicate whether a neurostimulation electrode is providing a stimulus of sufficient strength, amplitude, frequency, or duration to affect a treatment regimen on a patient. Thus, use of EMG provides an objective and quantitative means by which to standardize placement of implantable leads and neurostimulation electrodes, reducing the subjective assessment of patient sensory responses. While use of EMG responses is discussed in some of the exemplary programming methods described below, it is appreciated that the remote programming concepts described herein are applicable to any type of programming approaches, including those that do not utilize EMG.

C. System Embodiments

FIG. 1 schematically illustrates exemplary nerve stimulation system setups, which includes a setup for use in a trial neurostimulation system 200 and a setup for use in a permanently implanted neurostimulation system 100. The EPG 80 and IPG 50 are each compatible with and wirelessly communicate with a clinician programmer (CP) 60 and a patient remote 70, which are used in positioning and/or programming the trial neurostimulation system 200 and/or permanently implanted system 100 after a successful trial. As discussed above, the system utilizes a cable set and EMG sensor patches in the trial system setup 100 to facilitate lead placement and neurostimulation programming. CP may include specialized software, specialized hardware, and/or both, to aid in lead placement, programming, re-programming, stimulation control, and/or parameter setting. In addition, each of the IPG and the EPG allows the patient at least some control over stimulation (e.g., initiating a pre-set program, increasing or decreasing stimulation), and/or to monitor battery status with the patient remote. This approach also allows for an almost seamless transition between the trial system and the permanent system. The CP may be used by a clinician during initial programming of the EPG and IPG or may be used remotely during subsequent remote programming of the IPG in a communication session with Remote Support 90. The system may include one or more intermediary devices to facilitate the communication session between the Remote Support and the IPG, as well as the patient. The one or more intermediary devices may include Patient Device 80, and can further utilize accessory devices, such as Charger 50, Patient Remote 70, or Reprogrammer Communicator 75, to allow communication between the Patient Device 80 and the IPG.

The CP 60 is used by a physician to adjust the settings of the EPG and/or IPG while the lead is implanted within the patient during initial programming. The CP may be a tablet computer used by the clinician to program the IPG, or to control the EPG during the trial period. The CP can also include capability to record stimulation-induced electromyograms to facilitate lead placement and programming. The patient remote 70 can allow the patient to turn the stimulation on or off, or to vary stimulation from the IPG while implanted, or from the EPG during the trial phase. The CP 60 has a control unit which may include a microprocessor and specialized computer-code instructions for implementing methods and systems for use by a physician in deploying the treatment system and setting up treatment parameters. The CP generally includes a graphical user interface to facilitate clinician input for programming. The CP may include a module with hardware and computer-code to execute EMG analysis, where the module may be a component of the control unit microprocessor, a pre-processing unit coupled to or in-line with the stimulation and/or sensory cables, or the like.

Figure 2A:
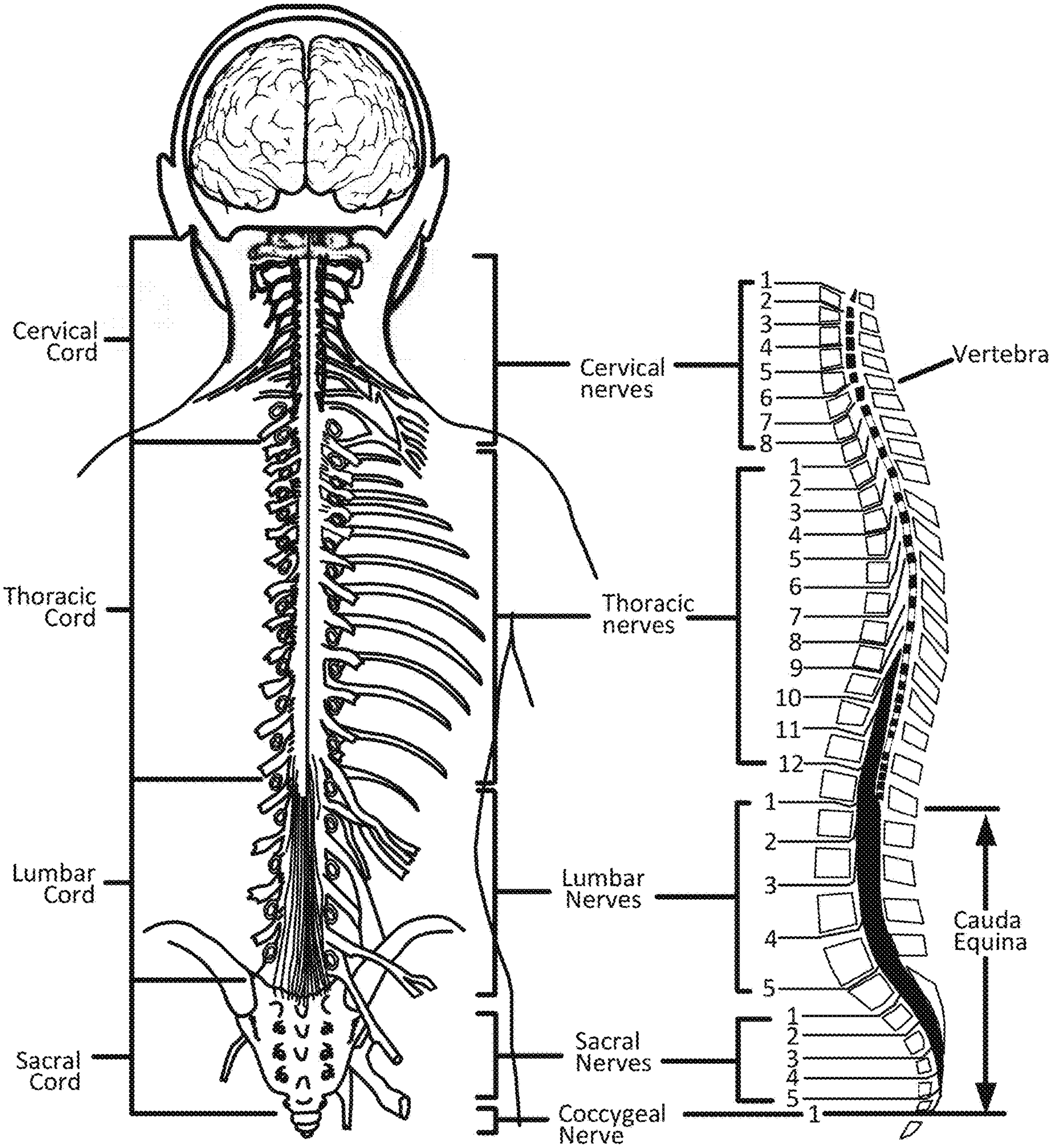
FIGS. 2A-2C show diagrams of the nerve structures along the spine, the lower back and sacrum region, which may be stimulated by systems and devices disclosed herein.
Figure 2B:
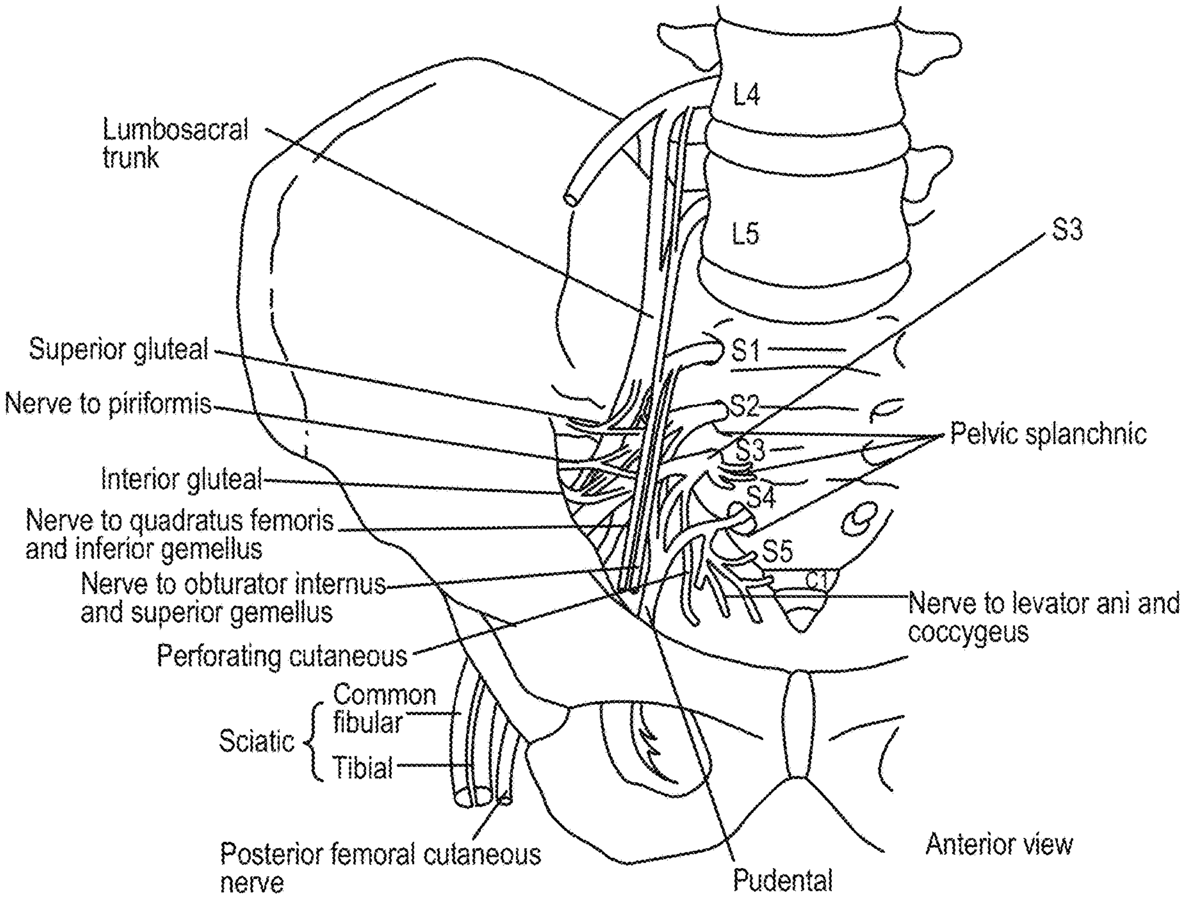
Figure 2C:
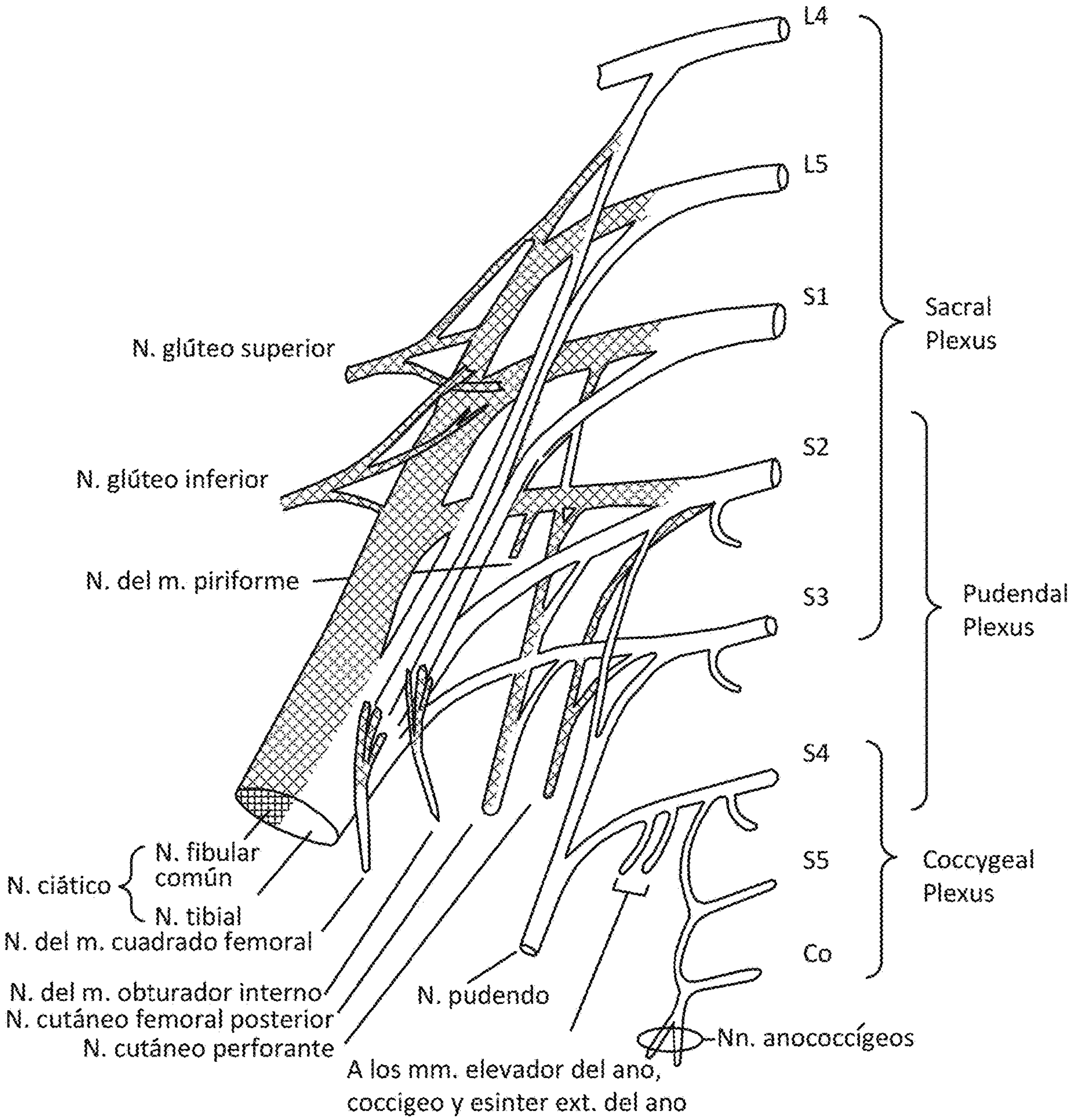

In other aspects, the CP 60 allows the clinician to read the impedance of each electrode contact whenever the lead is connected to an EPG, an IPG or a CP to ensure reliable connection is made and the lead is intact. This may be used during positioning the lead and in programming the leads to ensure the electrodes are properly functioning. The CP 60 is also able to save and display previous (e.g., up to the last four) programs that were used by a patient to help facilitate re-programming. Alternatively, the recent programs may be stored on the IPG, the Patient Device, or stored in a profile of the patient and stored in a Data Center accessible by the Patient Device and/or the CP. In some exemplary embodiments, the CP 60 further includes a USB port for saving reports to a USB drive and a charging port. The CP may be configured to operate in combination with an EPG when placing leads in a patient body as well with the IPG during programming. The CP may be electronically coupled to the EPG during test simulation through a specialized cable set or through wireless communication, thereby allowing the CP to configure, modify, or otherwise program the electrodes on the leads connected to the EPG. The CP may also include physical or virtual on/off buttons to turn the CP on and off and/or to turn stimulation on and off FIGS. 2A-2C show diagrams of various nerve structures of a patient, which may be used in neurostimulation treatments. FIG. 2A shows the different sections of the spinal cord and the corresponding nerves within each section. The spinal cord is a long, thin bundle of nerves and support cells that extend from the brainstem along the cervical cord, through the thoracic cord and to the space between the first and second lumbar vertebra in the lumbar cord. Upon exiting the spinal cord, the nerve fibers split into multiple branches that innervate various muscles and organs transmitting impulses of sensation and control between the brain and the organs and muscles. Since certain nerves may include branches that innervate certain organs, such as the bladder, and branches that innervate certain muscles of the leg and foot, stimulation of the nerve at or near the nerve root near the spinal cord can stimulate the nerve branch that innervate the targeted organ, which may also result in muscle responses associated with the stimulation of the other nerve branch. Thus, by monitoring for certain muscle responses, either visually, through the use of EMG as described herein or both, the physician can determine whether the targeted nerve is being stimulated. While stimulation at a certain level may evoke robust muscle responses visible to the naked eye, stimulation at a lower level (e.g. sub-threshold) may still provide activation of the nerve associated with the targeted organ while evoking no corresponding muscle response or a response only visible with EMG. In some exemplary embodiments, this low level stimulation also does not cause any paresthesia. This is advantageous as it allows for treatment of the condition by neurostimulation without otherwise causing patient discomfort, pain or undesired muscle responses.

FIG. 2B shows the nerves associated with the lower back section, in the lower lumbar cord region where the nerve bundles exit the spinal cord and travel through the sacral foramens of the sacrum. In some exemplary embodiments, the neurostimulation lead is advanced through the foramen until the neurostimulation electrodes are positioned at the anterior sacral nerve root, while the anchoring portion of the lead proximal of the stimulation electrodes are generally disposed dorsal of the sacral foramen through which the lead passes, so as to anchor the lead in position. FIG. 2C shows detail views of the nerves of the lumbosacral trunk and the sacra plexus, in particular, the SI-SS nerves of the lower sacrum. The S3 sacral nerve is of particular interest for treatment of bladder related dysfunction, and in particular OAB.

FIG. 3 schematically illustrates an example of a fully implanted neurostimulation system 100 adapted for sacral nerve stimulation. Neurostimulation system 200 includes an IPG implanted in a lower back region and connected to a neurostimulation lead extending through the S3 foramen for stimulation of the S3 sacral nerve. The lead is anchored by a tined anchor portion 30 that maintains a position of a set of neurostimulation electrodes 40 along the targeted nerve, which in this example, is the anterior sacral nerve root S3 which enervates the bladder so as to provide therapy for various bladder related dysfunctions. While this embodiment is adapted for sacral nerve stimulation, it is appreciated that similar systems may be used in treating patients with, for example, chronic, severe, refractory neuropathic pain originating from peripheral nerves or various urinary dysfunctions or still further other indications. Implantable neurostimulation systems may be used to either stimulate a target peripheral nerve or the posterior epidural space of the spine.

Properties of the electrical pulses may be controlled via a controller of the implanted pulse generator. In some exemplary embodiments, these properties may include, for example, the frequency, amplitude, pattern, duration, or other aspects of the electrical pulses. These properties may include, for example, a voltage, a current, or the like. This control of the electrical pulses may include the creation of one or more electrical pulse programs, plans, or patterns, and in some exemplary embodiments, this may include the selection of one or more pre-existing electrical pulse programs, plans, or patterns. In the embodiment depicted in FIG. 3, the implantable neurostimulation system 220 includes a controller in the IPG having one or more pulse programs, plans, or patterns that may be pre-programmed or created as discussed above. In some exemplary embodiments, these same properties associated with the IPG may be used in an EPG of a partly implanted trial system used before implantation of the permanent neurostimulation system 200.

Figure 4:
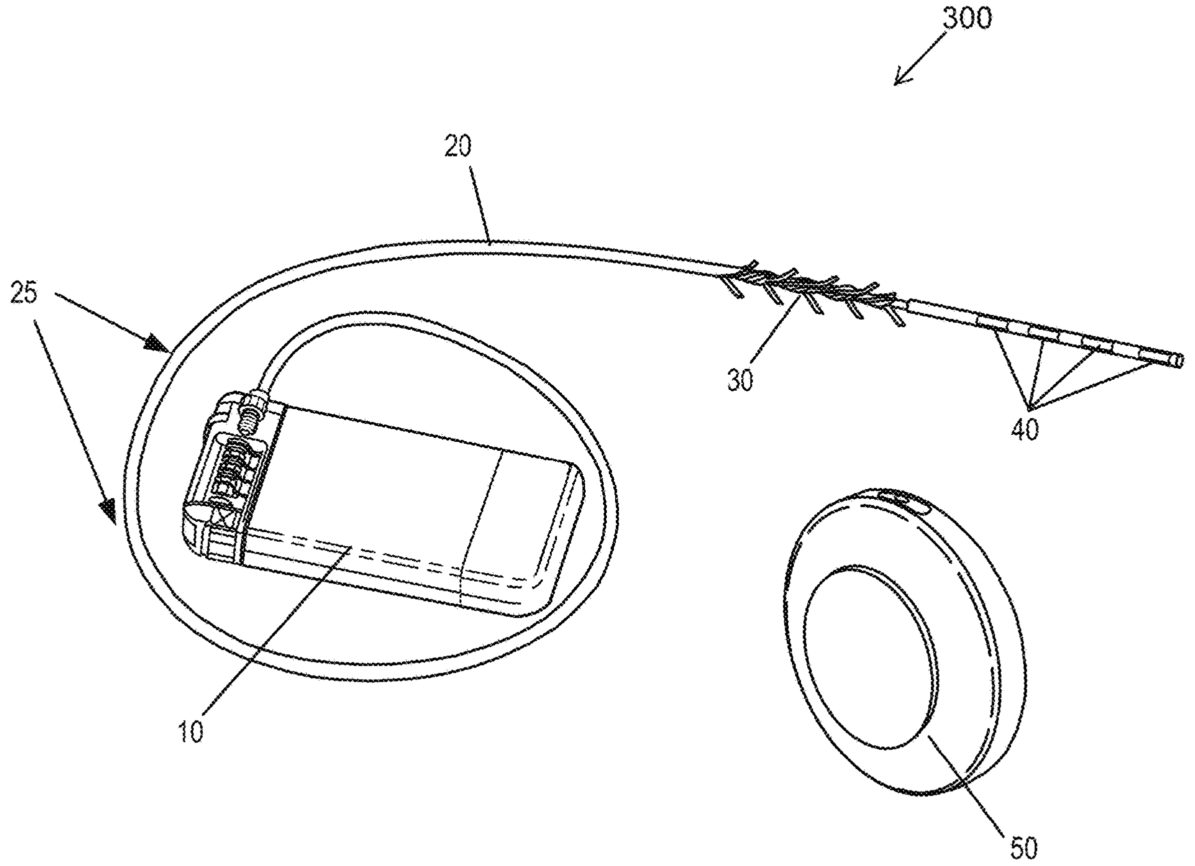
FIG. 4 shows an example of a neurostimulation system having an implantable stimulation lead, an implantable pulse generator, and an external charging device.

FIG. 4 illustrates an example neurostimulation system 300 that is fully implantable and adapted for sacral nerve stimulation treatment. The implantable system 300 includes an IPG 10 that is coupled to a neurostimulation lead 20 that includes a group of neurostimulation electrodes 40 at a distal end of the lead. The lead includes a lead anchor portion 30 with a series of tines extending radially outward so as to anchor the lead and maintain a position of the neurostimulation lead 20 after implantation. The lead 20 may further include one or more radiopaque markers 25 to assist in locating and positioning the lead using visualization techniques such as fluoroscopy. In some exemplary embodiments, the IPG provides monopolar or bipolar electrical pulses that are delivered to the targeted nerves through one or more neurostimulation electrodes. In sacral nerve stimulation, the lead is typically implanted through the S3 foramen as described herein.

The system may further include a patient remote 70 and CP 60, each configured to wirelessly communicate with the implanted IPG, or with the EPG during a trial, as shown in the schematic of the nerve stimulation system in FIG. 1. The CP 60 may be a tablet computer used by the clinician to program the IPG and the EPG. The device also has the capability to record stimulation-induced electromyograms (EMGs) to facilitate lead placement, programming, and/or re-programming. The patient remote may be a battery-operated, portable device that utilizes radio-frequency (RF) signals to communicate with the EPG and IPG and allows the patient to adjust the stimulation levels, check the status of the IPG battery level, and/or to turn the stimulation on or off.

In one aspect, the IPG is rechargeable wirelessly through inductive coupling by use of a charging device 50 (CD), which is a portable device powered by a rechargeable battery to allow patient mobility while charging. The CD is used for transcutaneous charging of the IPG through RF induction. The CD can either be patched to the patient's skin using an adhesive or may be held in place using a belt 53 or by an adhesive patch 52, such as shown in the schematic of FIG. 1. The CD may be charged by plugging the CD directly into an outlet or by placing the CD in a charging dock or station 51 that connects to an AC wall outlet or other power source.

In one aspect, the CD is equipped with one or more communication antennas that allow communication with the IPG. In this embodiment, this communication means is by shortwave radio wave, typically MedRadio. Typically, this communication means (e.g. MedRadio) has been used to communicate with the IPG during a charging session, however, this communication means can also be used to facilitate reprogramming by the remote support entity as the CD is also equipped with another communication means by which the CD can communicate with one more additional external devices. In some exemplary embodiments, this additional communication may include communication to the Patient Device (e.g. by Bluetooth). This configuration allows the CD to communicate with both the IPG and the Patient Device so that the charger may be utilized to establish communication between the Remote Support and IPG for programming, as detailed further below.

Figure 5A:
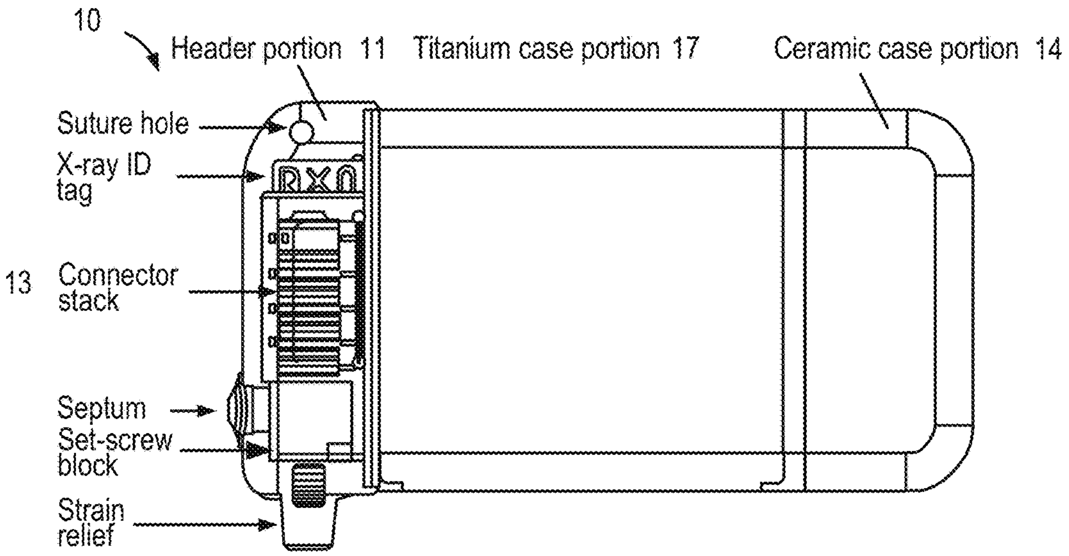
FIGS. 5A-5B show detail views of an implantable pulse generator and associated components for use in a neurostimulation system.
Figure 5B:
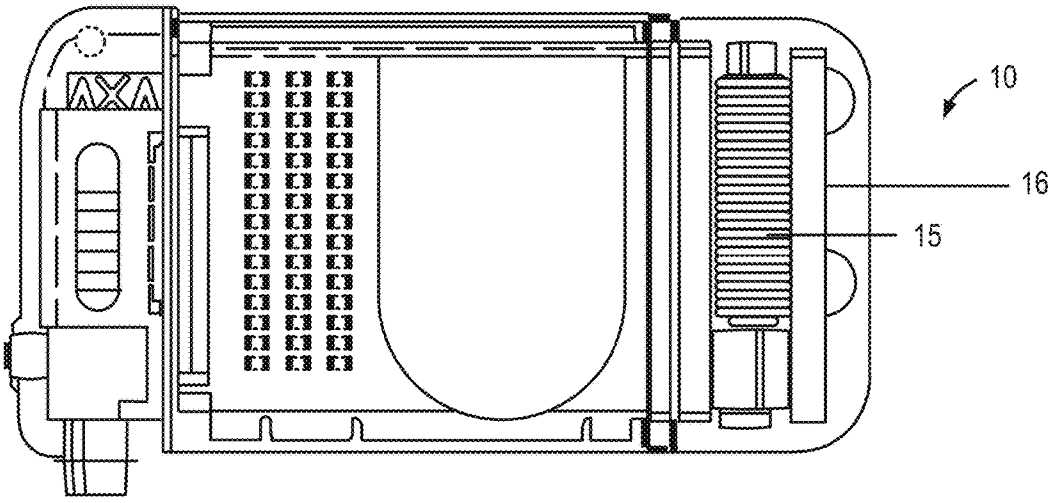

FIG. 5A-5B show detail views of the IPG and its internal components. In some exemplary embodiments, the pulse generator can generate one or more non-ablative electrical pulses that are delivered to a nerve to control pain or cause some other desired effect, for example to inhibit, prevent, or disrupt neural activity for the treatment of OAB or bladder related dysfunction. In some applications, the pulses having a pulse amplitude in a range between 0 mA to 1,000 mA, 0 mA to 100 mA, 0 mA to 50 mA, 0 mA to 25 mA, 0 mA to 12.5 mA and/or any other or intermediate range of amplitudes may be used. One or more of the pulse generators may include a processor and/or memory adapted to provide instructions to and receive information from the other components of the implantable neurostimulation system. The processor may include a microprocessor, such as a commercially available microprocessor from Intel® or Advanced Micro Devices, Inc.®, or the like. An IPG may include an energy storage feature, such as one or more capacitors, one or more batteries, and typically includes a wireless charging unit.

One or more properties of the electrical pulses may be controlled via a controller of the IPG or EPG. In some exemplary embodiments, these properties may include, for example, the frequency, amplitude, pattern, duration, or other aspects of the timing and magnitude of the electrical pulses. These properties can further include, for example, a voltage, a current, or the like. This control of the electrical pulses may include the creation of one or more electrical pulse programs, plans, or patterns, and in some exemplary embodiments, this may include the selection of one or more pre-existing electrical pulse programs, plans, or patterns. In one aspect, the IPG 100 includes a controller having one or more pulse programs, plans, or patterns that may be created and/or pre-programmed. In some exemplary embodiments, the IPG may be programmed to vary stimulation parameters including pulse amplitude in a range from 0 mA to 10 mA, pulse width in a range from 50 μs to 500 μs, pulse frequency in a range from 5 Hz to 250 Hz, stimulation modes (e.g., continuous or cycling), and electrode configuration (e.g., anode, cathode, or off), to achieve the optimal therapeutic outcome specific to the patient. In particular, this allows for an optimal setting to be determined for each patient even though each parameter may vary from person to person.

As shown in FIGS. 5A-5B, the IPG may include a header portion 11 at one end and a ceramic portion 14 at the opposite end. The header portion 11 houses a feed through assembly 12 and connector stack 13, while the ceramic case portion 14 houses an antennae assembly 16 to facilitate wireless communication with the clinician program, the patient remote, and/or charging coil to facilitate wireless charging with the CD. The remainder of the IPG is covered with a titanium case portion 17, which encases the printed circuit board, memory and controller components that facilitate the electrical pulse programs described above. The header portion of the IPG includes a four-pin feed-through assembly 12 that couples with the connector stack 13 in which the proximal end of the lead is coupled. The four pins correspond to the four electrodes of the neurostimulation lead. In some exemplary embodiments, a Balseal® connector block is electrically connected to four platinum iridium alloy feed-through pins which are brazed to an alumina ceramic insulator plate along with a titanium alloy flange. This feed-through assembly is laser seam welded to a titanium-ceramic brazed case to form a complete hermetic housing for the electronics.

In some embodiment, such as that shown in FIG. 5A, the ceramic and titanium brazed case is utilized on one end of the IPG where the ferrite coil and PCB antenna assemblies are positioned. A reliable hermetic seal is provided via a ceramic-to-metal brazing technique. The zirconia ceramic may comprise a 3Y-TZP (3 mol percent Yttria-stabilized tetragonal Zirconia Polycrystals) ceramic, which has a high flexural strength and impact resistance and has been commercially utilized in a number of implantable medical technologies. In one aspect, utilization of ceramic material provides an efficient, radio-frequency-transparent window for wireless communication with the external patient remote and clinician programmer as the communication antenna is housed inside the hermetic ceramic case. This ceramic window has further facilitated miniaturization of the implant while maintaining an efficient, radio-frequency-transparent window for long term and reliable wireless communication between the IPG and external controllers, such as the patient remote and CP. In another aspect, the ferrite core is part of the charging coil assembly 15, shown in FIG. 5B, which is positioned inside the ceramic case 14. The ferrite core concentrates the magnetic field flux through the ceramic case as opposed to the metallic case portion 17. This configuration maximizes coupling efficiency, which reduces the required magnetic field and in turn reduces device heating during charging.

Figure 6A:
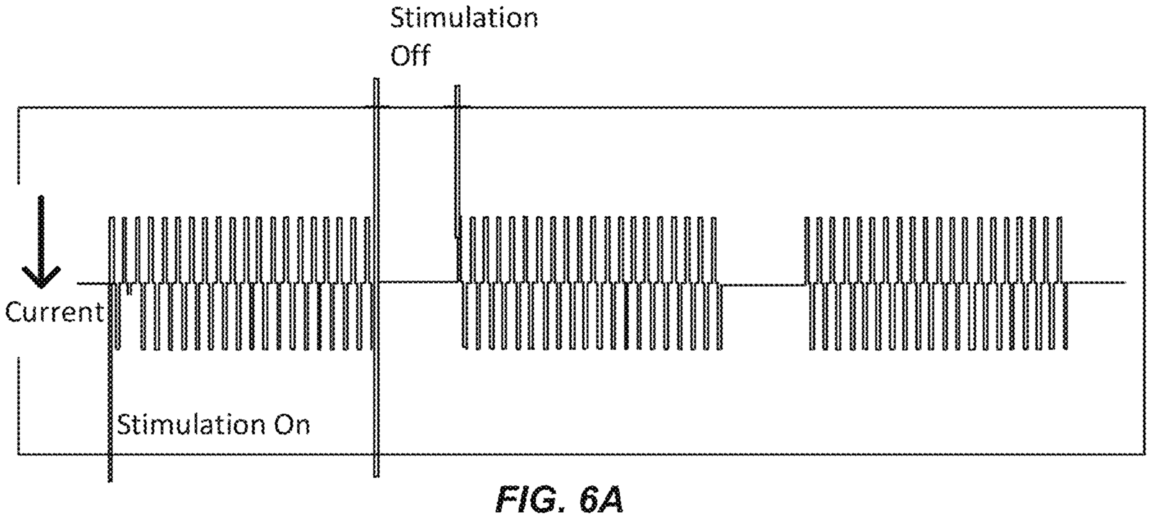
FIGS. 6A-6B show signal characteristics of a neurostimulation program.
Figure 6B:
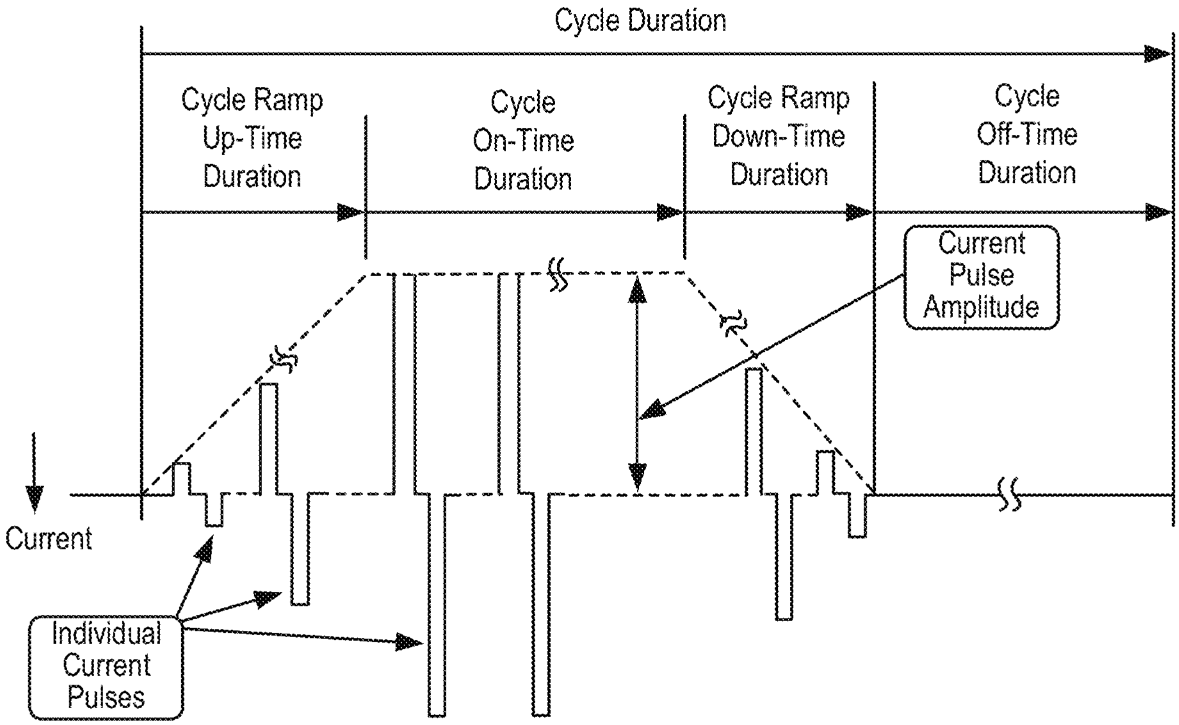

In one aspect, the IPG may be programmed according to various stimulation modes, which may be determined by the CP or selected by the physician using the CP during initial programming or during remote programming. In some exemplary embodiments, the IPG/EPG may be configured with two stimulation modes: continuous mode and cycling mode. The cycling mode saves energy in comparison to the continuous mode, thereby extending the recharge interval of the battery and lifetime of the device. The cycling mode may also help reduce the risk of neural adaptation for some patients. Neural adaptation is a change over time in the responsiveness of the neural system to a constant stimulus. Thus, cycling mode may also mitigate neural adaptation so to provide longer-term therapeutic benefit. FIG. 6A shows an example of stimulation in a cycling mode, in which the duty cycle is the stimulation on time over the stimulation-on time plus the stimulation-off time. In some exemplary embodiments, the IPG/EPG may be configured with a ramping feature, such as shown in the example of FIG. 6B. In these embodiments, the stimulation signal is ramped up and/or down between the stimulation-on and stimulation-off levels. This feature helps reduce the sudden "jolting" or "shocking" sensation that some patients might experience when the stimulation is initially turned on or at the cycle-on phase during the cycling mode. This feature is particularly of benefit for patients who need relatively high stimulation settings and/or for patients who are sensitive to electrical stimulation.

To activate an axon of a nerve fiber, one needs to apply an electric field outside of the axon to create a voltage gradient across its membrane. This may be achieved by pumping charge between the electrodes of a stimulator. Action potentials, which transmit information through the nervous system, are generated when the outside of the nerve is depolarized to a certain threshold, which is determined by the amount of current delivered. To generate continuous action potentials in the axon, this extracellular gradient threshold needs to be reached with the delivery of each stimulation pulse. To activate an axon of a nerve fiber, one needs to apply an electric field outside of the axon to create a voltage gradient across its membrane. This may be achieved by pumping charge between the electrodes of a stimulator. Action potentials, which transmit information through the nervous system, are generated when the outside of the nerve is depolarized to a certain threshold, which is determined by the amount of current delivered. To generate continuous action potentials in the axon, this extracellular gradient threshold needs to be reached with the delivery of each stimulation pulse.

In conventional systems, a constant voltage power source is able to maintain the output voltage of the electrodes, so that enough current is delivered to activate the axon at initial implantation. However, during the first several weeks following implantation, tissue encapsulation around electrodes occurs, which results in an impedance (tissue resistance) increase. According to the ohms' law (I=V/R where I is the current, V the voltage and R the tissue impedance of the electrode pair), current delivered by a constant voltage stimulator will therefore decrease, generating a smaller gradient around the nerve. When the impedance reaches a certain value, extracellular depolarization will go down below the threshold value, so that no more action potential may be generated in the axon. Patients typically need to adjust the voltage of their system to re-adjust the current, and restore the efficacy of the therapy.

In contrast, certain exemplary embodiments utilize a constant current power source. In one aspect, the system uses feedback to adjust the voltage in such a way that the current is maintained regardless of what happens to the impedance (until the compliance limit of the device is reached), so that the gradient field around the nerve is maintained overtime. Using a constant current stimulator keeps delivering the same current that is initially selected regardless the impedance change, for a maintained therapeutic efficacy.

Figure 7:
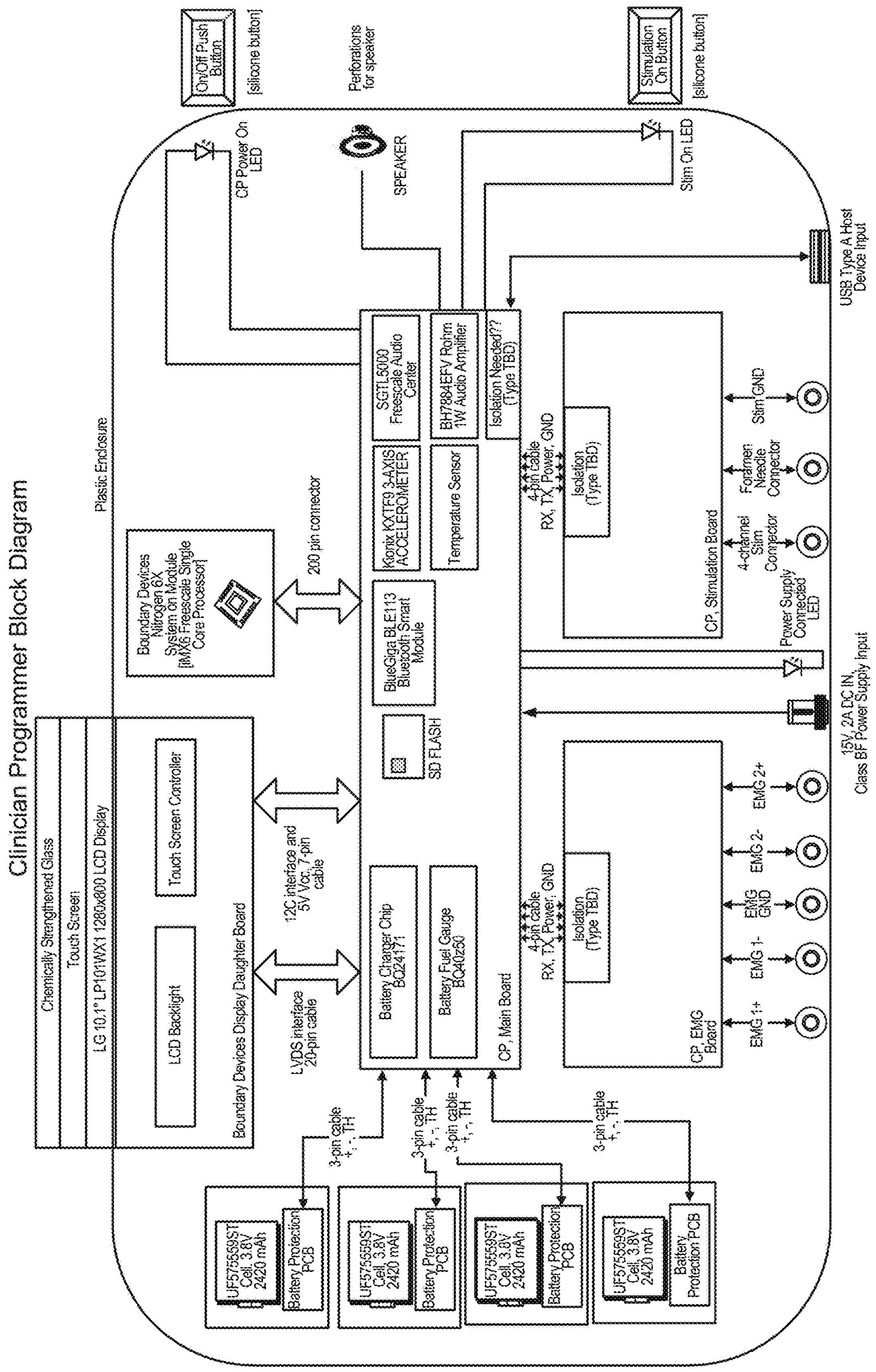
FIG. 7 illustrates a schematic of a clinician programmer configuration.

FIG. 7 schematically illustrates a block diagram of the configuration of the CP 60 and associated interfaces and internal components. As described above, CP 60 is typically a tablet computer with software that runs on a standard operating system. The CP 60 includes a communication module, a stimulation module and an EMG sensing module. The communication module communicates with the IPG and/or EPG in the medical implant communication service frequency band for programming the IPG and/or EPG. While this configuration reflects a portable user interface display device, such as a tablet computer, it is appreciated that the CP may be incorporated into various other types of computing devices, such as a laptop, desktop computer, or a standalone terminal for use in a medical facility.

D. Workflows for Programming and Reprogramming with CP

Figure 8:
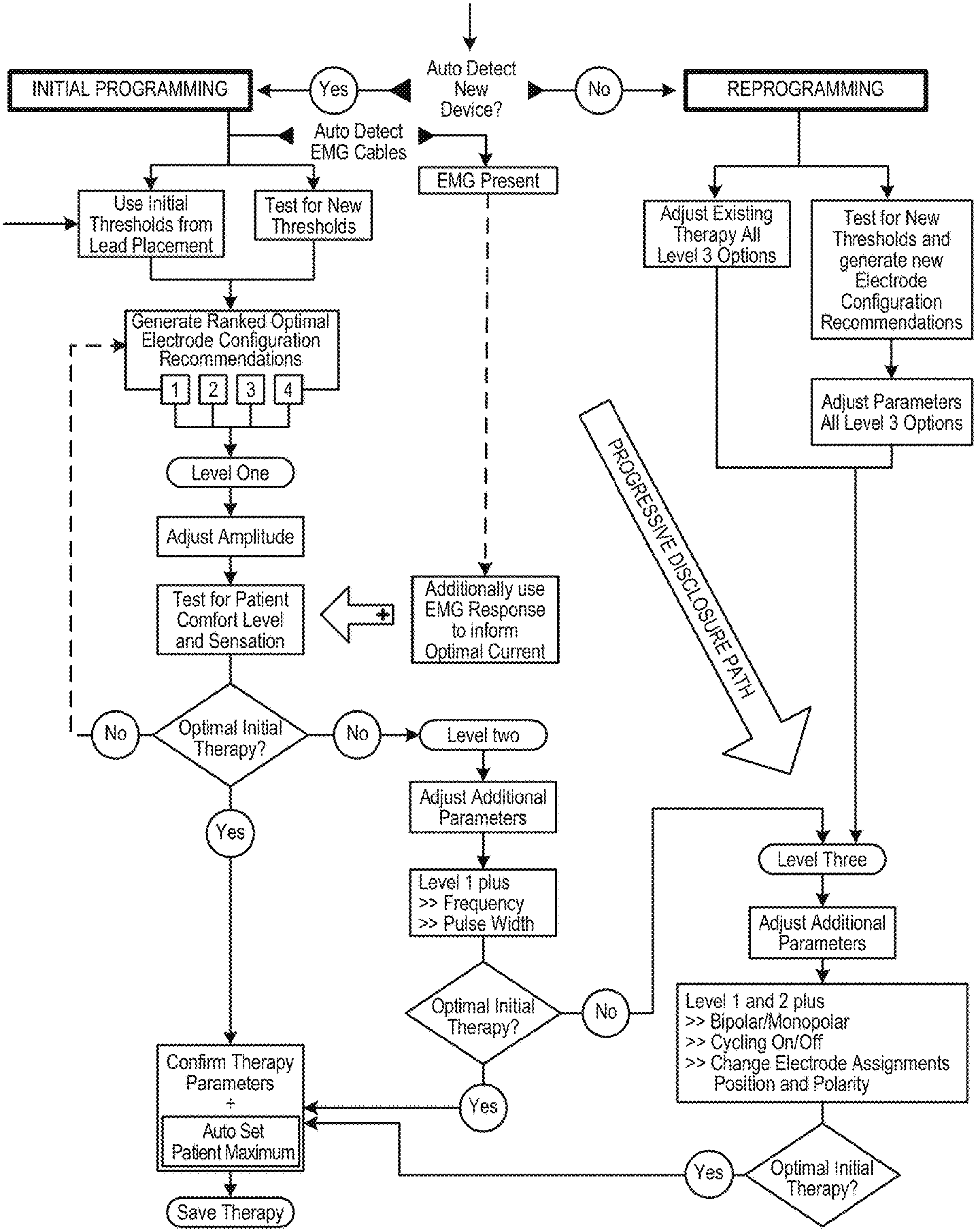
FIGS. 8 and 9 schematically illustrate workflows for using a clinician programmer in programming the implanted neurostimulation system, in accordance with some disclosed embodiments.
Figure 9:
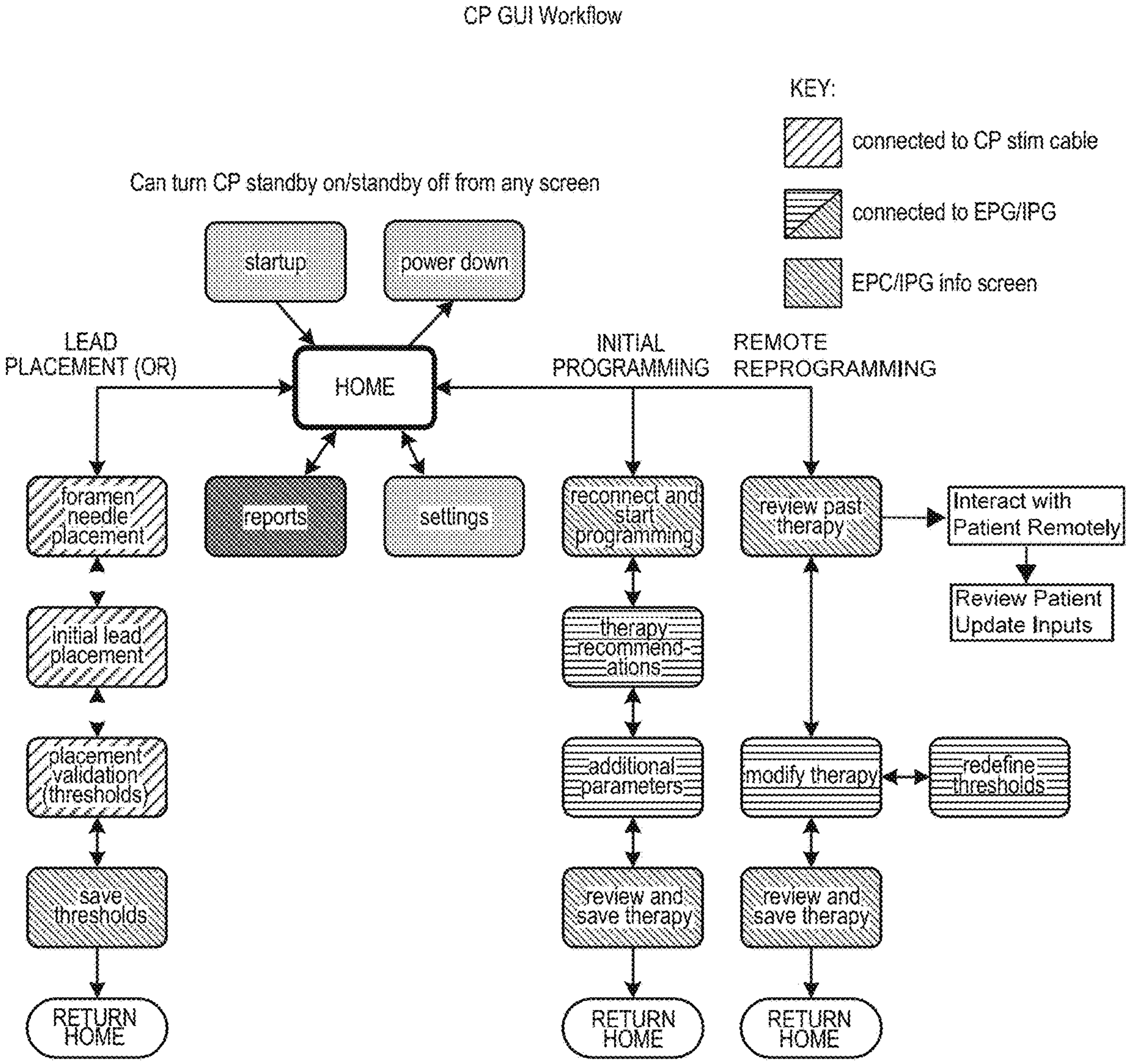

FIGS. 8-9 illustrate schematics of the workflow used in lead placement and programming of the neurostimulation system using a CP with EMG assist. FIG. 8 schematically illustrates a detailed overview of the use of a CP having a graphical user interface for lead placement and subsequent programming, which may include initial programming and reprogramming. FIG. 9 illustrates a CP graphical user interface screen representation schematic of workflow that includes the various setups and connections associated with each step.

III. Neurostimulation Programming

After lead placement and nerve localization, the neurostimulation system is programmed. Typically, programming utilizes stimulation thresholds and/or characterizations of the electrodes, which may be performed specifically for programming or may be performed during the lead placement and subsequently used during programming. Previously determined stimulation thresholds or electrode characterizations may be stored on any of the devices of the system shown, or may be stored on a data center of a first party developer of the system and accessed by the Remote Support or Patient Device during programming or reprogramming. While some programming examples herein describe use of EMG measurements to inform electrode characterization, it is appreciated that these EMG measurements may be stored and subsequently utilized in a reprogramming procedure or that various other approaches without use of EMG may be used, as is known in the art.

In some exemplary embodiments, the system stores the last four programs used onboard a memory of the IPG/EPG. This is particularly advantageous for reprogramming as it allows a physician to access the most recent programs used in the neurostimulation with an entirely different CP that may not otherwise have access to the programming information. In another aspect, the programming data may be accessible online or on a cloud server and associated with a unique identifier of a given IPG/EPG such that a different CP could readily access and download programming information as needed for re-programming.

A. Electrode Characterization

In one aspect, during lead placement, the CP 60 can utilize the thresholds previously recorded in characterizing each electrode as to its suitability for use in neurostimulation. In some exemplary embodiments, the CP 60 may be configured to program the IPG/EPG with an EMG recording from only one muscle, either the anal bellows or the big toe response. Such programming can also utilize a visual observation of the response as well as the recorded maximum response amplitude. In one aspect, the CP 60 performs programming without requiring an anal bellow response observation or EMG waveform measurement of an anal bellows response. In some exemplary embodiments, the CP 60 performs programming using an EMG recording from only the big toe response, such as shown in FIG. 15C in which the graphical user interface of the CP displays patient information 63, which may include information as to the patient's subjective responses to stimulation or treatment. In an alternative embodiment, the CP 60 may be used to program the EPG/IPG using an EMG from only the anal bellows response.

In one aspect, the EMG recording may be that obtained during lead placement, or more typically, obtained during programming so that the patient can provide subjective sensory response data concurrent with performing a big toe response with a given electrode during testing. The programming may further include visual observations of the big toe response and/or the maximum response amplitude obtained during programming. Allowing programming of the IPG/EPG without requiring an anal bellow response is advantageous since the patient is not under general anesthesia while programming is performed and the anal bellows response may be uncomfortable and painful for the patient. This also allows the CP to receive subjective sensory data from the patient during programming as to any discomfort, paresthesia or pain associated with stimulation of a particular electrode configuration.

In one aspect, the EMG recording may be that obtained during lead placement, or more typically, obtained during programming so that the patient can provide subjective sensory response data concurrent with performing a big toe response with a given electrode during testing. The programming may further include visual observations of the big toe response and/or the maximum response amplitude obtained during programming. Allowing programming of the IPG/EPG without requiring an anal bellow response is advantageous since the patient is not under general anesthesia while programming is performed and the anal bellows response may be uncomfortable and painful for the patient. This also allows the CP to receive subjective sensory data from the patient during programming as to any discomfort, paresthesia or pain associated with stimulation of a particular electrode configuration.

B. Electrode Configuration Recommendations

Figure 10:
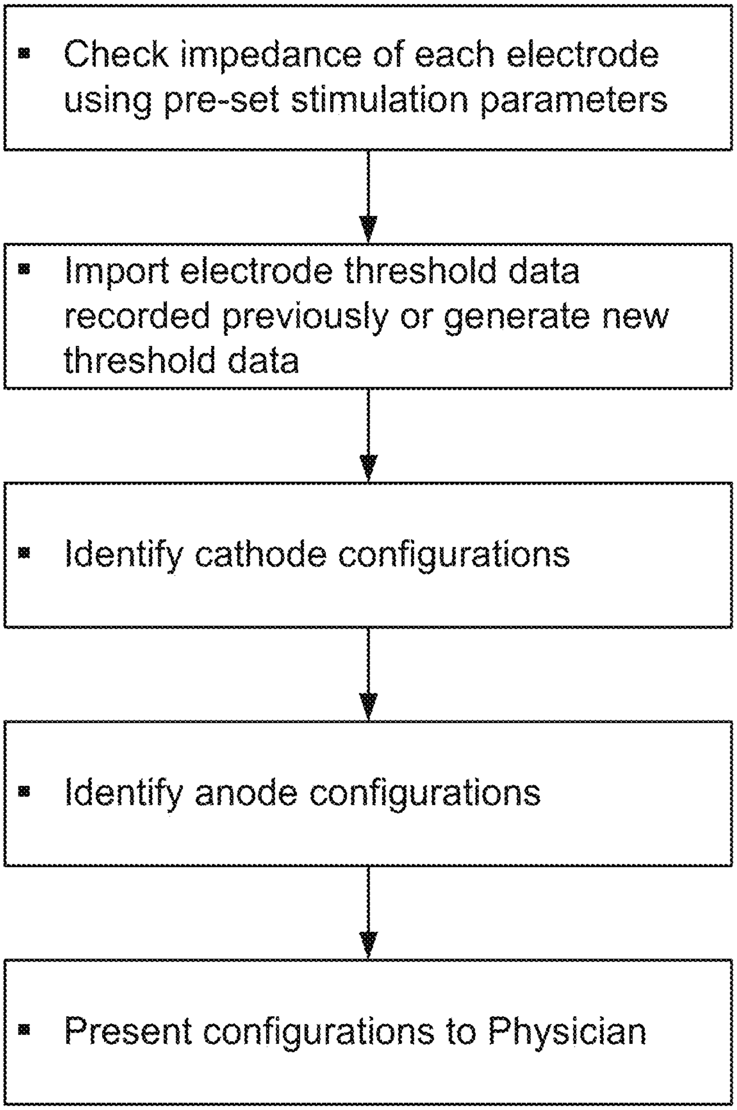
FIG. 10 illustrates an example method by which electrode configuration recommendations are determined and provided to a physician during programming.

In one aspect, the system configuration determines multiple electrode configuration recommendations based on using electrode characterization and/or threshold data based in part patient responses to the electrode stimulations previously obtained (e.g. by EMG or visual observations) and provides the recommendations to the clinician. FIG. 10 illustrates an example method of determining and providing electrode configuration recommendations implemented with a CP. In such methods, the system first checks the impedance of each electrode using pre-set stimulation parameters and may lock out any electrode with unacceptable impedance (<50 or >3,000 Ohms) from being assigned as an anode or cathode. The system then identifies threshold data associated with each electrode, either from data recorded previously during lead placement or by generating new threshold data. The system tiers the electrodes based on the threshold values (e.g. "good," "ok," "bad") and rank the electrodes within each tier. Any electrodes that result in an unpleasant sensation are excluded from being used as a cathode. The system then determines multiple electrode configuration recommendation, preferably at least four differing configurations, according to pre-determined rules and are then presented to the clinician using the CP.

In one aspect, the electrode configurations are determined based on the threshold data according to the following rules: (1) Assign single cathode configurations for each contact in the "Good" tier, prioritized from farthest pair to closest pair; (2) Assign single cathode configurations for each contact in the "Good" tier, prioritized from lowest to highest threshold; (3) Assign double cathode configurations for each pair of adjacent electrodes in "Good" tier, prioritized by lowest combined threshold; (4) Assign single cathode configurations for each contact in the "OK" tier, prioritized from lowest to highest threshold; and (5) Assign double cathode configurations for each pair of adjacent electrodes from "Good" and "OK" tiers, prioritized by lowest combined threshold. The anodes for the cathode configurations are assigned as follows: for monopolar configuration, the IPG housing or "can" is assigned as the anode; for bipolar configuration, the electrode furthest from the cathode with acceptable impedance is assigned as the anode.

Figure 11:
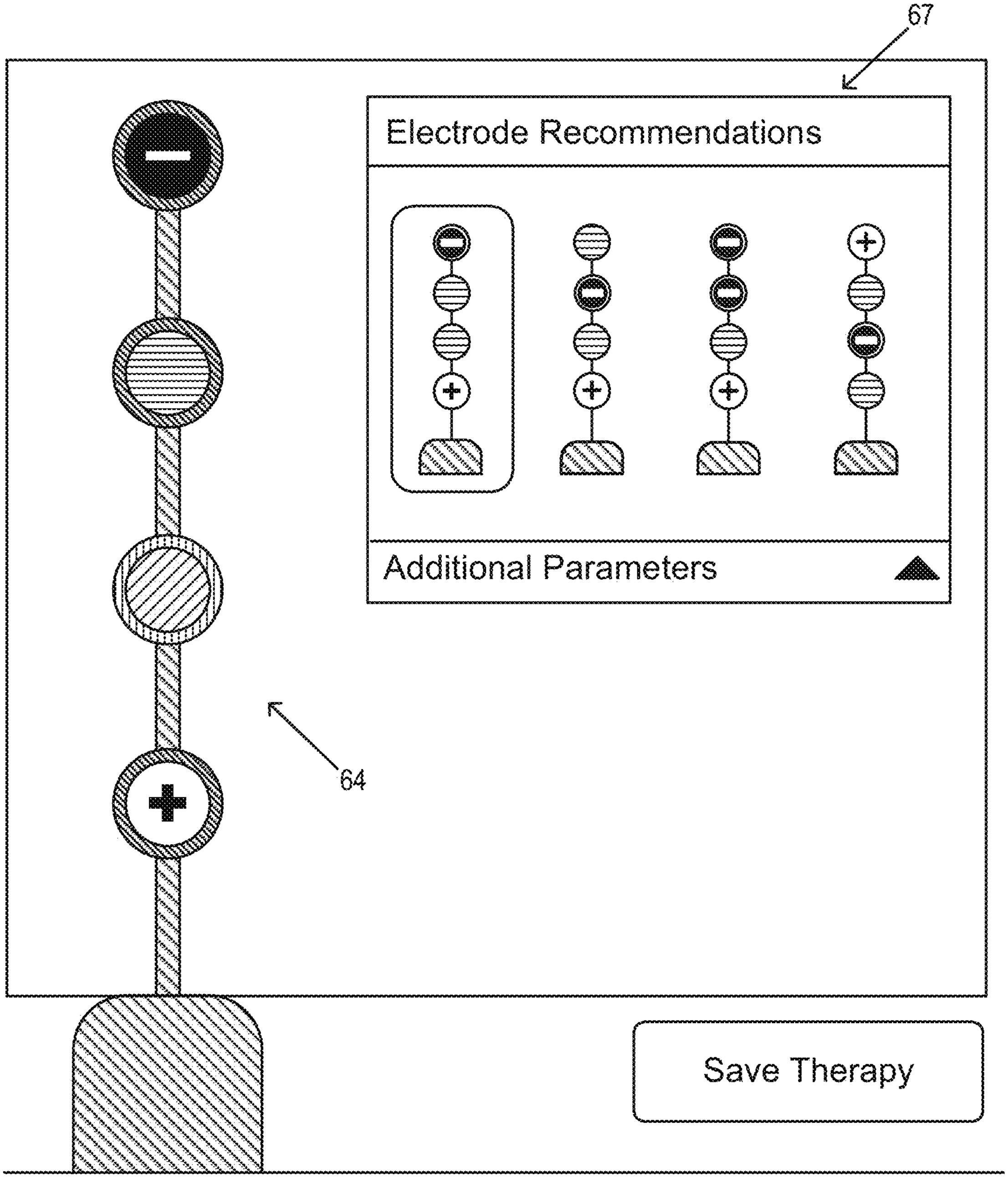
FIG. 11 illustrates an example electrode configuration recommendation for display on a clinician programmer during programming and/or reprogramming of a neurostimulation system.

After identification of the electrode configuration recommendations, the system presents the electrode configuration recommendations to the physician, typically on a user interface of the CP such as shown in FIG. 11, on which the physician may select any of the electrode configurations for testing, modify a recommended electrode configuration as desired, or create a new electrode configuration. In one aspect, the system presents the electrode configuration recommendations within a selectable menu and may include one or more default values or attributes for a given electrode recommendation.

In one aspect, in an idealized setting in which each of the electrodes has a "good" impedance, the system simply recommends each of the contacts as a single cathode. Although it is desirable to have four "good" electrodes, it is acceptable to have at least three "good" electrodes for initial programming. The above algorithm recommends the best electrode selection for a given case. While each physician may have their own way to select electrode for programming, providing a set of electrode configuration recommendations that are easily viewed and selected by the physician helps standardize the process, reduce the duration of the procedure and provide improve patient outcomes, particularly for inexperienced implanters or minimally trained personnel.

In one aspect, the above algorithm assumes a single input parameter for the electrode threshold. In some exemplary embodiments, the system allows the physician to select, through the CP, what parameter(s) (sensory or motor responses or in combination) to use to determine the threshold for each electrode. The physician can also select whether to rely on EMG feedback previously obtained for threshold determinations. In another aspect, qualitative sensory feedback will be considered in electrode selection, e.g., if a patient reports unpleasant sensation for any specific electrode, this electrode will be excluded from being used as cathode. In another aspect, the algorithm prioritizes single cathode over double cathodes for all contacts in the "good" tier. In some exemplary embodiments, the electrodes are tiered according to the following tiers: "good"="1-3 mA"; "ok"="0.5-1 mA" and "3-4 mA"; "bad"="<0.5 mA" and ">4 mA."

FIGS. 12A-12B depict case studies illustrating selection of four electrode recommendations for a bipolar and monopolar treatment according to the algorithms described above for each case 1 in FIG. 12A and case 2 in FIG. 12B.

C. Program Selection, Modification and Testing

In programming the neurostimulation system, an EMG signal may be used to evaluate programming quality by allowing user to see if a motor response is evoked by stimulation. In some exemplary embodiments, the user can manually observe EMG responses and enter the observations into the CP and try to set a stimulation amplitude at a level that evokes a desired motor response.

Figure 13A:
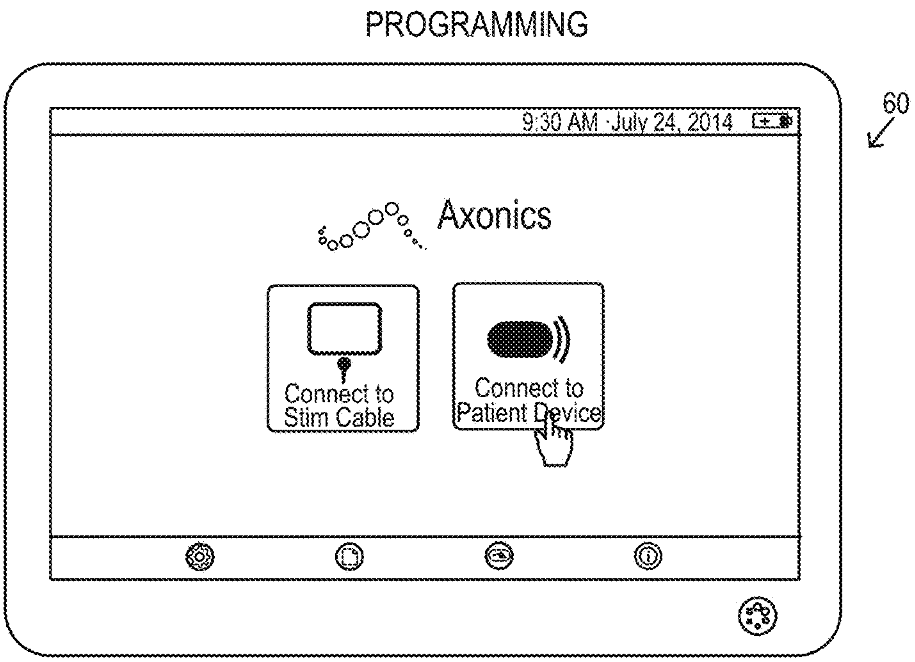
FIGS. 13A-13K illustrate a graphical user interface display of a clinician programmer during a programming procedure.
Figure 13B:
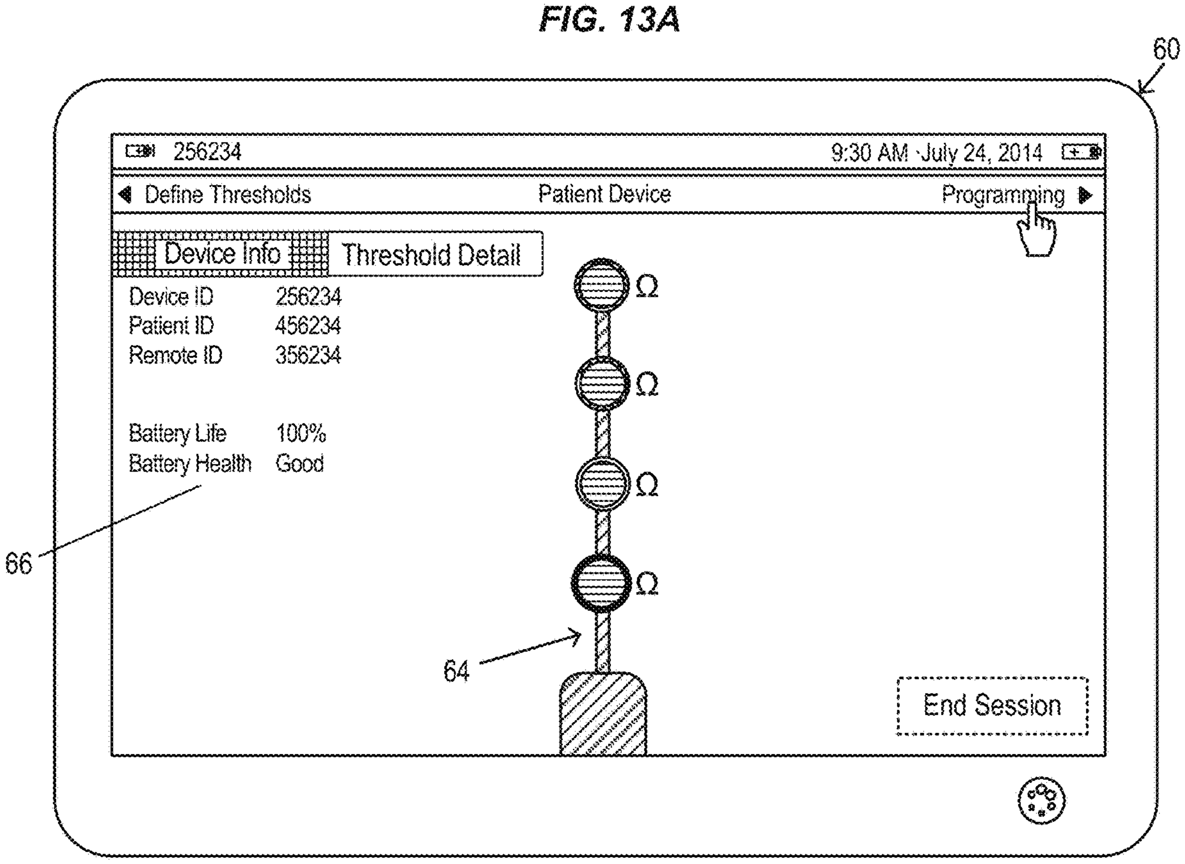

FIGS. 13A-13K illustrate the graphical user interface of the CP during initial programming and testing, although it is appreciated that various aspects are applicable to reprogramming as well. FIG. 13A depicts the CP 60 re-connecting with the patient device and verifying the device info. The physician can confirm this by viewing the device info display 66 shown in FIG. 13B before proceeding with programming. FIG. 13B is the IPG data display which shows the threshold summary and contact status. The threshold data from "lead placement" will be recorded and may be viewed in summary form on this page. Symbols to right of each contact represent the impedance associated with that contact: Green ("good"): 50-3,000 Ohms, Red ("bad"): <50 or >3,000 Ohms. In some exemplary embodiments, yellow may indicate "marginal," while in other embodiments there will not be a yellow option. The colored circles around each contact represent the qualitative assessment of that contact from lead placement. It is a summary of the information in the "threshold detail" tab. As shown in FIG. 13B, electrodes #0 and #1 are shown in green, electrode #2 is shown as orange, and electrode #3 is shown as red. In one aspect, the CP 60 can program the IPG/EPG without by utilizing EMG waveforms and/or visual response and patient sensory data obtained by the CP 60 during lead placement. Programming may also utilize additional patient information (e.g. subjective input as to sensory perception) obtained from the patient during programming.

Figure 13C:
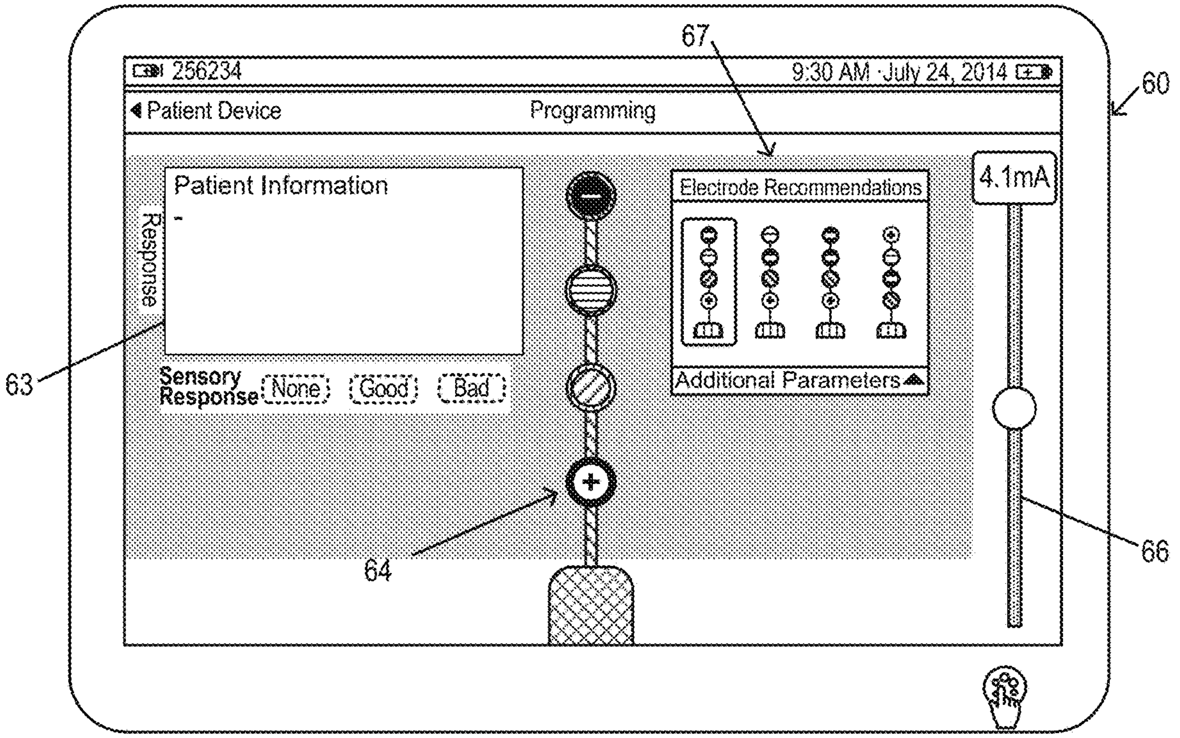

FIG. 13C illustrates programming of the IPG and testing of the first electrode configuration recommendation shown on display 67, which shows four electrode configuration recommendations determined according to the algorithms discussed above. The electrode configuration recommendations are based off input from the Threshold Detail determined during lead placement characterization. It is appreciated that the electrode thresholds could also be determined during programming. Colored circles around each contact represent the qualitative assessment of that contact from lead placement. It is a summary of the information in the "threshold detail" tab. The presence of motor response and quality of the sensory response is manually recorded for retrospective data analysis purposes. The amplitude adjustment may be done in an auto-adjusting increments or fixed increments as discussed previously.

Figure 13D:
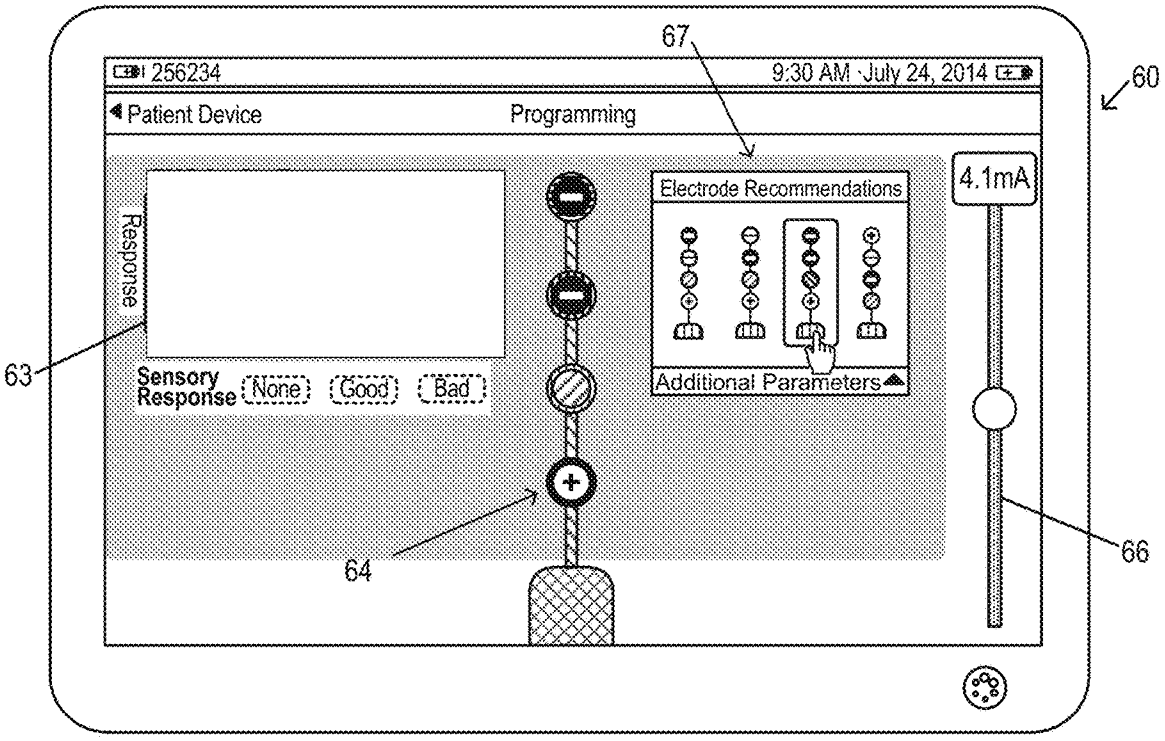

In the first electrode configuration recommendation in FIG. 13C, the lead operates in a bi-polar mode between electrodes 0 and 3, electrode #0 acting as the cathode and electrode #3 acting as the anode. The same procedure is repeated for each of the four electrode recommendations, as shown in FIG. 13D, in which a double cathode configuration is being tested.

Figure 13E:
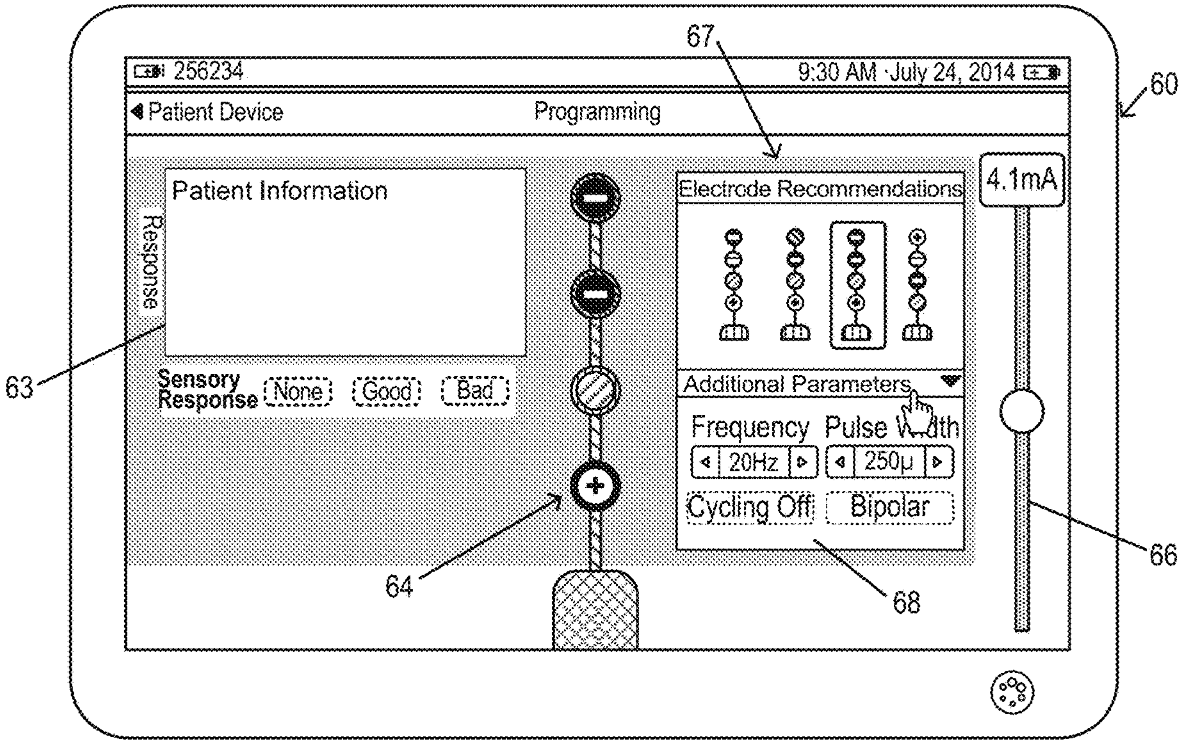
Figure 13F:
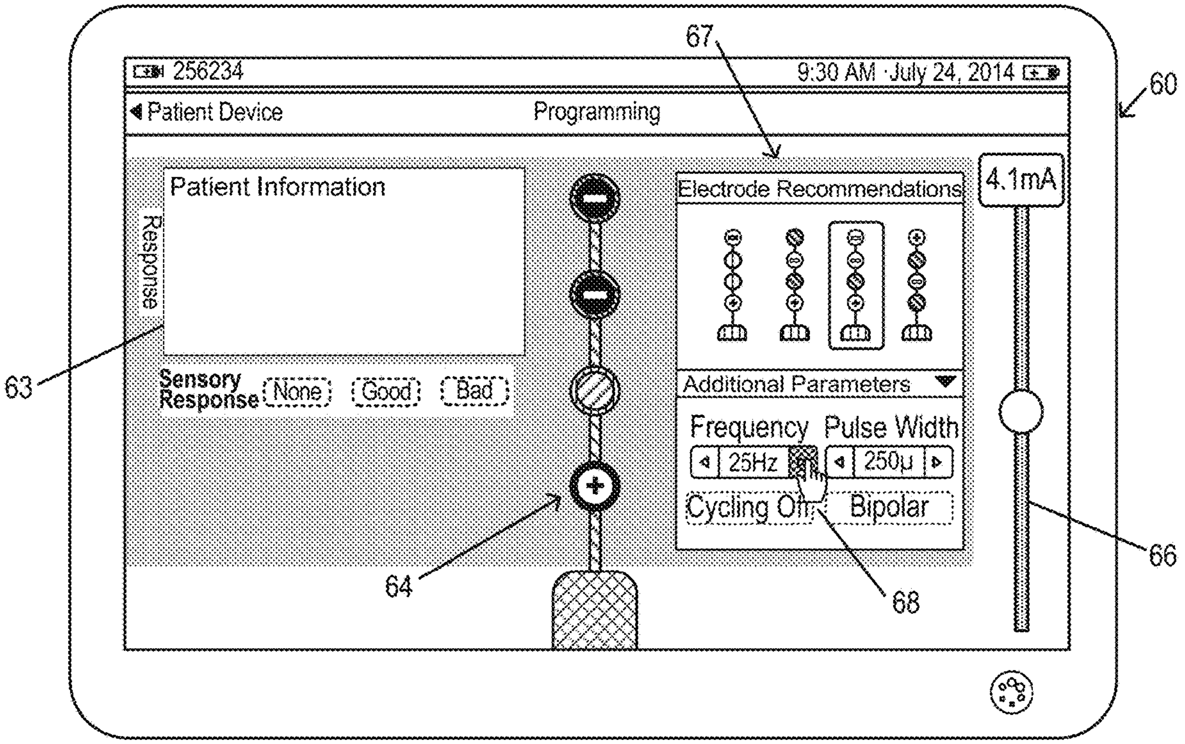
Figure 13G:
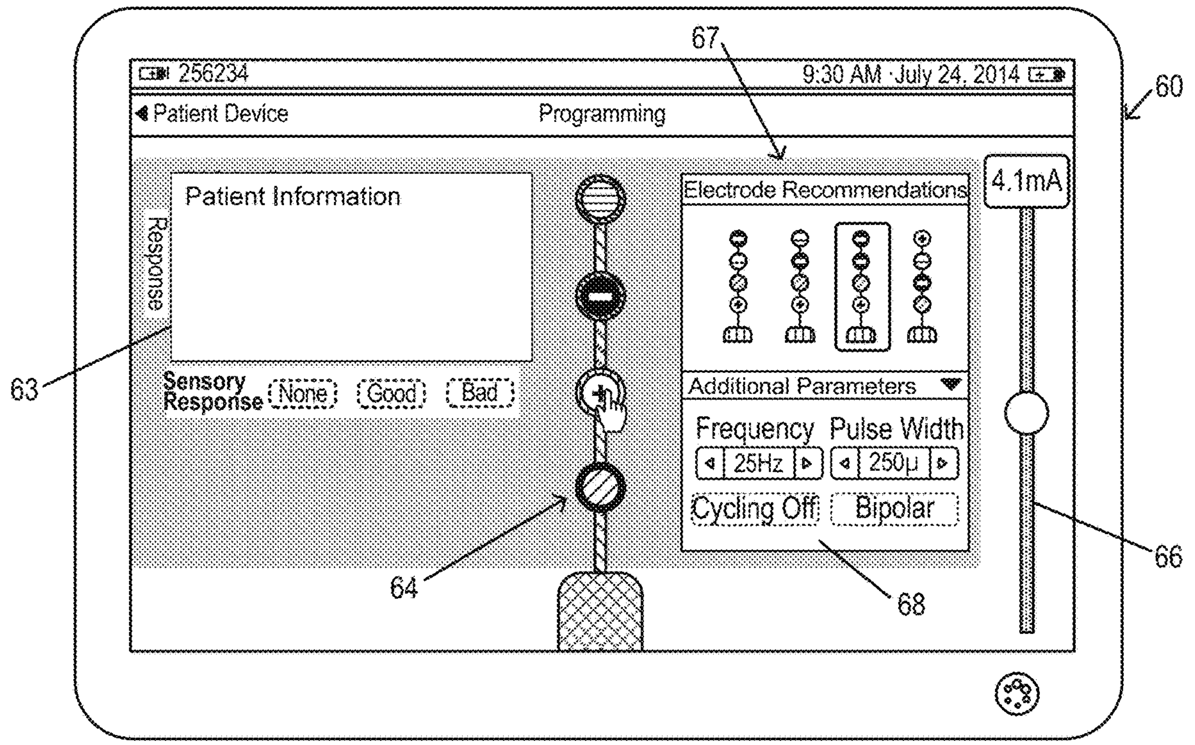
Figure 13H:
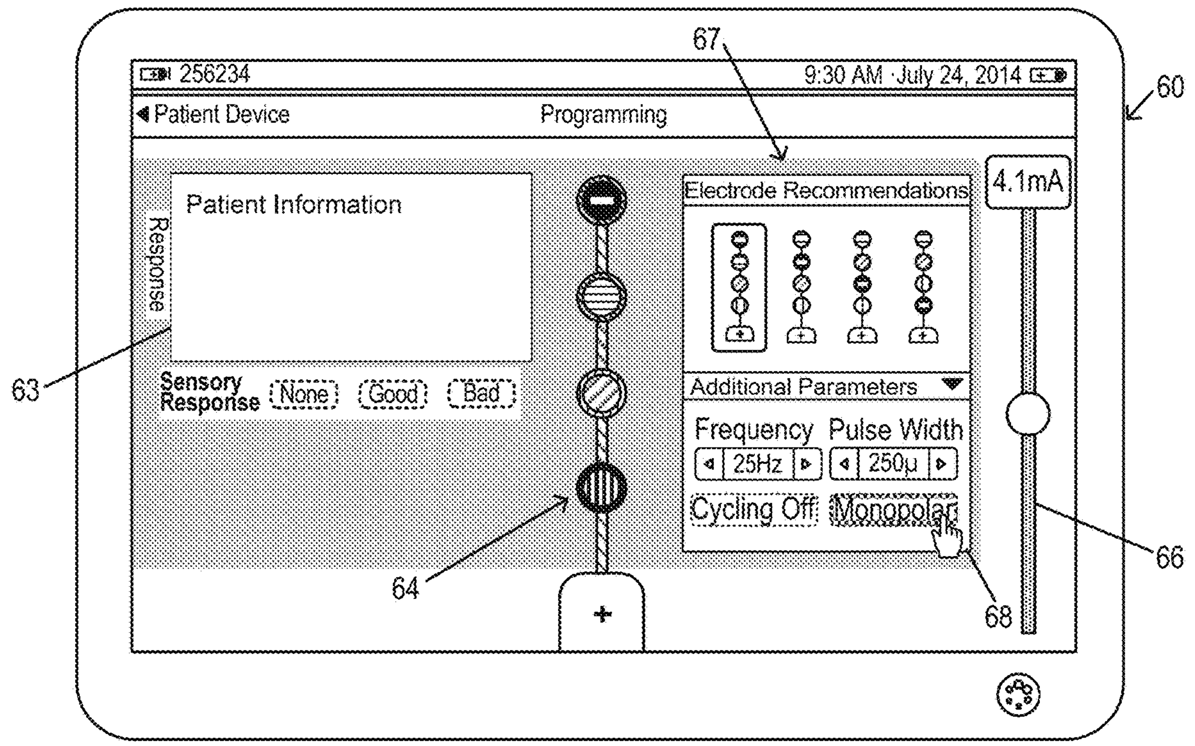
Figure 13I:
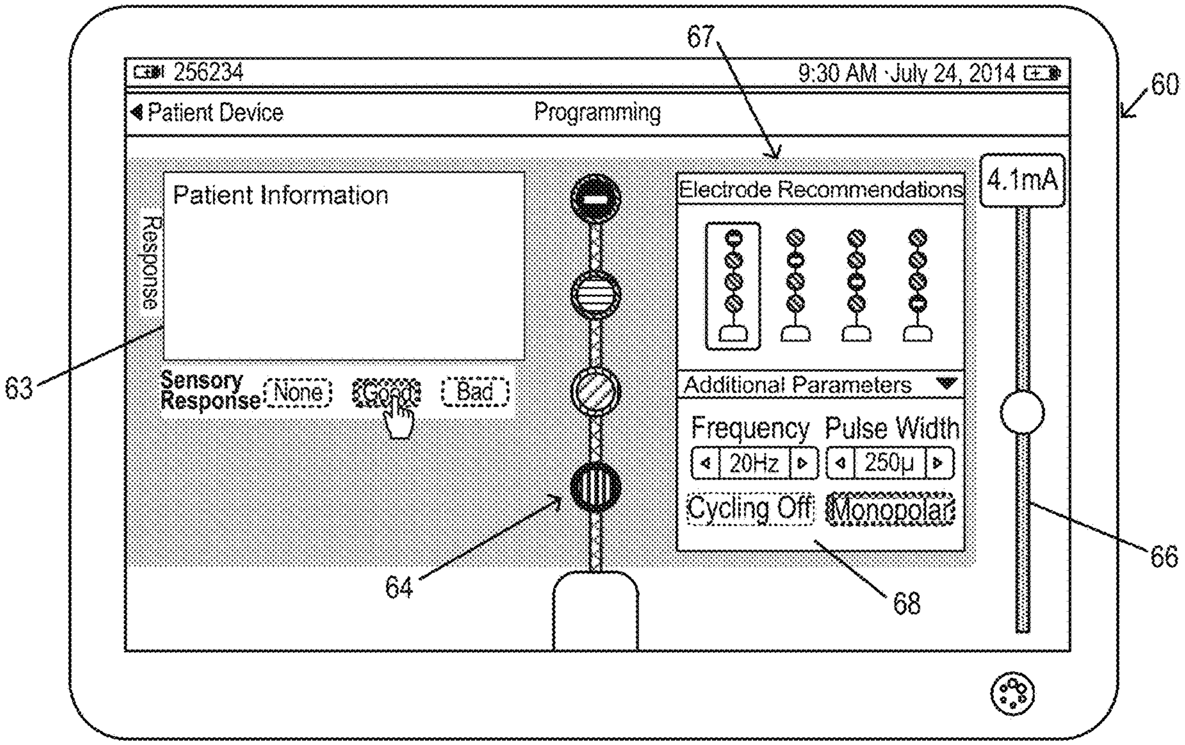
Figure 13J:
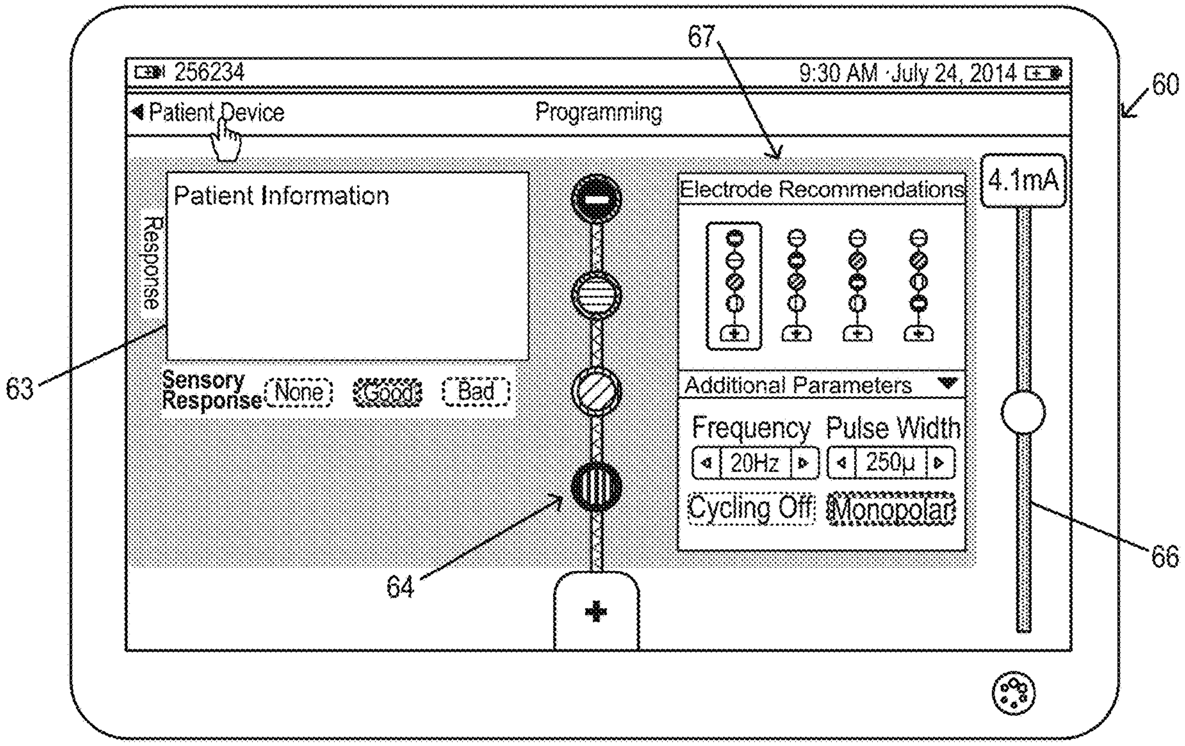
Figure 13K:
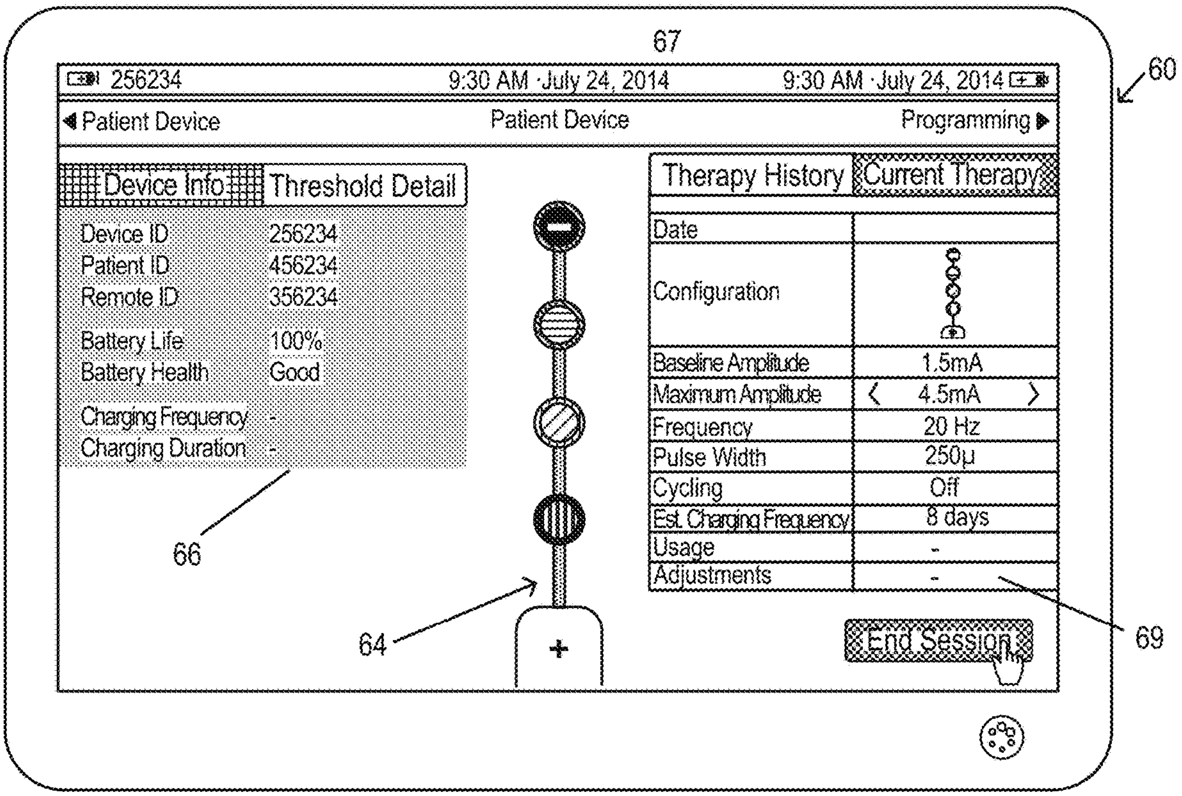

In one aspect, the graphical user interface allows the user to adjust various parameters associated with each of the recommended electrode configurations being tested. For example, as shown in FIG. 13E, the graphical user interface of the CP 60 includes an Additional Parameters display 68 in which the physician select and adjust various parameters (e.g. Frequency, Pulse Width, Cycling and Mode) associated with each electrode configuration as needed for a particular therapy and/or patient. After adjustment, the patient and program information may be updated and recorded in the CP 60. In another aspect, the physician may re-assign the electrode polarity associated with a given electrode configuration recommendation using the CP, such as shown in FIG. 13G, in which the cursor may be used to change the electrode polarity on the electrode status display 64. In yet another aspect, the user may switch between bipolar and mono-polar modes by selecting the Mode button in the Additional Parameters display 68. Upon selection of monopolar mode, the CP 60 will display multiple mono-polar electrode configuration recommendations, as shown in FIG. 13H. When the physician is satisfied with the electrode configuration settings, the physician may proceed to save the settings in the CP 60 by selecting the Patient Device menu, as shown in FIG. 13J, confirming the therapy settings, such as viewing the Current Therapy display 69 shown in FIG. 13K, and saving the therapy to the Patient Device, after which the IPG/EPG are fully programmed and the CP 60 may be detached.

In one aspect, after programming of the IPG/EPG in accordance with the above described methods, the patient evaluates the selected program over a pre-determined period of time. Typically, the patient is able to make limited adjustments to the program, such as increasing or decreasing the amplitude or turning the treatment off If after the assessment period, the patient has not experienced relief from the treated condition or if other problems develop, the patient returns to the physician and a re-programming of the IPG/EPG is conducted with the CP in a process similar to the programming methods described above, to select an alternative electrode configuration from the recommended configuration or to develop a new treatment program that provides effective treatment.

V. Remote Programming

In one aspect, the methods and devices detailed throughout facilitate programming of the IPG remotely. As described herein "reprogramming" merely refers to a programming operation that occurs after initial programming and can encompass determining an entirely new program or troubleshooting of a current therapy program by modifying one or more therapy parameters remotely. Reprogramming can utilize some information obtained previously during lead placement or initial programming, or can repeat the programming procedure or utilize an alternative programming procedure. In some exemplary embodiments, the programming procedure may utilize algorithms or rules to determine a suitable therapy program from known parameters. In other embodiments, the programming procedure may include the clinician applying or adjusting parameters accordingly to their preferences. It is appreciated that any aspects of programming procedures described herein are applicable to remote reprogramming as well.

A. Patient Interface/Session Initiation

In one scenario, after a patient is implanted with a neurostimulation lead and an implantable pulse generator, the patient may experience unsatisfactory therapy due to lack of efficacy or discomfort with stimulation and desire reprogramming. Various aspects of the process by which reprogramming may be effected or informed are detailed below.

In some exemplary embodiments, the patient completes a bladder or bowel diary included on a "Patient App" installed on a Patient Device (e.g. smartphone) in order to "qualify" or enable the Remote Programming function. The integrated symptom diary (bladder and/or bowel diary) allows the patient to keep a diary of their symptoms for a period of time prior to the initial assessment of suitability of the device and prior to requesting and in the period immediately after a reprogramming session. In some exemplary embodiments, programming technicians can access this information remotely in order to assess programming need. Alternatively, the diary function could be performed on various other devices, such as a tablet, laptop or desktop computer.

In some exemplary embodiments, the patient places the Charger over the IPG and charging communicates with the Patient App on the Patient Device. In some exemplary embodiments, the Charger to IPG communication is MedRadio, while the charger to Patient App communication is Bluetooth. In other embodiments, the system utilizes the Patient Remote, which communicates with IPG via MedRadio and connects to the Patient App of the Patient Device via Bluetooth.

In some exemplary embodiments, the Patient App on the Patient Device (e.g. smartphone) communicates via Wifi to the Remote Programming Service. Typically, the Patient App may be configured to utilize Bluetooth (e.g., to Charger) and Wifi capabilities. In some exemplary embodiments, Voice over Internet Protocol (VoIP) technology may be incorporated into the Patient App in order to avoid the need for a standard voice call, for example by using Skype integration. In other embodiments, the system can utilize a specialized, dedicated intermediary communication device that communicates with IPG via MedRadio and connects via Bluetooth to the Patient Device. In still other embodiments, the system can utilize a specialized Patient Device that communicates with IPG via MedRadio and connects by Wifi to the Remote Programming Service.

B. Remote Programming Function

In another aspect, the Patient App of the Patient Device may be configured to communicate via Wifi to the Remote Programming "Back-end". In some exemplary embodiments, the communication includes a data connection plus a Voice or Video chat connection between Patient and Programming Technician. The back-end components may be deployed in a number of ways, including any of cloud based, a local server, or a hosted server. The communication may include any of the following aspects: program information (e.g. current therapy, electrode characterizations, stimulation thresholds) and patient information (e.g. account, profile information, a symptom information diary from the patient).

In another aspect, the reprogramming procedure can utilize a Physician App or a Remote Programming App (these terms are used interchangeable throughout), which may be a mobile/web app that is served to a browser. This approach provides the greatest flexibility and scalability. This approach further provide versatility between several options for the structure of the support team, for example, any of a virtual call center with technicians of the device provider, a team of technicians in a call center, and a virtual call center team of contracted clinicians (e.g., super user, expert nurses, or physicians). In some exemplary embodiments, the application may be configured to provide direct contact from a patient to their own chosen physician/clinician, which may be preferable for those clinicians who want to keep control of the entire process. In some exemplary embodiments, the Patient App is not accessible through a browser and must be installed on the patient's portable device (e.g. smartphone, tablet).

In another aspect, the Remote Programming App syncs to additional databases as necessary. These additional database may include a Patient Care Manager (PCM), which allows a support technician to see relevant patient therapy history. In some exemplary embodiments, the patient's recent therapy history may be pulled from the IPG by the Charger or Patient Remote and shared via the Patient App connection to the Remote Programming App. Thus, the Patient App and Remote Programming App create an application framework by which the patient and remote support can interact, as well as communicate information access through any of the subject devices. In one aspect, this framework allows the remote support authorization and permissions over the implanted pulse generator beyond those of the patient in order to enable the remote support to control and/or adjust the implanted pulse generator for purposes of programming.

C. Remote Programming Process (Patient/Tech Interaction)

The system applications are configured so that a technician receives a communication (e.g. "call"), typically initiated via the Patient App, from a patient who wishes to have their device settings adjusted remotely. In some exemplary embodiments, the remote support can then access the patient's history stored in the patient database (e.g., Patient Care Manager), and can discuss the patient's needs live with them by voice or video call conducted through the application framework. In some exemplary embodiments, the technician sends new settings to the patient's IPG via the patient's own mobile device during the call session. In some exemplary embodiments, any setting, except amplitude, may be adjusted remotely. In some exemplary embodiments, patient must increase amplitude on their Patient Remote, which minimizes the risk of unintended stimulation/discomfort.

In another aspect, the patient gives explicit permission via the Patient App user interface for settings changes to be transferred to the stimulator, or grants permission to the remote support to make changes to the IPG in real-time. In some exemplary embodiments, the patient increases amplitude using their Patient Remote and describes any resulting change in sensation or discomfort to the technician, who adjusts settings in response. In some exemplary embodiments, the Patient Remote has access to the full amplitude range (just as when programming with the CP) and, if using the Charger as the communication bridge from the IPG to the Smartphone, communicates with the IPG while the Charger is also connected. In some exemplary embodiments, upon completion of programming activity, either the technician or patient can disconnect programming connection via the Patient App or Remote Programming App.

D. Clinician Interface

In another aspect, the system utilizes a remote device, which may be a CP as well as a standard computing device (e.g. smartphone, tablet, laptop, desktop). A standard computing device may be configured to facilitate remote programming by use of a Remote Programming App. In some exemplary embodiments, the Remote Programming App may be a web app accessed using a standard browser. In some exemplary embodiments, physicians can access a report of Remote Programming activities to see logs/reports on Remote Programming sessions for their patients. In some exemplary embodiments, the Patient App can only be installed on the patient's personal computing device and is not accessible through a browser.

E. Remote Programming Systems Examples

The above-noted aspect of the remote reprogramming process may be further understood by referring to FIGS. 14-20.

Figure 14:
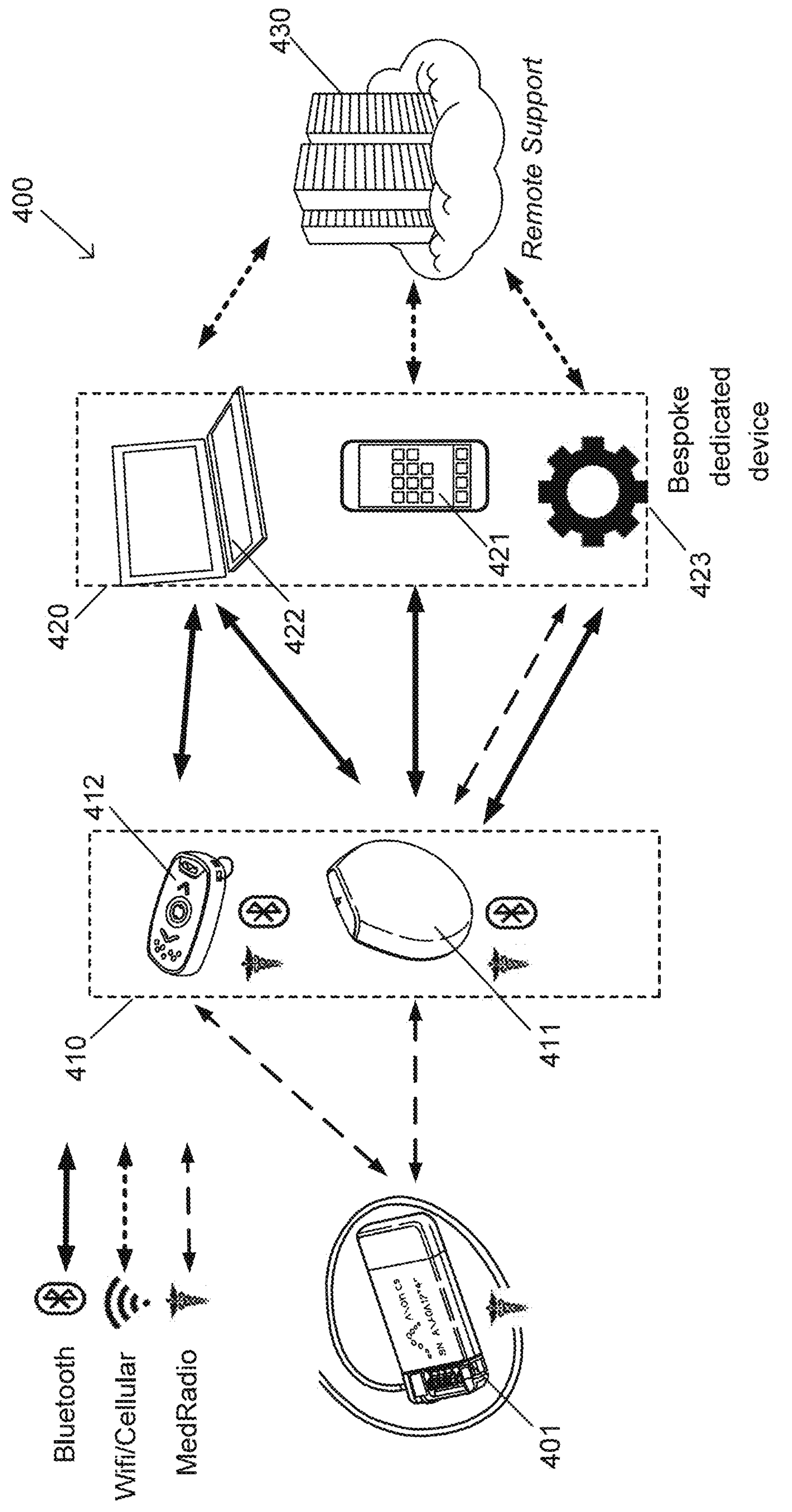
FIG. 14 schematically illustrates a remote programming system, in accordance with some exemplary embodiments.

FIG. 14 schematically illustrates a remote programming system 400, in accordance with some exemplary embodiments. The remote programming system includes the IPG 401 that communicates with Remote Support 430 through local intermediary devices 410, 420, which may include any of a Patient Remote 411, Charger 412, a laptop 422, smartphone 421 or a specialized dedicated reprogramming device 423. Typically, the communication path entails the IPG communicating with a first intermediary device 410, which in turn, communicates with a Patient Device 420, which in turn communicates with Remote Support 430. In this embodiment, the first intermediary device may be a Charger 411 or Patient Remote 412, and the Patient Device 420 may be a smartphone 421, laptop 422 or a specialized dedicated programmer device 423. Preferably, the communication system includes the IPG 401, Charger 411, Smartphone 421 and Remote Support 430, which is advantageous since the Charger is readily rechargeable and the use of a Smartphone provides greater versatility and mobility and does not require additional specialized equipment. It is appreciated that the remote programming procedure can utilize any combination of the devices and communication paths depicted.

In one aspect, local communication between local devices can utilize shortwave radio communication, for example MedRadio or Bluetooth. In this embodiment, the communication between the IPG 401 and Remote Support 430 may be effected through a number of alternative communication paths and differing types of communication (as indicated by the dashed and solid lines). The IPG 401 communicates by MedRadio, typically to comply with regulatory requirements, such that the Patient Remote 412 and Charger 411 are well suited for use as intermediary devices since each is already equipped to communicate with the IPG by MedRadio. Each of the Patient Remote and Charger can also be configured to communicate by Bluetooth such that either may be used to facilitate interaction with the patient through Patient Device 420. In this approach, the patient's personal computing device may be configured for remote programming by use of a Patient App, which is a specialized executable application program stored on a memory of the patient device. The Patient App establishes a framework by which the patient can input subjective information regarding their treatment and interact with the Remote Support entity to facilitate reprogramming and securely send program information for purposes of remote programming. In some exemplary embodiments, the system can utilize a specialized dedicated device 422 that is developed specifically for reprogramming. Such a device could be configured to communicate with the first intermediary device through Bluetooth, as described above, or by MedRadio. In some exemplary embodiments, the dedicated device could be configured to communicate by MedRadio directly with the IPG so that only a single intermediary local device is needed. Remote support 430 communicates with the Patient Device through a network (e.g. through Wifi, cellular, wired connections or any combination thereof). Remote support 430 may be cloud-based, or can utilize a first party server, or a hosted server.

In some exemplary embodiments, the first intermediary device may be an existing Charger or Patient Remote, in which the software is updated to allow functionality as the first intermediary device. For example, the software is updated to enable the Charger or Patient Remote to act as an interpreter between the implanted medical device and another external device (e.g. the second intermediary device) which utilize different communication schemes. Specifically, the first intermediary device passes any commands or requests received from the second intermediary device in one communication scheme (e.g. Bluetooth), translates the commands or requests into another communication scheme (e.g. MedRadio), and sends the translated command or request to the implantable device. In this manner, the second intermediary device requests information from the implanted medical device, and the request is passed on to the implanted medical device by the first intermediary device in the appropriate communication scheme. In response to receiving this request, the implanted medical device then outputs a communication of the requested information, which is received by the first intermediary device and communicated to the second intermediary device according to the appropriate communication scheme. In this manner, the first intermediary device is merely relaying any commands and requests received between the implanted medical device and the second intermediary device. In some exemplary embodiments, the first intermediary device is not substantively modifying the content of the request or commands, nor is it responding to the content of the request or command, nor even responding to the device from which the command or request is received.

In some exemplary embodiments, the implanted medical device stores any information pertaining to therapy (e.g. current programming parameters, alternative programs, electrode information, patient information, etc.). During the programing procedure, to the extent this information is request by the remote entity, it is obtained from the memory of the implanted medical device. In some exemplary embodiments, some of this information may be obtained from the second intermediary device (e.g. smartphone, laptop), or a remote server in communication with the remote support entity, although typically it is stored on the implanted medical device and requested from the implanted medical device during reprogramming. In some exemplary embodiments, a request for information is received by the first intermediary device. In response to the request, the first intermediary device passes the request on the implanted medical device in the appropriate communication scheme. In response to receiving the request, the implanted medical device accesses the stored information requested, then outputs the information to the second intermediary device via the first intermediary device, as described previously. Thus, in the embodiment described, the software configuration of the first intermediary device limits the role of the first intermediary device to passing a request from one device to another device according to the appropriate communication scheme. In some exemplary embodiments, any commands, requests or information passed between devices may be temporarily stored on the first intermediary device only to the extent needed to relay the command, request or information between devices. In some exemplary embodiments of the remote programming procedure, the implanted medical device is the single source for the information regarding the current therapy program and parameters, which is advantageous as it avoids any potential conflicting information as to the current therapy being applied.

Figure 15A:
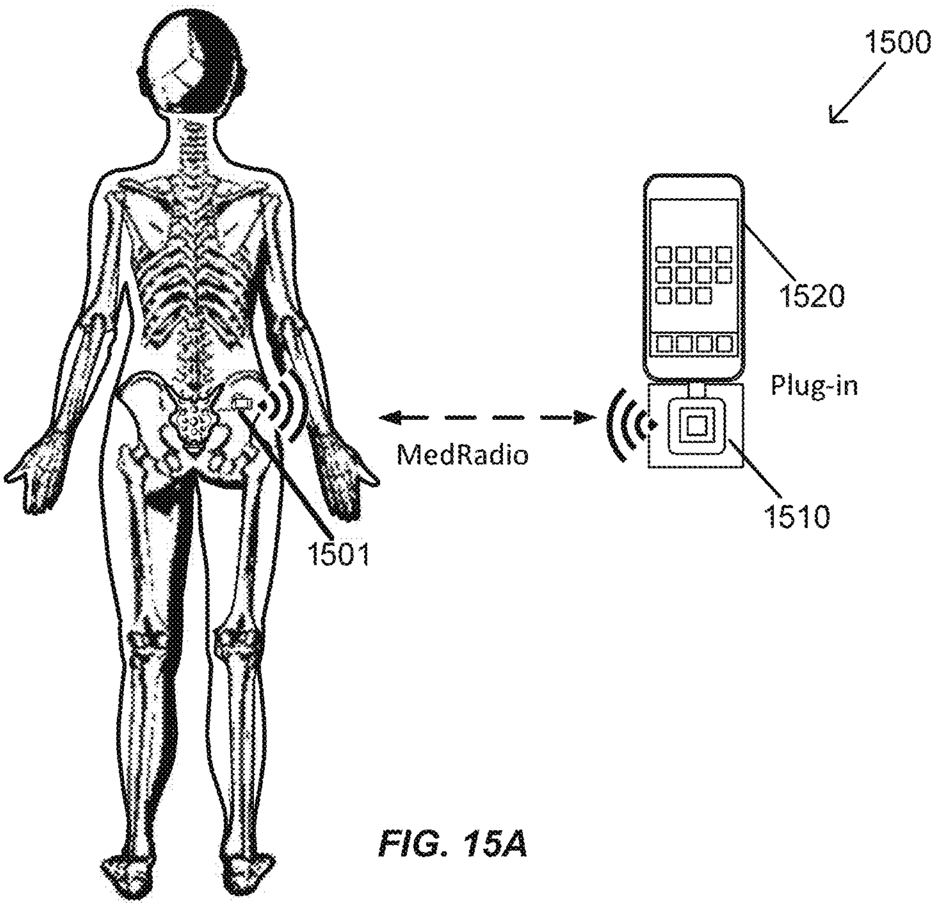
FIGS. 15A-15B schematically illustrate communication setups between a patient device and an implanted medical device for remote programming, in accordance with some exemplary embodiments.
Figure 15B:
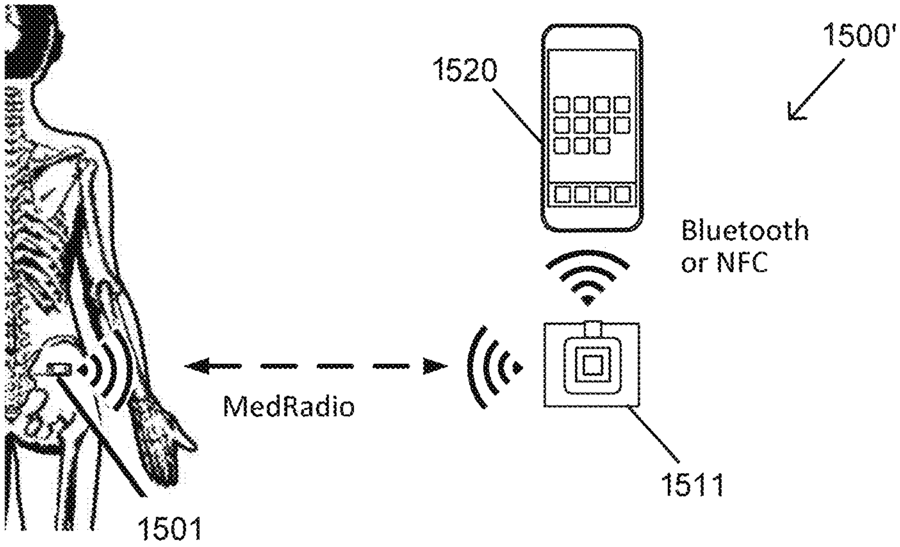

FIGS. 15A-15B schematically illustrate communication setups between a patient device and an implanted medical device for remote programming that utilize specialized devices as the first intermediary device, in accordance with some exemplary embodiments. In FIG. 15A, the first intermediary device is a plug-in accessory 1510 that plugs into the Patient Device 1520 such that it communicates directly with and is powered by Patient Device 1520. The plug-in accessory 1510 includes a communication means that communicates wirelessly with the implanted medical device 1501, typically by MedRadio. This approach allows a smartphone, which is not equipped with MedRadio communication means, to be used as the Patient Device 1520 to communicate with the implanted medical device without requiring the Charger or Patient Remote. In some exemplary embodiments, the plug-in accessory 1510 may further include a memory with software thereon, which may include any additional features, such as authentication functionality to ensure secure communication with the IPG and/or Remote Support, or software pertaining to the Patient App and/or reprogramming procedure. In FIG. 15B, the first intermediary may be configured as a separate specialized dedicated communicator device 1511 that wirelessly and locally communicates with both the IPG and the Patient Device 1520. In this embodiment, the communicator communicates with the IPG by MedRadio and communicates with the Patient Device 1520 by either Bluetooth or NFC. Similar to the plug-in accessory 1510 described above, the communicator device 1511 can further include a memory having software pertaining to the reprogramming procedure, which may include authentication functionality or the Patient App. In this embodiment, the intermediary device 1511 has its own power source. The above-noted approaches may be advantageous in that the devices 1510, 1511 may be configured with additional functionality and capabilities which may be beyond the capabilities of current Charger or Patient Remote devices noted above.

Figure 16:
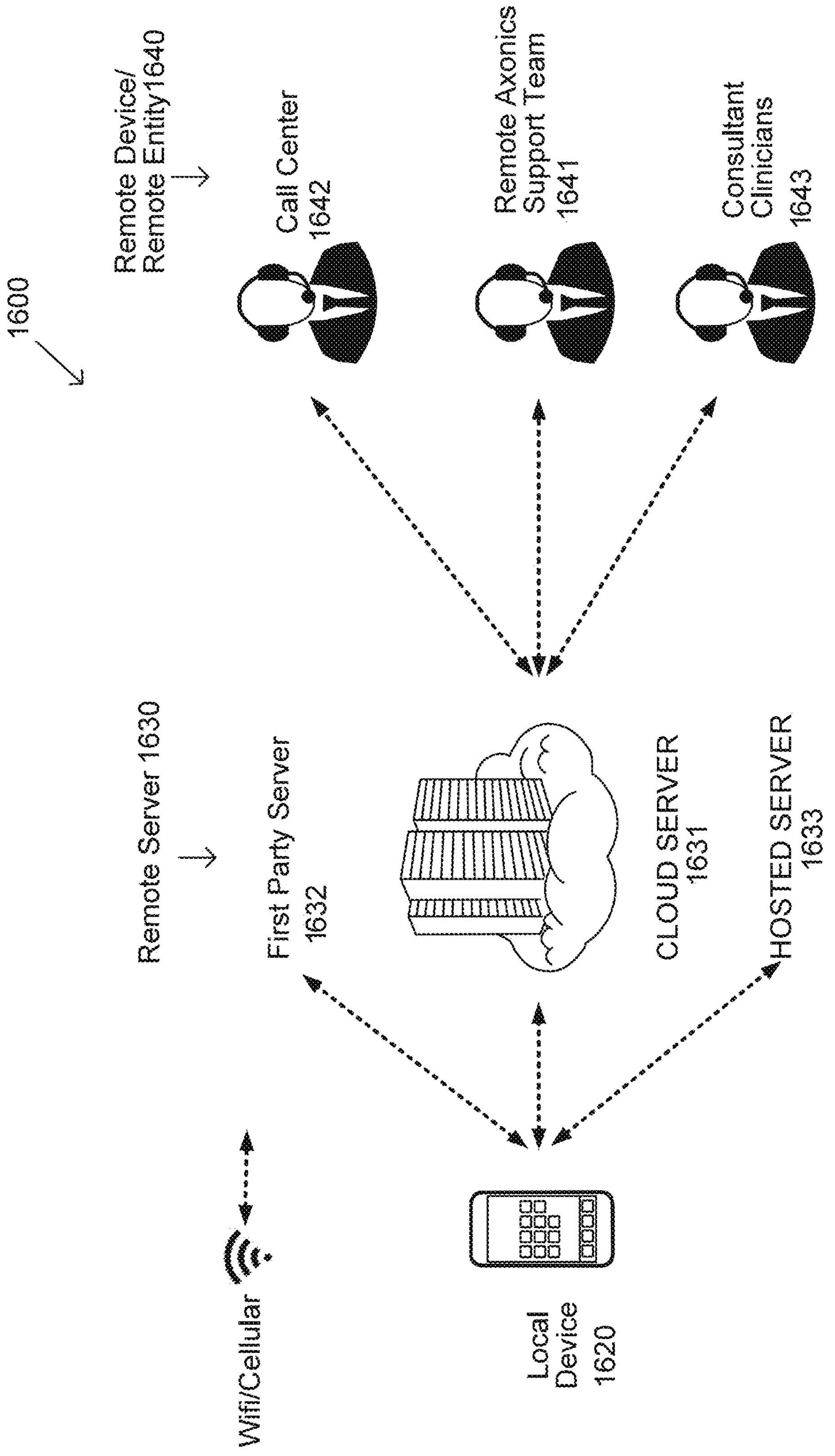
FIG. 16 schematically illustrate a communication setup between a patient device and a remote support entity, in accordance with some exemplary embodiments.

FIG. 16 schematically illustrates a communication system setup 1600 between a patient device and a remote support entity, in accordance with some exemplary embodiments. In this embodiment, the Patient Device 1620 communicates remotely by Wifi through a remote server 1630 with a Remote Device/Remote Entity 1640. In some exemplary embodiments, this communication may be through cellular or wired connection or any combination of Wifi, cellular and wire connections. In this embodiment, the Remote Server 1630 may be any of a first party server 1632 of the developer of the neurostimulation system, a cloud server 1631 or a hosted server 1633. The Remote Device/Remote Support entity 1640 may be a remote support team 1641 of the first party developer, a call center 1642, or a consultant clinician 1643, which may include contracted clinicians or the treating physician. The remote entity utilizes a remote device to receive input from the physician regarding reprogramming and to interact with the patient. The remote device may be any computing device, including a smartphone, tablet, laptop, clinician programmer, or desktop computer. In this embodiment, the remote device may include a Physician App or Remote Programming App framework that facilitates communication through the Patient App of the local Patient Device 1620. In some exemplary embodiments, the Physician App may be configured to be served to an internet browser and accessed by the remote device. This allows greater versatility in the setup of the remote entity, such that the remote device may be any of a smartphone, tablet, laptop and a desktop computing device. While the device application of the remote support entity is sometimes referred to "Physician App," it is appreciated that it is not required the remote support be a physician, and may include a clinician, medical profession, as well as technical experts or consultants with expertise in programming or troubleshooting of programming. It is appreciated that the remote programming procedure can utilize any combination of the support entities and/or server or communication paths depicted.

Figure 17:
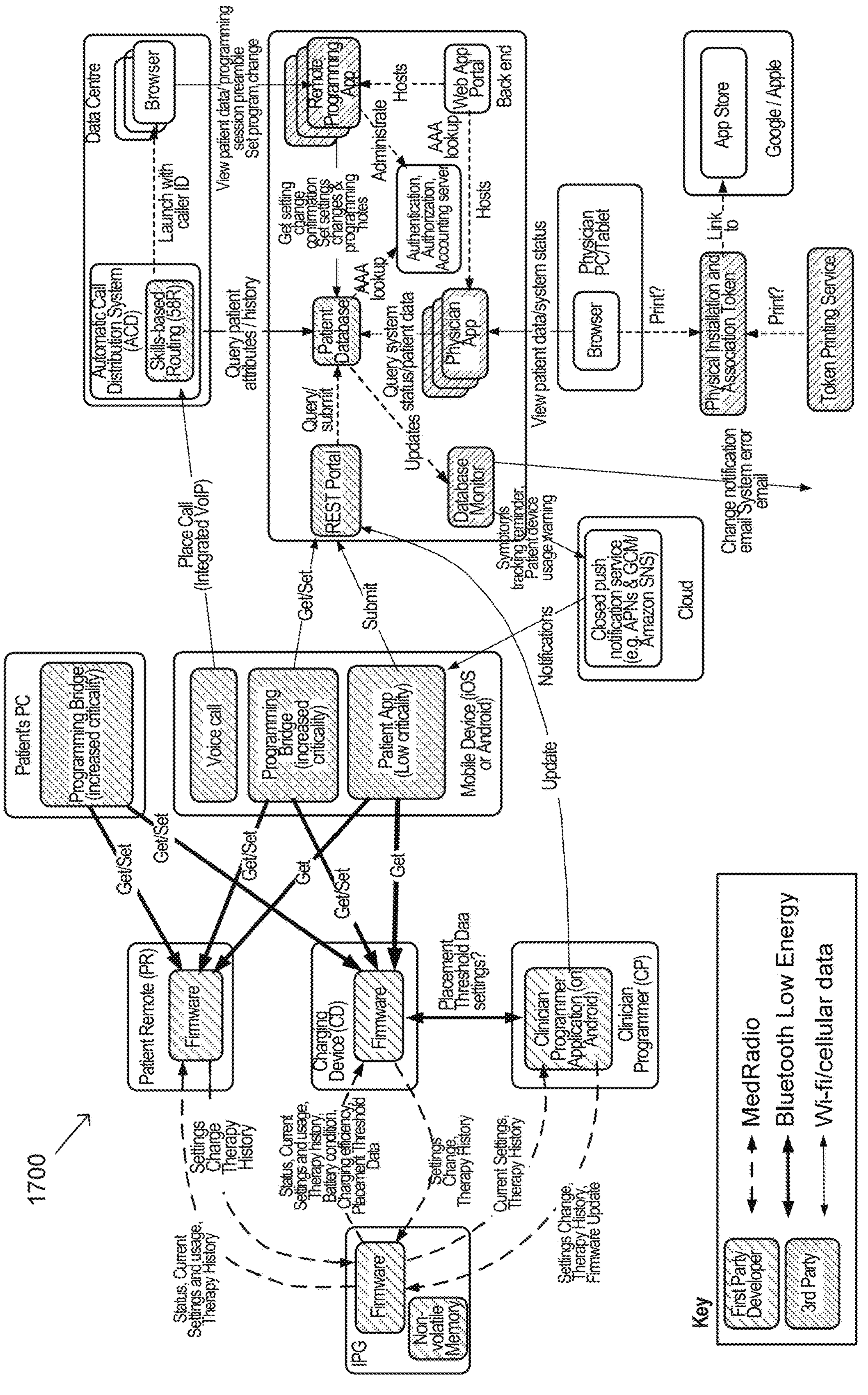
FIG. 17 schematically illustrates a workflow option for remote programming setups in accordance with some exemplary embodiments.

FIG. 17 schematically illustrates workflow 1700 that depicts various communications pathways and options for remote programming setups in accordance with some exemplary embodiments. The setup indicates additional details in regard to the functionality and steps of communication between the devices and entities of the remote programing setups described herein. The schematic also illustrates which devices and functions are associated with the first party developer of the neurostimulation system versus a third party developer (e.g. smartphone/computer manufacturer, consultant, physician). It is appreciated that this schematic represents a certain embodiment and that various alternatives or modifications are within the scope of the inventive concepts described herein. Further any of the individual aspects and communications depicted in FIG. 17 may be utilized in various other embodiments, including in any of the alternative setups described herein.

Figure 18:
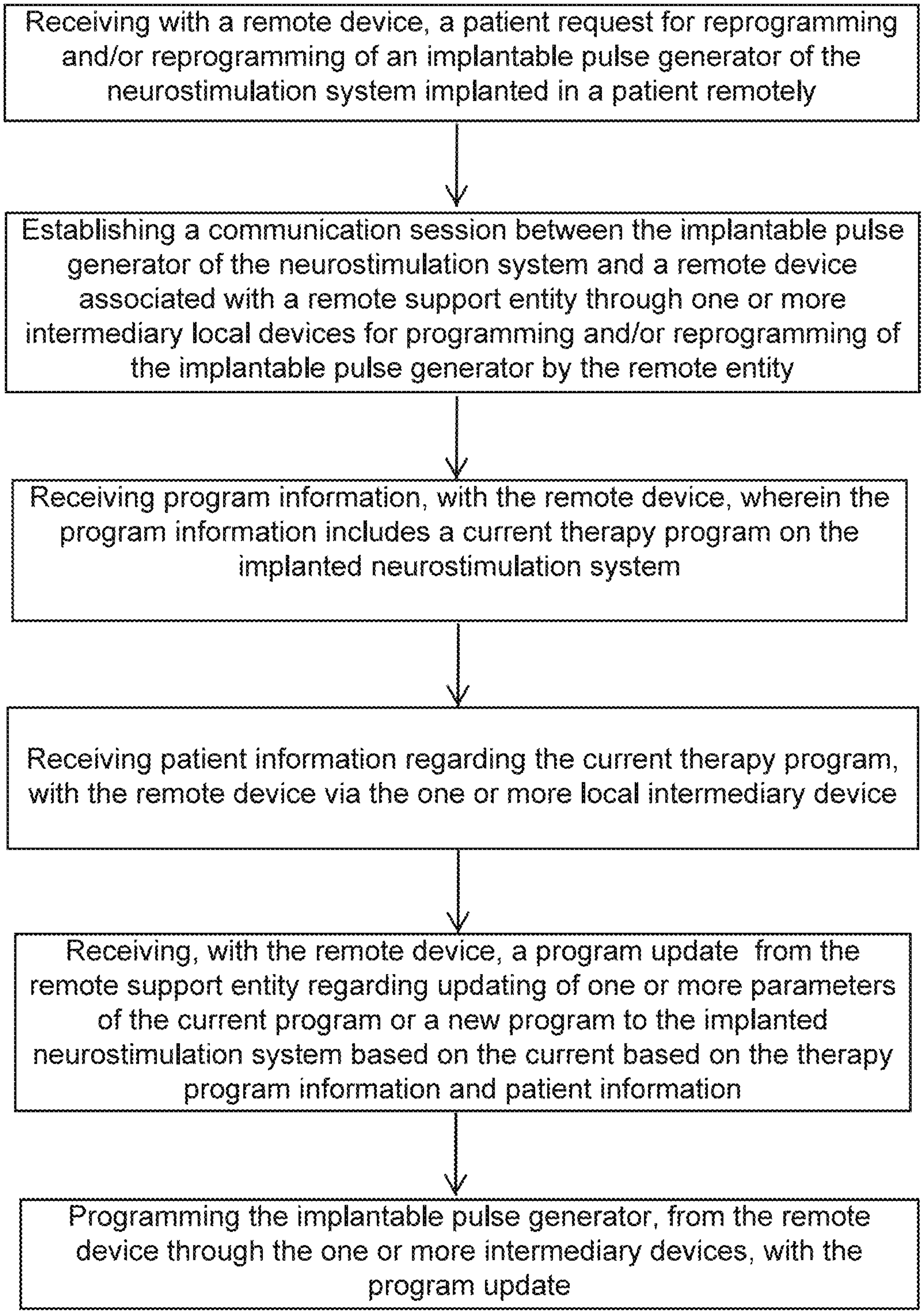
FIGS. 18-20 illustrate exemplary methods of remote programming implanted medical devices using communication setups in accordance with some exemplary embodiments.
Figure 19:
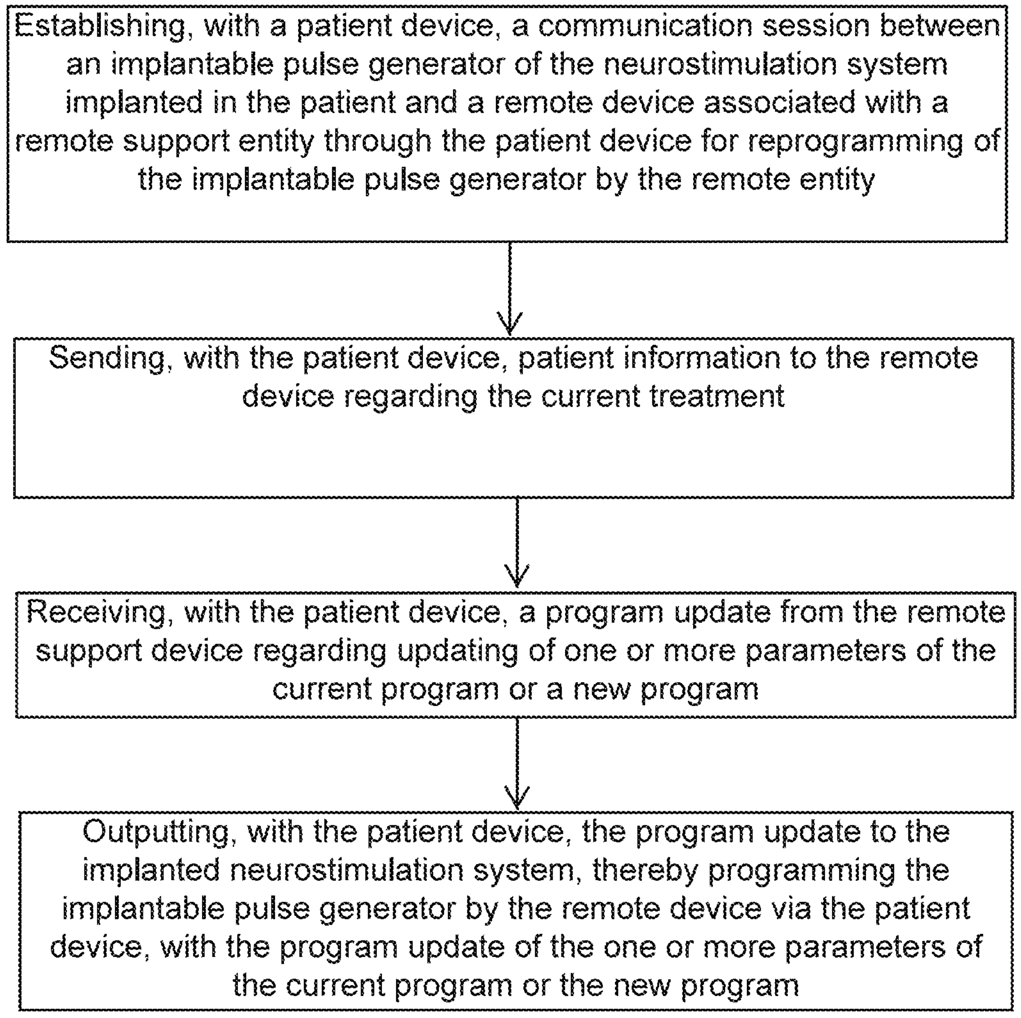
Figure 20:
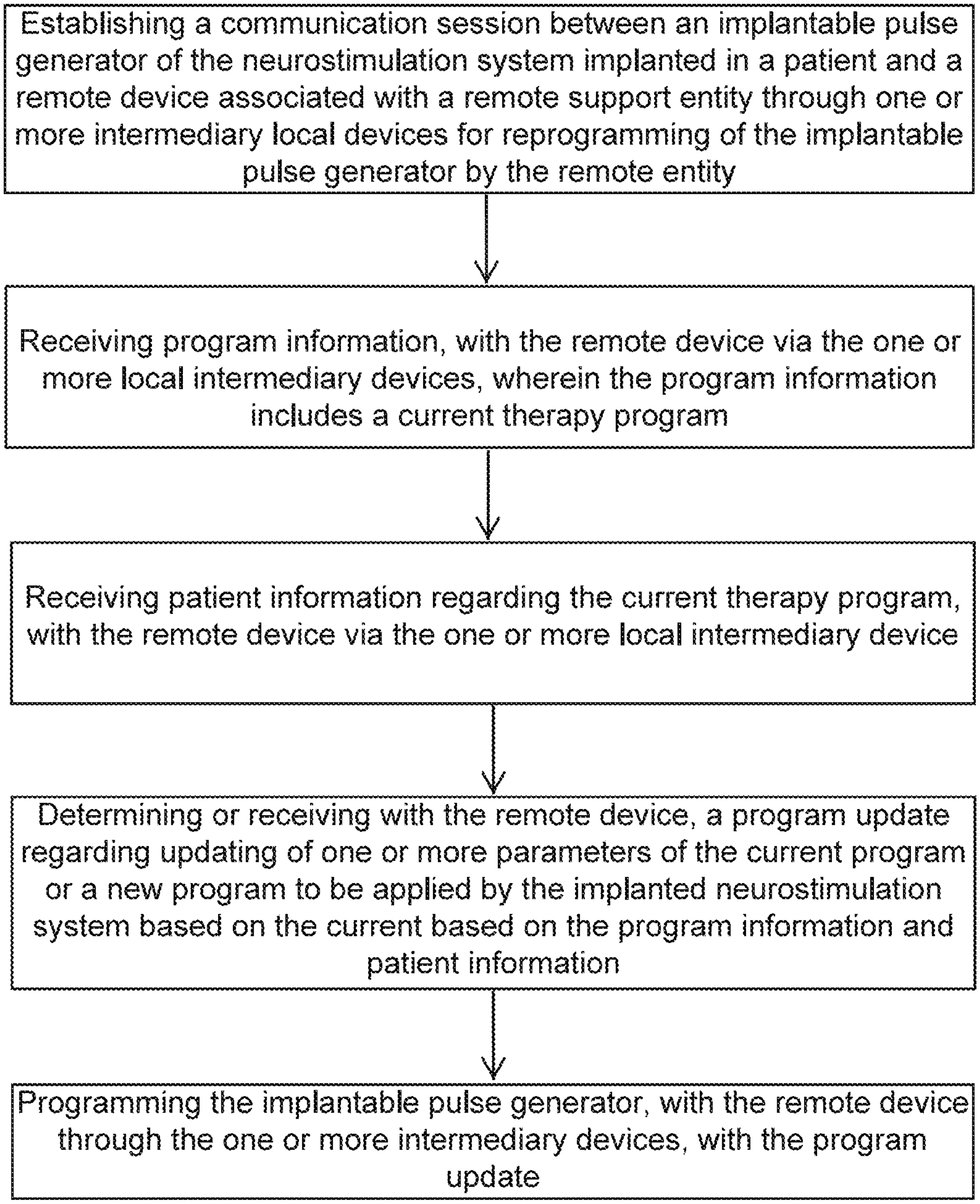

FIGS. 18-20 illustrate exemplary methods of remote programming an implanted medical devices using communication setups in accordance with some exemplary embodiments.

FIG. 18 depicts methods of facilitating programming of an implanted neurostimulation system remotely with one or more intermediary devices, in accordance with some exemplary embodiments. Such methods may include: receiving, with a remote device, a patient request for reprogramming and/or reprogramming of an implantable pulse generator of the neurostimulation system implanted in a patient remotely. After receiving the request, the system establishes a communication session between the implantable pulse generator of the neurostimulation system and a remote device associated with a remote support entity through one or more intermediary local devices for programming and/or reprogramming of the implantable pulse generator by the remote entity. Through this communication session, program information is received with the remote device via the one or more local intermediary devices. Program information may include a current therapy program on the implanted neurostimulation system. In addition, the remote device receives patient information regarding the current therapy program via the one or more local intermediary devices regarding the patient. The remote device then receives a program update input by the remote support updating one or more parameters of the current program or a new program for the implanted neurostimulation system based on the current based on the therapy program information and patient information. The system then programs the implantable pulse generator, from the remote device through the one or more intermediary devices, with the program update of the one or more parameters of the current program or the new program.

FIG. 19 depicts a method of remote programming by use of a patient device, in accordance with some exemplary embodiments. Such methods may include steps of: establishing, with a patient device, a communication session between an implantable pulse generator of the neurostimulation system implanted in the patient and a remote device associated with a remote support entity through the patient device for programming and/or reprogramming of the implantable pulse generator by the remote entity; sending, with the patient device, patient information to the remote device, wherein the patient information is associated with program information regarding a current therapy program applied by the implantable pulse generator of the implanted neurostimulation system. The patient device then receives a program update from the remote support device regarding updating of one or more parameters of the current program or a new program and outputs the program update to the implanted neurostimulation system, thereby programming the implantable pulse generator, from the remote device via the patient device, with the program update of the one or more parameters of the current program or the new program. In some exemplary embodiments, the patient device communicates with the implantable pulse generator through one or more intermediary devices, including any of a patient remote, charger, plug-in accessory or specialized communicator device.

FIG. 20 depicts a method of remote programming by use of a remote device, in accordance with some exemplary embodiments. Such methods may include steps of: establishing a communication session between an implantable pulse generator of the neurostimulation system implanted in a patient and a remote device associated with a remote support entity through one or more intermediary local devices for programming and/or reprogramming of the implantable pulse generator by the remote entity; receiving program information, with the remote device via the one or more local intermediary devices, from the intermediary local device wherein the program information includes a current therapy program on the implanted neurostimulation system; and receiving patient information regarding the current therapy program, with the remote device via the one or more local intermediary devices, from the intermediary local device regarding a current therapy program on the implanted neurostimulation system. The remote then device determines or receives by an update input, updating of one or more parameters of the current program or new program to the implanted neurostimulation system based on the current based on the therapy program information and patient information. The remote device then programs the implantable pulse generator, with the remote device through the one or more intermediary devices that include a patient device, with the program update of the one or more parameters of the current program or the new program.

Figure 21:
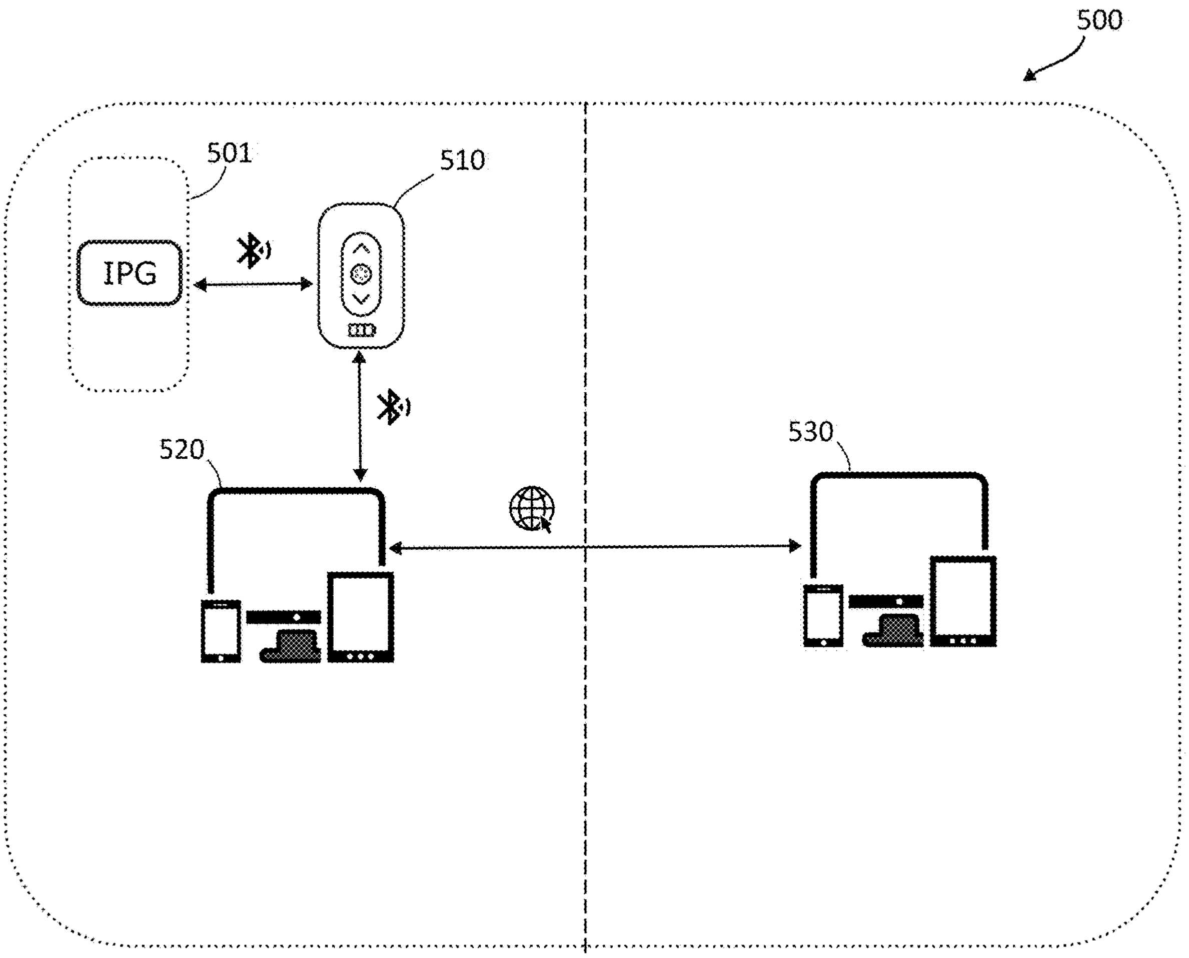
FIG. 21 illustrate an exemplary system setup for remote programming implanted medical devices using communication setups in accordance with some exemplary embodiments.

FIG. 21 shows an exemplary setup to facilitate remote programming in accordance with some exemplary embodiments. Setup 500 includes a conventional IPG 501 that communicates with a first intermediary device (patient remote 510), which in turn communicates with a second intermediary device (patient device 520, e.g. laptop or smartphone), which in turn communicates remotely with a remote programming device 530 (e.g. computing device of the manufacturer/company representative or a clinician). In this embodiment, the patient remote 510 is specially configured with a communication means (e.g. Bluetooth) suited for wirelessly communicating with the patient device 520. This patient remote contrasts with conventional patient remotes that were capable of communication only with the IPG, for example by MedRadio. In some exemplary embodiments, the remote communication between the patient device 520 and programming device 530 is through a cellular network. In some exemplary embodiments, the patient device 520 includes specialized software application thereon (e.g. IPG communication software) for facilitating local communication with the IPG and remote communication with the programming device 530. The programming device 530 may include a corresponding application (e.g. IPG communication software) for the company representative or clinician to communicate with the IPG through the first and second intermediary devices to facilitate remote programming by the representative or clinician through a user interface of the remote device. In some exemplary embodiments, the application software on the programming device 530 may be configured to allow adjustment of existing programs stored on the IPG, replacement of existing programs with alternative programs or newly determined programs, as well as download of IPG information (e.g. current or past programs, activity etc.). In other embodiments, remote programming may be accomplished through a web-based portal accessed by each of the patient device 520 and the remote device 530.

FIGS. 22-26 illustrates various alternative setup options facilitating remote programming, in accordance with some exemplary embodiments. These setups can utilize existing communication capabilities of various devices or include specialized devices or software applications. In one aspect, these setups can utilize a patient database portal that utilizes: communication (e.g., by Wi-Fi and/or cellular) to a secure server, in particular a web-based patient database portal, and that is designed to facilitate remote programming. The database portal can maintain various types of data pertaining to the patient's treatment, for example, 1) the patient program history, 2) a device event log, and 3) a patient bladder diary. In some exemplary embodiments, the setups may be configured to allow the patient to self-program by utilizing information exchanged through the patient database portal, for example, by receiving an updated or modified programs from the portal based on information previously obtained from the patient.

Figure 22:
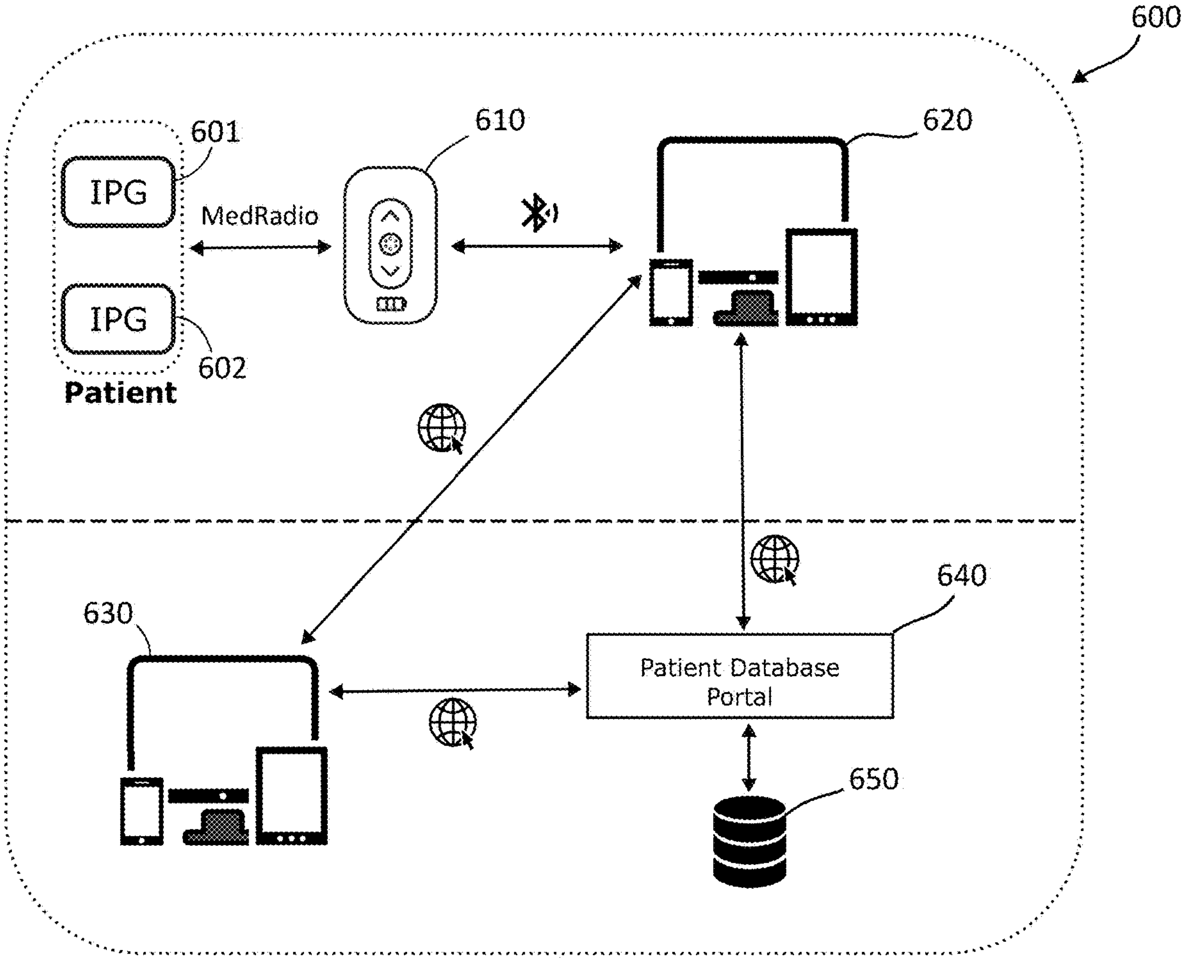
FIGS. 22-26 illustrate various options of exemplary system setups for remote programming implanted medical devices using communication setups in accordance with some exemplary embodiments.

FIG. 22 shows system setup 600 that utilizes a specialized patient remote 610 so as to allow remote programming through the patient remote, which allows use of differing types of IPGs. For example, previous embodiments that rely on a charging device to communicate with an IPG are not amenable for use with an IPG with a non-rechargeable battery since no charging device is used. This setup can leverage existing patient programmer's functionality in communicating with the IPG so as to be backwards compatible. The setup further leverages existing smartphone/tablet functionality having Bluetooth and Wifi communications, since the patient remote communicates with the patient device 620 by Bluetooth. The setup can further utilize a hosted Patient Bladder/Voiding Diary Application maintained by the patient with the patient device 620. Optionally, this setup may be provided only to those patients having a need for reprogramming. Advantageously, the impact of remote programming on the usable life of the patient remote is marginal (e.g. ten 20-minute sessions use about 20% or less of the patient remote's battery energy).

In system setup 600, the first intermediary device is a specialized patient remote 610 that is capable of a first type of communication (e.g. MedRadio) with either IPG 601 having a rechargeable battery or IPG 602 having a non-rechargeable battery. The patient remote 610 is specially configured with a second type of communication (e.g. Bluetooth) for communication with a second intermediary device of the patient device 620 (e.g. laptop, tablet, smartphone of the patient), which in turn communicates wirelessly with the programming device 630 and/or a remote database portal 640 connected to database 650 containing various types of data pertaining to the patient's treatment, for example, 1) the patient program history, 2) a device event log, and 3) a patient bladder diary. The communication between the patient device 620 and the remote programming device 630 may be a third type of communication (e.g. cellular, 4G, 5G, Wifi or any combination thereof) and can further include a phone call, video call or text-type exchange between clinician and patient. Optionally, the patient device 620 can further communicate with a patient database portal 640, which may be accessed through a specialized application on the smartphone or alternatively, accessed through a standard web browser on the patient device. The patient device 620 can exchange information (e.g. upload and download) from the patient database portal 640 as needed for reprogramming. In another aspect, the remote programming device 630 can exchange information directly with the patient database portal to inform remote programming. The remote programing device 630 may be a standard computing device (e.g. commercial tablet or smartphone) with a specialized application software or may be a specialized device. Similarly, the patient device 620 may be a standard computing device (e.g. commercial tablet or smartphone) with specialized application software or may be a specialized device.

Figure 23:
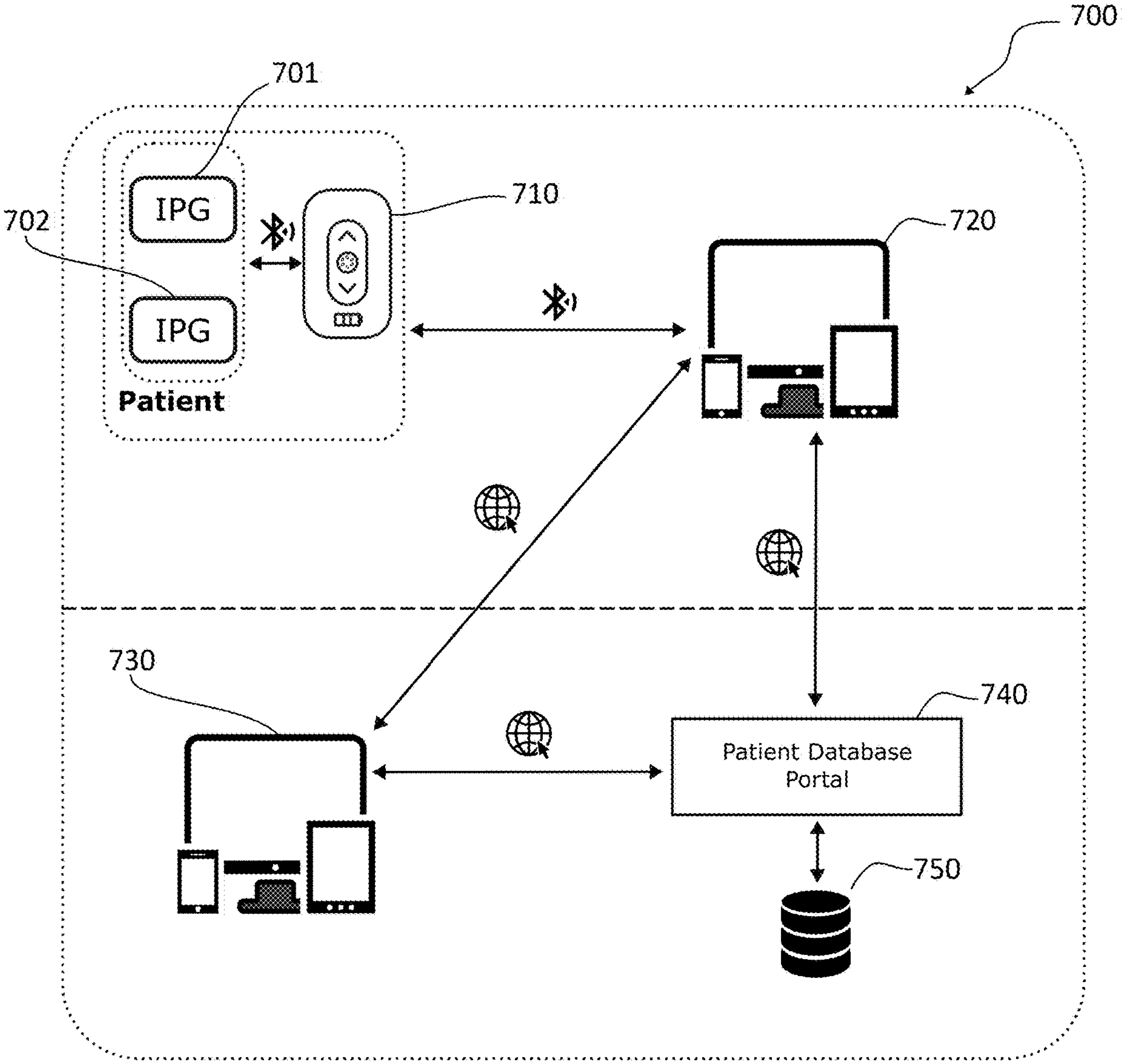

FIG. 23 shows setup 700 in which either IPGs 701, 702 can communicate locally with the patient device 720 by a first type of communication (e.g. Bluetooth). Similar to the previous setup, the patient device 720 can communicate remotely with the remote programming device 730 and/or the patient database portal 740 with a second type of communication (e.g. cellular, 4G, 5G, WiFi, or any combination thereof), where the patient database portal is connected to a database 750 containing various types of data pertaining to the patient's treatment, for example, 1) the patient program history, 2) a device event log, and 3) a patient bladder diary. The setup can utilize specialized application software on the patient device 720 and remote programing device 730, to facilitate remote programming and can utilize any of a phone call, video call or text-exchange. This setup can leverage existing smartphone/tablet communication capabilities of Bluetooth and Wifi, and may include enabling of Bluetooth functionality on current patient remote devices. In some exemplary embodiments, the patient device 720 hosts the bladder diary application and updates the patient database portal 740 with therapy information. In some exemplary embodiments, this setup is not backwards compatible with conventional IPGs without Bluetooth functionality. In some exemplary embodiments, the patient remote 710 can communicate with the IPGs by the first type of communication (e.g. Bluetooth).

Figure 24:
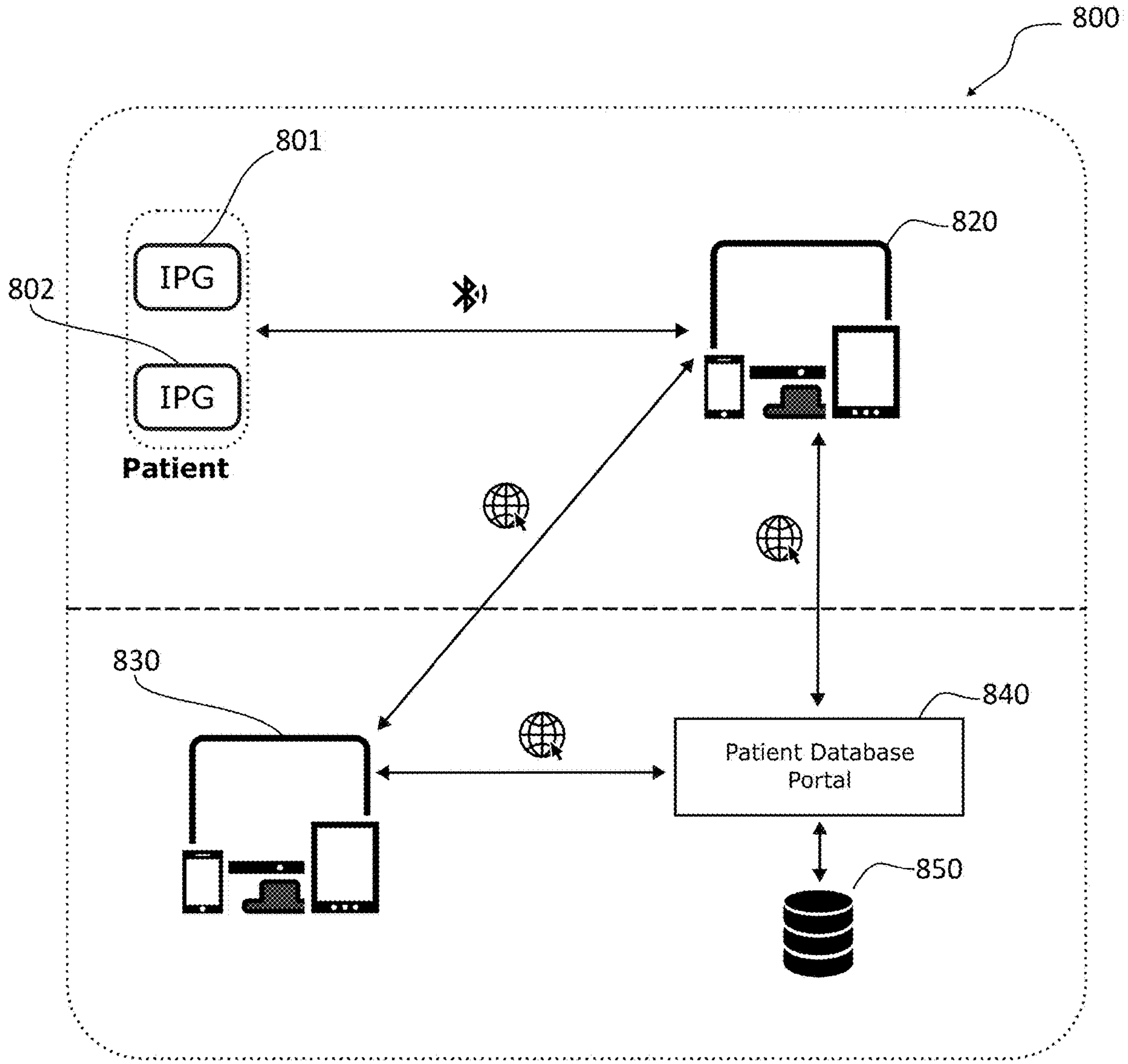

FIG. 24 shows setup 800 having substantially the same or similar features and compatibilities as those in setup 700, and includes IPGs 801, 802 that communicate locally with the patient device 820 by a first type of communication (e.g. Bluetooth). In this embodiment, since the IPGs communicate directly with the patient device 820, the functionality of the patient remote may be incorporated into the patient device 820, for example through a specialized software application (e.g. Patient Remote App) that may be configured for adjusting stimulation or selecting between multiple stimulation programs. This application may be separate from the remote programming application (e.g. IPG communication software) that allows communication between the remote programming device 830 and the IPG through the patient device 820. This setup can similarly include the features in Option 2A pertaining to utilizing phone calls/video calls/texting, as well as the patient database portal 840 connected to a database 850 containing various types of data pertaining to the patient's treatment, for example, 1) the patient program history, 2) a device event log, and 3) a patient bladder diary.

Figure 25:
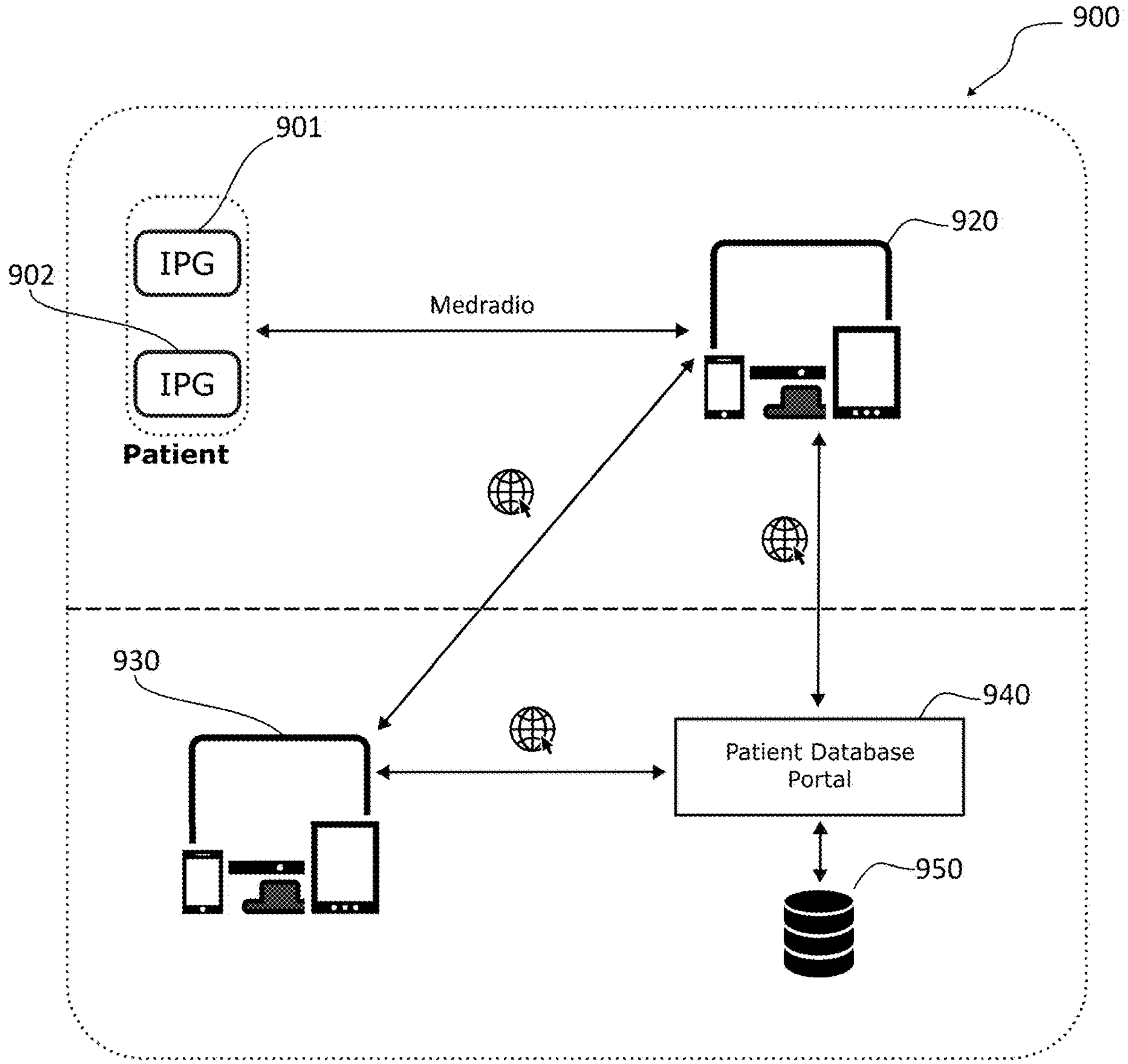

FIG. 25 shows setup 900 having a custom patient device 920 that is a combined patient remote and intermediary device for remote programming. In some exemplary embodiments, the patient device 920 may be configured for communication by a first type of communication (e.g. MedRadio) to communicate with IPGs 901, 902 and for communication by a second type of communication (e.g. cellular, WiFi) to communicate with the remote programming device 930 and/or the patient database portal 940, wherein the database portal 940 is connected to a database 950 containing various types of data pertaining to the patient's treatment, for example, 1) the patient program history, 2) a device event log, and 3) a patient bladder diary. In some exemplary embodiments, the custom patient device 920 may be configured for local communication by MedRadio and for remote communication through WiFi, cellular or any combination thereof. In this embodiment, since the IPGs can communicate directly with the patient device 920, the functionality of the existing patient remote may be incorporated into the patient device 920, for example through a specialized application for adjusting stimulation or selecting between multiple stimulation programs. Accordingly, this approach is backwards compatible with existing IPGs that communicate with dedicated patient remotes through the first type of communication (e.g. MedRadio). This setup does however require the custom patient device 920 be configured for communication by both first and second types of communication in order to function as the intermediate device for remote programming. Advantageously, this approach may present fewer operating system maintenance issues and require fewer updates as the need for a separate patient remote has been eliminated. This setup otherwise includes substantially the same or similar features as in previous setups in regard to use of phone/video/text communications for reprogramming, the patient database portal, and the patient device acting as an intermediary device for remote programing by the remote programing device 930. In some exemplary embodiments, the setup allows self-programming of the IPG with the patient device 920 utilizing the patient portal 940.

Figure 26:
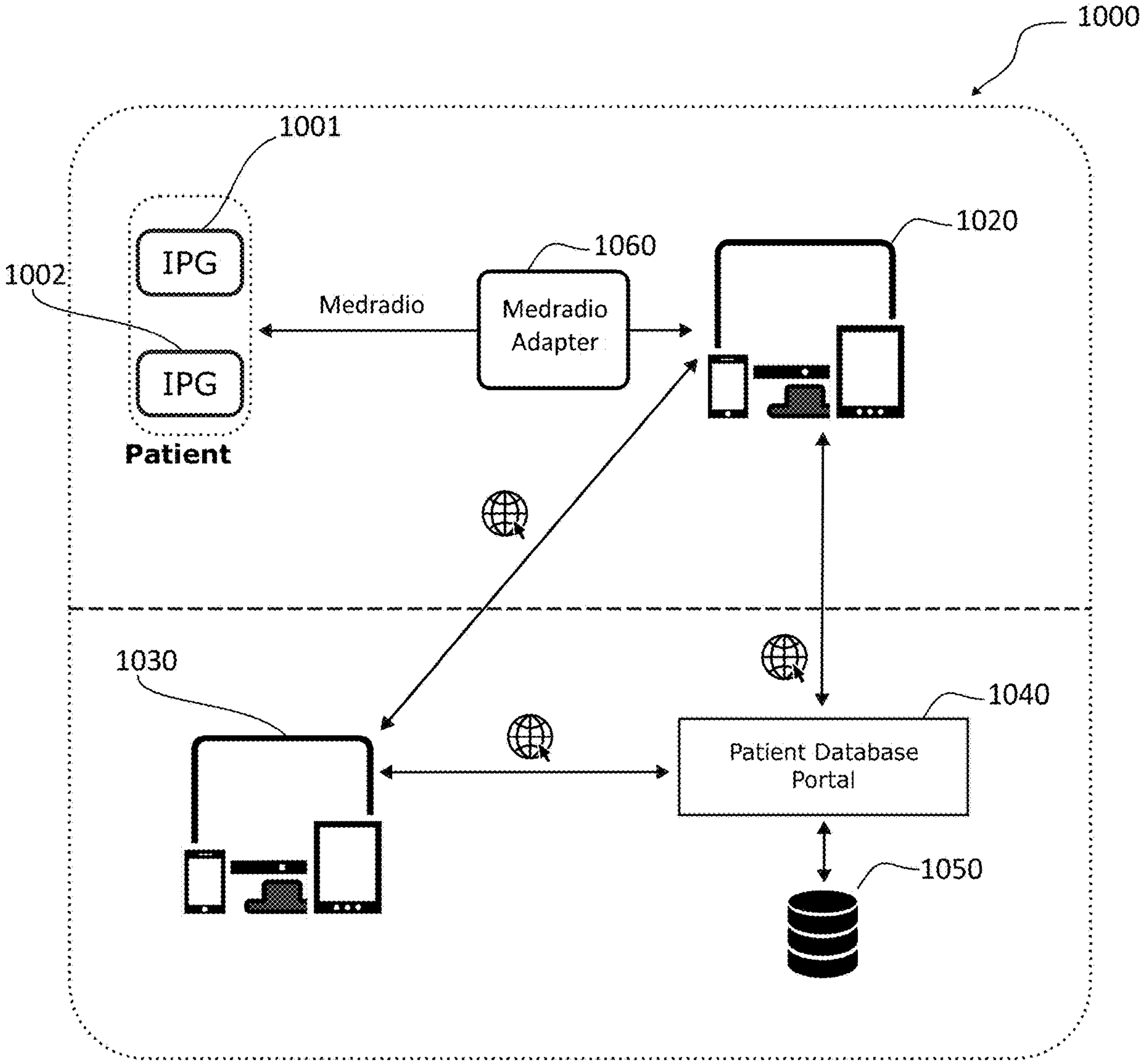

FIG. 26 shows setup 1000 having a personal patient device 1020 (e.g. a standard smartphone/tablet personal to the patient) having one or more specialized software applications thereon such that the device functions as a combined patient remote and intermediary device for remote programming. In this example, the patient device 1020 is a personal device of the patient that is coupled with a communication adapter 1060 accessory (e.g. plug-in or wireless accessory—see FIGS. 15A-15B) to facilitate communication by a first type of communication (e.g. MedRadio, which is not native to the device) to allow communication to IPGs 1001, 1002. The native communication of the patient device 1020 in a second type(s) of communication (e.g. cellular, WiFi) may be used to communicate with the remote programming device 1030 and/or the patient database portal 1040, wherein the database portal 1040 is connected to a database 1050 containing various types of data pertaining to the patient's treatment, for example, 1) the patient program history, 2) a device event log, and 3) a patient bladder diary. In this embodiment, since the IPGs can communicate directly with the patient device 1020, the functionality of the patient remote may be incorporated into the patient device 1020, for example through a specialized application for adjusting stimulation or selecting between multiple stimulation programs. Accordingly, this approach is backwards compatible with prior systems utilizing IPGs that communicate with dedicated patient remotes through the first type of communication (e.g. MedRadio). This setup is advantageous as it further eliminates the need for a custom, dedicated intermediary device and allows use of the patient's own personal device (e.g. smartphone/tablet) for both patient remote functions and for remote programming. This setup otherwise includes substantially the same or similar features as in previous setups in regard to the capability of phone/video/text communications for reprogramming, the patient database portal, and the patient device acting as an intermediary device for remote programing by the remote programing device 1030 or as a self-programming device utilizing the patient portal 1040. In some exemplary embodiments, the setup allows self-programming of the IPG with the patient device 1020 utilizing the patient portal 1040.

FIGS. 22-26 describe various aspects/features associated with each of the above options. These aspects highlight how each of the proposed setups may be integrated with existing systems and devices, to leverage existing functionality, as well as the implications and advantages associated with modified, custom or new devices. For example, options utilizing existing IPGs may be implemented within current patients having existing (non-BT enabled) IPGs already implanted, whereas other setup options, may be implemented in updated neurostimulation systems to be implanted in new patients. It is appreciated that these features are exemplary and variations for each of the options, or other options not shown, may be realized. For example, setups utilizing direct communication between patient device and IPG can additionally include a patient remote in a redundant manner, to provide the patient with additional options and more flexibility per user preference. Various features are noted as being performed by the device provider, "Provider," (e.g. Axonics), however it is appreciated that this term could alternatively refer to any customer service, clinical care team representative. It is appreciated that each of the features listed could be utilized in a different setup option in any suitable compatible manner.

Figure 27:
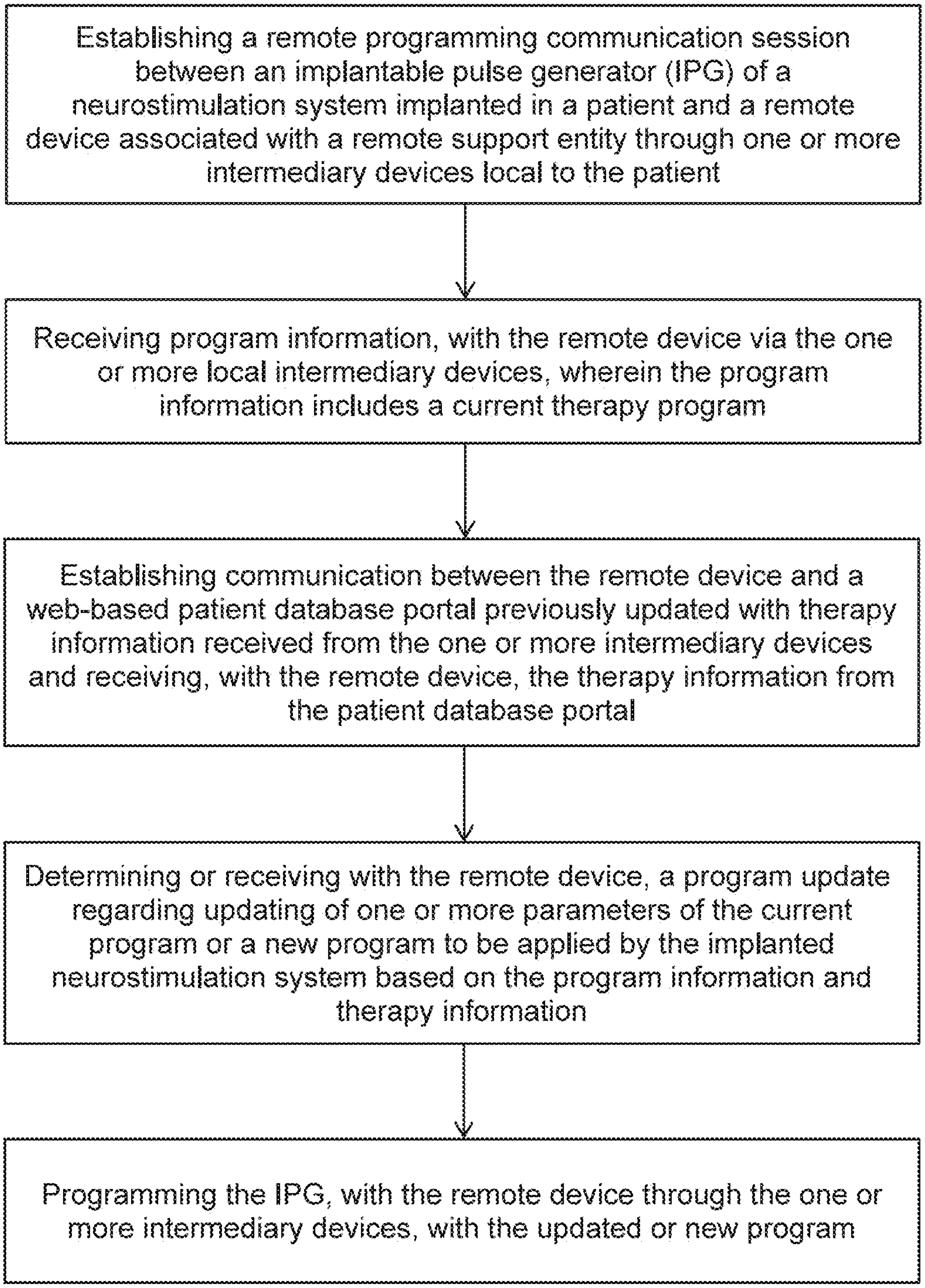
FIGS. 27-28 illustrate exemplary methods of remote programming implanted medical devices using the various optional system setups in accordance with some exemplary embodiments.

FIG. 27 depicts an exemplary method of programming that includes a step of: establishing a remote programming communication session between an IPG of a neurostimulation system implanted in a patient and a remote device associated with a remote support entity through one or more intermediary devices local to the patient, and receiving program information, with the remote device via the one or more local intermediary devices, the program information including a current therapy program. Next, the method may include steps of: establishing communication between the remote device and a web-based patient database portal previously updated with therapy information received from the one or more intermediary devices and receiving, with the remote device, the therapy information from the patient database portal; and determining or receiving with the remote device, a program update regarding updating of one or more parameters of the current program or a new program to be applied by the implanted neurostimulation system based on the program information and therapy information. Finally, the method entails programming the IPG, with the remote device through the one or more intermediary devices, with the updated or new program.

Figure 28:
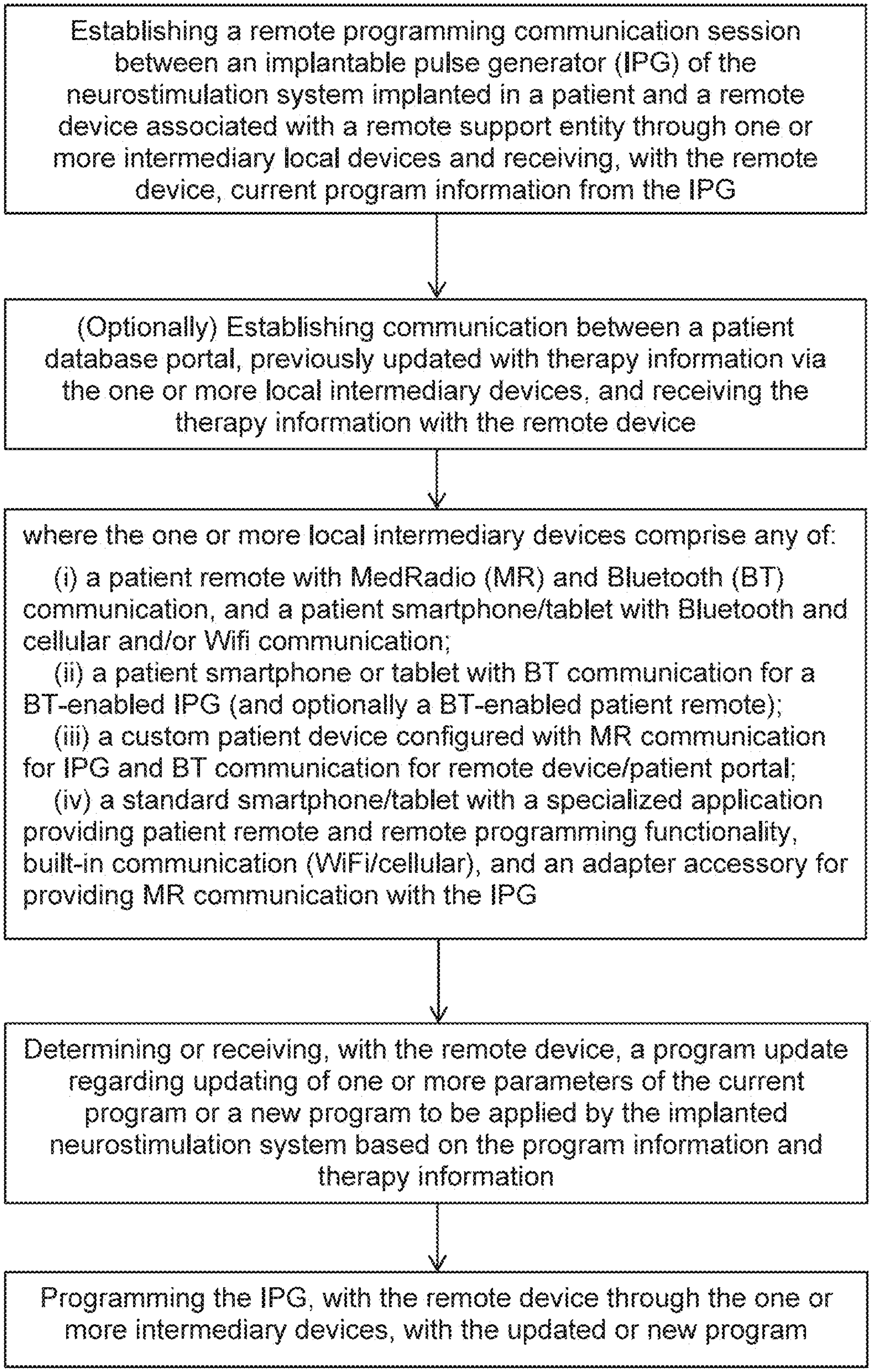

FIG. 28 depicts another exemplary method of remote programming using one or more intermediary devices. The method may include steps of: establishing a remote programming communication session between an IPG of the neurostimulation system implanted in a patient and a remote device associated with a remote support entity through one or more intermediary local devices; and receiving, with the remote device, current program information from the IPG. Optionally, the method may include establishing communication between a patient database portal, previously updated with therapy information via the one or more local intermediary devices, and receiving the therapy information with the remote device. In some exemplary embodiments, the one or more local intermediary devices comprise any of: (i) a patient remote with MedRadio (MR) and Bluetooth (BT) communication, and a patient smartphone/tablet with Bluetooth and cellular and/or Wifi communication; (ii) a patient smartphone or tablet with BT communication for a BT-enabled IPG (and optionally a BT-enabled patient remote); (iii) a custom patient device configured with MR for communication for IPG and BT for communication with the remote device/patient portal; and (iv) a standard smartphone/tablet with a specialized application providing patient remote and remote programming functionality, built-in communication means (WiFi/cellular), and an adapter accessory for providing MR for communication with the IPG. The method then entails, determining or receiving, with the remote device, a program update regarding updating of one or more parameters of the current program or a new program to be applied by the implanted neurostimulation system based on the program information and therapy information; and programming the IPG, with the remote device through the one or more intermediary devices, with the updated or new program.

In the foregoing specification, various embodiments are described, but those skilled in the art will recognize that the invention is not limited thereto. Various disclosed features, embodiments and aspects may be used individually or jointly. Further, the described embodiments may be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art. Any references to publication, patents, or patent applications are incorporated herein by reference in their entirety for all purposes.

What is claimed is:

1. A method of remotely programming an implanted neurostimulation system, the method comprising:

establishing a communication session between an implantable pulse generator of a neurostimulation system, configured to provide electrical stimulation pulses to the patient, implanted in the patient and a remote programming device associated with a remote support entity through one or more intermediary local devices of the patient;

receiving program information, with the remote device via the one or more local intermediary devices, wherein the program information includes a current therapy program associated to the electrical stimulation pulses applied by the implanted neurostimulation system to the patient, wherein the one or more local intermediary devices comprise a patient device having a user interface thereon;

receiving therapy information, with the remote device, from a web-based portal, wherein the therapy information is previously received by the web-based portal remotely from the one or more local intermediary devices, and wherein the therapy information is updated by the one or more intermediary devices;

determining or receiving, with the remote device, a program update regarding updating of one or more parameters of the electrical stimulation pulses associated with the current therapy program, wherein the update is based on the program information and therapy information; and applying the program update to the neurostimulation system, thereby changing the one or more parameters of the electrical stimulation pulses associated with the current therapy program provided to the patient.

2. The method of claim 1, wherein the therapy information is stored on a patient database and comprises any of: a patient program history, a device event log of the implantable pulse generator; and a patient bladder diary.

3. The method of claim 1, wherein the therapy information is received by the web-based portal from the patient device and updated remotely periodically with the patient device.

4. The method of claim 1, wherein the one or more intermediary devices includes a first and second intermediary device, wherein the first intermediary device comprises a patient remote that communicates with the implantable pulse generator for patient adjustment of stimulation levels and the second intermediary device is the patient device, wherein the patient device comprises a tablet or smartphone of the patient configured to communicate with each of the patient remote and the remote device of the remote support entity.

5. The method of claim 4, wherein the patient remote is configured to communicate with the implantable pulse generator by a first type of communication and to communicate with the second intermediary device by a second type of communication.

6. The method of claim 5, wherein the first type of communication is MedRadio and the second type of communication is Bluetooth.

7. The method of claim 4, wherein the second intermediary device is configured to communicate with the remote device and the web-based portal by a remote type of communication.

8. The method of claim 7, wherein the remote type of communication is any of cellular and WiFi or any combination thereof.

9. The method of claim 8, wherein the remote device is located further from the pulse generator than the first and second intermediary device.

10. The method of claim 1, wherein the patient device is configured to communicate locally with the implantable pulse generator and to communicate remotely with the remote device of the remote support entity and/or the patient portal database.

11. The method of claim 10, wherein the implantable pulse generator is Bluetooth-enabled and the patient device is a smartphone or tablet that communicates locally by Bluetooth with the implantable pulse generator.

12. The method of claim 10, further comprising: adjusting one or more parameters of the current therapy with a patient remote configured to communicate with the implantable pulse generator by Bluetooth.

13. The method of claim 11, wherein the smartphone or tablet includes specialized software application thereon that provides functionality for the patient device to operate as a patient remote to adjust stimulation of therapy in addition to operating as the intermediary device for remote programming.

14. The method of claim 1, wherein the patient device is a customized device that communicates locally and directly with the implantable pulse generator by a first type of communication and communicates remotely with the remote device and/or web-based portal by a second type of communication.

15. The method of claim 14, wherein the first type of communication is MedRadio and the second type of communication is cellular, Wifi or a combination thereof.

16. The method of claim 1, wherein the patient device is communicatively coupled to an adapter accessory that provides a first type of communication for communicating with the implantable pulse generator, wherein the patient device has built-in communication for a second type of communication.

17. The method of claim 16, wherein the first type of communication is MedRadio and the second type of communication is cellular, Wifi or a combination thereof.

18. The method of claim 16, wherein the patient device comprises a standard smartphone or tablet of the patient having specialized software stored thereon for operating as both a patient remote for adjusting stimulation and for operating as the intermediary device for remote programming.

19. The method of claim 18, wherein the adapter accessory electrically connects to the patient device or wirelessly connects to the patient device by Bluetooth.

20. The method of claim 1, further comprising: self-programming with the patient device by determining or receiving, with the patient device from the web-based portal, a program update regarding updating of one or more parameters of the current program to be applied by the implanted neurostimulation system based on the program information and therapy information received by the web-based portal.

21. A remote programming system for programming an implanted neurostimulation system remotely with a remote support entity, the system comprising:

an implantable pulse generator of the neurostimulation system implanted in a patient, the implantable pulse generator having one or more antennas for communicating wirelessly with one or more external devices;

wherein the one or more external devices includes one or more intermediary devices configured to communicate with the implantable pulse generator through local communication and to further communicate by remote communication;

a remote programming device associated with the remote support entity, the remote device being configured to communicate with the one or more intermediary devices by the remote communication, wherein the remote device includes a user interface for receiving an input from the remote support entity; and a patient database portal that is a web-based portal having therapy information thereon that is updated by the one or more intermediary devices, wherein the patient database portal is accessible by the remote programmer device and the one or more intermediary devices, and wherein the therapy information is previously received by the web-based portal remotely from the one or more local intermediary devices.

22. The system of claim 21, wherein the one or more intermediary devices comprise any of: a patient remote, a patient device, and an adapter accessory.

23. The system of claim 21, wherein the one or more intermediary devices comprise a patient remote configured to communicate locally by both MedRadio and Bluetooth, and a patient device that communicates locally by Bluetooth and remotely by cellular and/or WiFi.

24. The system of claim 21, wherein the implantable pulse generator is Bluetooth-enabled and the one or more intermediary devices comprise a patient device that communicates locally and directly with the implantable pulse generator by Bluetooth and communicates remotely with the remote programming device by cellular, Wifi or a combination thereof.

25. The system of claim 24, wherein the patient device is a standard smartphone or tablet having specialized software application operable thereon to facilitate remote programming.

26. The system of claim 25, further comprising: a patient remote for adjusting stimulation therapy that communicates with the implantable pulse generator by Bluetooth.

27. The system of claim 25, wherein the specialized software is further configured so that the patient device communicates with the implantable pulse generator by Bluetooth and operates as a patient remote for adjusting stimulation therapy.

28. The system of claim 21, wherein the one or more intermediary devices comprise a custom patient device configured to communicate with the implantable pulse generator by Bluetooth and communicate with the remote programming device by cellular, WiFi or a combination thereof.

29. The system of claim 21, wherein the one or more intermediary devices comprise a patient device with a specialized software application operable thereon to facilitate remote programming, and an adapter accessory that is communicatively coupled with the patient device to facilitate local communication with the implantable pulse generator.

30. The system of claim 29, wherein the patient device comprises a standard smartphone or tablet with built-in communication for cellular and/or WiFi by which the patient device communicates with the remote programing device, and wherein the accessory device is configured to communicate with the implantable pulse generator by MedRadio.

31. The system of claim 29, wherein the accessory is a plug-in device that electrically connects to the patient device or is wirelessly connected by Bluetooth.

32. The system of claim 21, wherein the one or more intermediary devices comprise a patient device having a user interface thereon and a specialized software application configured for self-programming of the implantable pulse generator with the patient device, by determining or receiving with the patient device, a program update regarding updating of one or more parameters of the current program to be applied by the implanted neurostimulation system based on an update received from the patient database portal, wherein the update is based on the program information and therapy information received by the patient database portal.

* * * * *